(12) United States Patent
Okawa

(10) Patent No.: US 8,034,891 B2
(45) Date of Patent: Oct. 11, 2011

(54) POLYETHER-MODIFIED ORGANOPOLYSILOXANE, DIORGANOPOLYSILOXANE-POLYETHER BLOCK COPOLYMER, THEIR PRODUCTION METHODS, AND COSMETIC PREPARATION

(75) Inventor: Tadashi Okawa, Ichihara (JP)

(73) Assignee: Dow Corning Toray Company, Ltd., Chiyoda-ku, Tokyo (JP)

(*) Notice: Subject to any disclaimer, the term of this patent is extended or adjusted under 35 U.S.C. 154(b) by 155 days.

(21) Appl. No.: 12/301,507

(22) PCT Filed: May 17, 2007

(86) PCT No.: PCT/JP2007/000531
§ 371 (c)(1),
(2), (4) Date: Oct. 22, 2009

(87) PCT Pub. No.: WO2007/135771
PCT Pub. Date: Nov. 29, 2007

(65) Prior Publication Data
US 2010/0036062 A1 Feb. 11, 2010

(30) Foreign Application Priority Data
May 19, 2006 (JP) ................................ 2006-139826

(51) Int. Cl.
*C08G 77/46* (2006.01)
(52) U.S. Cl. .............. 528/31; 528/15; 528/25; 528/403; 528/405; 528/419
(58) Field of Classification Search ........................ None
See application file for complete search history.

(56) References Cited

U.S. PATENT DOCUMENTS

| | | |
|---|---|---|
| 4,431,789 A | 2/1984 | Okazaki et al. |
| 4,722,978 A * | 2/1988 | Yu .................................. 525/403 |
| 5,118,764 A | 6/1992 | Ichinohe et al. |
| 5,145,915 A | 9/1992 | Weitemeyer et al. |
| 5,225,509 A | 7/1993 | Heinrich et al. |
| 6,150,311 A | 11/2000 | Decoster et al. |
| 6,417,323 B1 | 7/2002 | Miyanaga et al. |
| 2001/0043893 A1 | 11/2001 | Okuyama et al. |
| 2004/0242804 A1 | 12/2004 | Medsker et al. |
| 2005/0008600 A1 | 1/2005 | Nakanishi et al. |
| 2009/0137751 A1* | 5/2009 | Knott et al. .................... 525/528 |

FOREIGN PATENT DOCUMENTS

| | | |
|---|---|---|
| EP | 0381166 A2 | 8/1990 |
| EP | 1489128 A1 | 12/2004 |
| JP | 57149290 A | 9/1982 |
| JP | 2243612 A | 9/1990 |
| JP | 2302438 A | 12/1990 |
| JP | 05098016 A | 4/1993 |
| JP | 07196449 A | 8/1995 |
| JP | 7330907 A | 12/1995 |
| JP | 08012524 A | 1/1996 |
| JP | 08012545 A | 1/1996 |
| JP | 08012546 A | 1/1996 |
| JP | 09241511 A | 9/1997 |
| JP | 10036219 A | 2/1998 |
| JP | 11193331 A | 7/1999 |
| JP | 2000038311 A | 2/2000 |
| JP | 2000063225 A | 2/2000 |
| JP | 2000281523 A | 10/2000 |
| JP | 2001039845 A | 2/2001 |
| JP | 2001294666 A | 10/2001 |
| JP | 2003197030 A | 7/2003 |
| JP | 2003226611 A | 8/2003 |
| JP | 2004535485 A | 11/2004 |
| JP | 2005042097 A | 2/2005 |
| WO | WO 9942513 A1 | 8/1999 |
| WO | WO 03080712 A1 | 10/2003 |
| WO | WO 2007/075927 * | 5/2007 |
| WO | WO 2007075927 A1 | 7/2007 |

OTHER PUBLICATIONS

English language abstract for JP 57149290 extracted from espacenet.com database, dated Apr. 24, 2009.
English language abstract for JP 2243612 extracted from espacenet.com database, dated Apr. 24, 2009.
English language abstract for JP 2302438 extracted from espacenet.com database, dated Apr. 21, 2009.
English language abstract for JP 05098016 copy from Dow Corning Toray, 31 pages, Jun. 1994.
English language translation and abstract for JP 07196449 extracted from PAJ database dated Apr. 24, 2009, 30 pages.
English language abstract for JP 7330907 extracted from espacenet.com database, dated Apr. 21, 2009.
English language translation and abstract for JP 08012524 extracted from PAJ database dated Apr. 24, 2009, 33 pages.
English language translation and abstract for JP 08012545 extracted from PAJ database dated Apr. 24, 2009, 30 pages.
English language translation and abstract for JP 08012546 extracted from PAJ database dated Apr. 24, 2009, 32 pages.
English language translation and abstract for JP 09241511 extracted from PAJ database dated Apr. 24, 2009, 35 pages. English language translation and abstract for JP 10036219 extracted from PAJ database dated Apr. 24, 2009, 43 pages.
English language translation and abstract for JP 11193331 extracted from PAJ database dated Apr. 24, 2009, 59 pages.
English language abstract for JP 2000038311 extracted from espacenet.com database, dated Apr. 24, 2009.
English language translation and abstract for JP 2000063225 extracted from PAJ database dated Apr. 24, 2009, 75 pages.
English language translation and abstract for JP 2000281523 extracted from PAJ database dated Apr. 24, 2009, 109 pages.
English language translation and abstract for JP 2001039845 extracted from PAJ database dated Apr. 24, 2009, 37 pages.

(Continued)

Primary Examiner — Marc S Zimmer
(74) Attorney, Agent, or Firm — Howard & Howard Attorneys PLLC

(57) ABSTRACT

A novel polyether-modified organopolysiloxane and a novel diorganopolysiloxane-polyether block copolymer are more resistant to oxidation than the heretofore existing polyoxyalkylene-modified organopolysiloxanes and are thus more resistant to producing allergenically antigenic oxidation products during elapsed time in storage. Methods of producing this novel polyether-modified organopolysiloxane and novel diorganopolysiloxane-polyether block copolymer are also provided, as well as cosmetic that the modified organopolysiloxane or diorganopolysiloxane-polyether block copolymer.

39 Claims, 2 Drawing Sheets

OTHER PUBLICATIONS

English language abstract for JP2001294666 extracted from PAJ database, dated Apr. 24, 2009.
English language translation and abstract for JP 2003197030 extracted from PAJ database dated Apr. 24, 2009, 57 pages.
English language translation and abstract for JP 2003226611 extracted from PAJ database dated Apr. 24, 2009, 81 pages.
English language abstract for JP 2004535485 extracted from espacenet.com database, dated Apr. 24, 2009.
English language abstract for JP2005042097 extracted from espacenet.com database, dated Apr. 24, 2009.
English language abstract for WO 9942513 extracted from espacenet.com database, dated Apr. 21, 2009.
English language abstract for WO 03080712 extracted from espacenet.com database, dated Apr. 21, 2009.
PCT International Search Report for PCT/JP2007/000531, dated Aug. 28, 2007, 2 pages.
Article: Bergh et al., "Contact Allergens from Surfactants", Journal of Pharmaceuticals Sciences, vol. 87, No. 3, 1998, pp. 276-282.
Article: Bergh et al., "Formation of formaldehyde and peroxides by air oxidation of high purity polyoxyethylene surfactants", Contact Dermatitis, vol. 39, 1998, pp. 14-20.
Article: Bergh, "Allergenic Oxidation Products in Ethoxylated Non-Ionic Surfactants", Acta Dermato-Venereologica, Supplement #205, No. 79, 1999, pp. 5-26.
Article: Bergh et al., "Atmospheric Oxidation of Poly (oxyethylene) Alcohols", Journal of Pharmaceutical Sciences, vol. 88, No. 4, 1999, pp. 483-488.
Article: Bodin et al., "Identification and allergenic activity of hydroxyaldehydes—a new type of oxidation . . .", Contact Dermatitis, vol. 44, 2001, pp. 207-212.

* cited by examiner

[Figure 1]
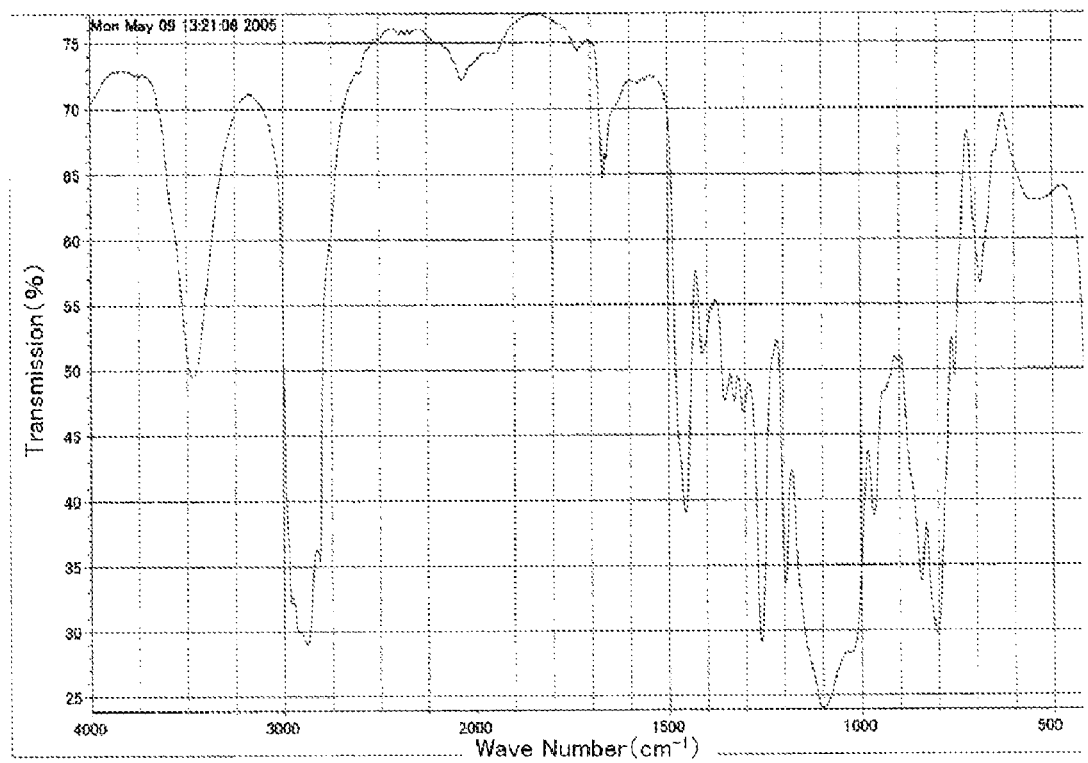

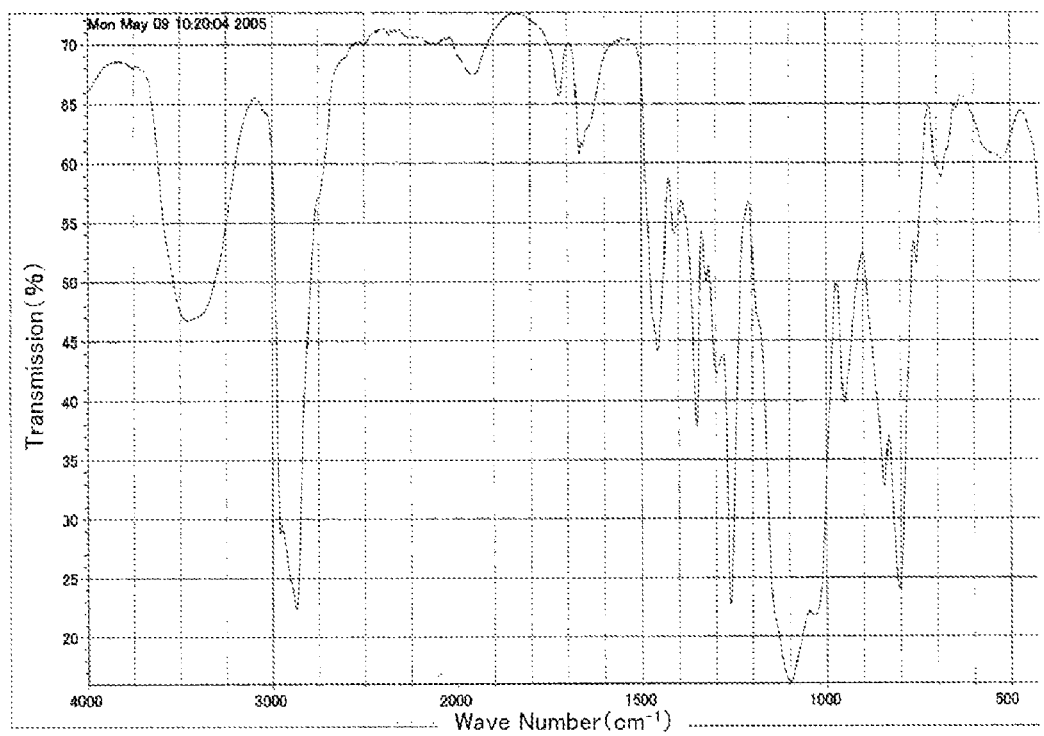
[Figure 2]

POLYETHER-MODIFIED ORGANOPOLYSILOXANE, DIORGANOPOLYSILOXANE-POLYETHER BLOCK COPOLYMER, THEIR PRODUCTION METHODS, AND COSMETIC PREPARATION

RELATED APPLICATIONS

This application claims priority to and all the advantages of International Patent Application No. PCT/JP2007/000531, filed on May 17, 2007, which claims priority to Japanese Patent Application No. JP 2006-139826, filed on May 19, 2006.

FIELD OF THE INVENTION

The present invention relates to novel polyether-modified organopolysiloxanes and methods for their production, novel diorganopolysiloxane-polyether block copolymers and methods for their production, and cosmetics that contain the preceding. The present invention more particularly relates to novel polyether-modified organopolysiloxanes and novel diorganopolysiloxane-polyether block copolymers that are more resistant to oxidation in the presence of air than the heretofore known polyoxyalkylene-modified organopolysiloxanes and diorganopolysiloxane-polyoxyalkylene block copolymers and hence that are less likely to produce carbonyl-functional allergenically antigenic compounds as represented by formaldehyde, to methods for producing these novel polyether-modified organopolysiloxanes and novel diorganopolysiloxane-polyether block copolymers, and to cosmetics that contain the preceding.

BACKGROUND ART

Polyoxyalkylene-modified organopolysiloxanes, which are a type of polyether-modified organopolysiloxanes, have heretofore been produced by a hydrosilylation reaction in the presence of a hydrosilylation reaction catalyst (e.g., chloroplatinic acid) between silicon-bonded hydrogen atom-functional organopolysiloxane and polyoxyalkylene bearing an aliphatically unsaturated group (e.g., allyl group) in terminal position. However, it is known that polyoxyalkylene-modified organopolysiloxanes (i.e., a type of polyether-modified organopolysiloxanes) produced in this manner are readily susceptible to oxidation in the presence of air and that allergenically antigenic oxidation products, e.g., formaldehyde, other aldehydes, formate esters, and so forth, are thereby produced with elapsed time in storage.

The established theory for the mechanism underlying this aldehyde production is as follows. When a hydrosilylation reaction is carried out between an organopolysiloxane containing silicon-bonded hydrogen atoms and an aliphatically unsaturated group (e.g., allyl)-terminated polyoxyalkylene in the presence of a platinum catalyst using a polyoxyalkylene monoallyl ether as the aliphatically unsaturated group (e.g., allyl)-terminated polyoxyalkylene, the allyl group undergoes an internal rearrangement in a secondary reaction to produce the polyoxyalkylene mono-1-propenyl ether. This polyoxyalkylene mono-1-propenyl ether, however, is refractory to reaction with the organopolysiloxane containing silicon-bonded hydrogen atoms.

Due to this, it remains as an impurity, along with unreacted polyoxyalkylene monoallyl ether, in the polyoxyalkylene-modified organopolysiloxane produced by the normal hydrosilylation reaction. The unreacted polyoxyalkylene monoallyl ether is gradually isomerized under the action of the residual platinum catalyst into polyoxyalkylene mono-1-propenyl ether.

The ether linkage is cleaved when water acts on the polyoxyalkylene-modified organopolysiloxane containing these impurities, resulting in the production of propionaldehyde and the generation of undesirable odor. This reaction is accelerated by the presence of acid, and its reaction rate rises as the pH declines.

U.S. Pat. No. 5,225,509 and Japanese Unexamined Patent Application Publication No. Hei 07-330907 (JP H07-330907 A) disclose a method in which alkylation is carried out by the hydrogenation of residual unsaturated double bonds. It is reported that this method eliminates the unsaturated bonds in a polyoxyalkylene monoallyl ether and polyoxyalkylene monopropenyl ether, and that as a consequence odor substances such as aldehydes are substantially not produced and an odor-free polyoxyalkylene-modified organopolysiloxane can be produced.

Japanese Patent No. 2,137,062 reports that, based on the elucidation of the odor mechanism cited above, the removal of odor substances produced by subjecting a polyoxyalkylene-modified organopolysiloxane containing the aforementioned impurities to treatment under prescribed conditions with water and an aqueous solution having a pH of 7 or less until the degree of unsaturation originating in the residual double-containing polyoxyalkylene in the copolymer reaches to 0.002 or less can yield a polysiloxane-polyoxyalkylene copolymer that does not produce undesirable odor with elapsed time.

These production methods can produce the odor-free polyoxyalkylene-modified organopolysiloxane that does not contain carbonyl-functional allergenically antigenic compounds such as aldehydes. However, they cannot prevent the production of carbonyl-functional allergenically antigenic compounds (typified by formaldehyde) during post-production storage. This is due to the fact that the polyoxyalkylene chain itself is quite susceptible to oxidation.

It has been reported in, for example, *Acta Dermato-Venereologica*, 79, 5-26 (1999); *J. Pharm. Sci.*, 87, 276 (1998); *Contact Dermatitis*, 44, 207 (2001); *Contact Dermatitis*, 39, 14 (1998); *J. Pharm. Sci.*, 88, 4 (1999); and *Contact Dermatitis*, 44, 207-212 (2001) that the polyoxyalkylenes undergo oxidative degradation in the presence of air to give various carbonyl-functional allergenically antigenic compounds, and hence the oxidative degradation of the silicon-bonded polyoxyalkylene chains in polyoxyalkylene-modified organopolysiloxanes is also unavoidable.

[Patent Reference 1] U.S. Pat. No. 5,225,509
[Patent Reference 2] Japanese Unexamined Patent Application Publication No. Hei 07-330907
[Patent Reference 3] Japanese Patent No. 2,137,062
[Nonpatent Reference 1] *Acta Dermato-Venereologica*, 79, 5-26 (1999)
[Nonpatent Reference 2] *Pharm. Sci.*, 87, 276 (1998); *Contact Dermatitis*, 44, 207 (2001)
[Nonpatent Reference 3] *Contact Dermatitis*, 39, 14 (1998); *J. Pharm. Sci.*
[Nonpatent Reference 4] *Contact Dermatitis*, 44, 207-212 (2001)

DISCLOSURE OF THE INVENTION

Problems to Be Solved by the Invention

The present inventor therefore carried out intensive investigations in order to develop a novel polyether-modified organopolysiloxane and a novel diorganopolysiloxane-polyether block copolymer that do not produce these carbonyl-functional allergenically antigenic compounds during elapsed time in storage, and as a result—by changing the silicon-bonded polyoxyalkylene chain to a polyglycidyl ether or a glycidyl ether/alkylene oxide copolymer—invented a polyether-modified organopolysiloxane and a diorganopolysiloxane-polyether block copolymer that resist the production of carbonyl-functional allergenically antigenic compounds.

An object of the present invention is to provide a novel polyether-modified organopolysiloxane that is not polyoxyalkylene modified; a further object of the present invention is to provide a method of producing said novel polyether-modified organopolysiloxane. Additional objects of the present invention are to provide a diorganopolysiloxane/novel polyether block copolymer that is not a diorganopolysiloxane-polyoxyalkylene block copolymer; to provide a novel polyether-modified organopolysiloxane and diorganopolysiloxane-polyether block copolymer that, in comparison to the heretofore existing polyoxyalkylene-modified organopolysiloxanes, are more resistant to oxidation in the presence of air, are therefore more resistant to producing allergenically antigenic oxidation products (e.g., formaldehyde, other aldehydes, formate esters, and so forth) during elapsed time in storage, and thus exhibit a higher environmental compatibility and a higher product stability; and to provide methods of producing said novel polyether-modified organopolysiloxane and diorganopolysiloxane-polyether block copolymer. Yet another object of the present invention is to provide a cosmetic that contains such novel polyether-modified organopolysiloxane or diorganopolysiloxane-polyether block copolymer that is resistant to oxidation in the presence of air and therefore resists producing allergenically antigenic oxidation products (e.g., formaldehyde, other aldehydes, formate esters, and so forth) during elapsed time in storage and thus exhibits a high environmental compatibility and a high product stability.

Means Solving the Problems

The aforementioned objects are achieved by

[1] A polyether-modified organopolysiloxane represented by the average unit formula (1)

$$R^1_a R^2_b SiO_{(4-a-b)/2} \quad (1)$$

{in the formula, $R^1$ is selected from the group consisting of a monovalent hydrocarbyl group that does not contain an aliphatically unsaturated bond, a monovalent fluorohydrocarbyl group that does not contain an aliphatically unsaturated bond, and an organic group represented by general formula (2)

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, Z is an alkyleneoxy group, m is 0-200, Y is hydrogen atom or is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and glycidyl group, and p is an integer from 1 to 6]

wherein at least 80 mol % of $R^1$ in the molecule is a monovalent hydrocarbyl group that does not contain an aliphatically unsaturated bond;

$R^2$ is an organic group represented by general formula (3)

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, Z is an alkyleneoxy group, n is 1-200, m is 0-200, n and m satisfy $0.5<n/(n+m)\leq 1$, Y is hydrogen atom or is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and glycidyl group, p is an integer from 1 to 6, X is a divalent group represented by general formula (4) or general formula (5)

(in the preceding formulas, W is a monovalent hydrocarbyl group that does not contain an aliphatically unsaturated bond or is a monovalent fluorohydrocarbyl group that does not contain an aliphatically unsaturated bond), wherein the configuration of the X and Z groups may be random, block, alternating, or a combination of the preceding];

a has an average value of $1.0 \leq a \leq 2.5$; b has an average value of $0.001 \leq b \leq 1.5$; and a and b satisfy an average of $1.001 \leq a+b \leq 3.0$};

[2] The polyether-modified organopolysiloxane according to [1], wherein, in average unit formula (1), 100 mol % of the silicon-bonded $R^1$ is a monovalent hydrocarbyl group that does not contain an aliphatically unsaturated bond; $R^3$ is an alkylene group or alkyleneoxyalkylene group having 2 to 20 carbon atoms, Z is an alkyleneoxy group having 2 to 6 carbon atoms; Y is hydrogen atom, an alkyl group having no more than 20 carbon atoms, or a saturated aliphatic acyl group having no more than 20 carbon atoms; W in the group X is an alkyl group; and p is 1 or 2;

[3] The polyether-modified organopolysiloxane according to [2], wherein the monovalent hydrocarbyl group that does not contain an aliphatically unsaturated bond constituting $R^1$ is methyl; the alkylene group constituting $R^3$ is propylene or butylene; the alkyleneoxyalkylene group constituting $R^3$ is propyleneoxyethylene, ethyleneoxyethylene, propyleneoxypropylene, a group represented by formula (20), or a group represented by formula (21);

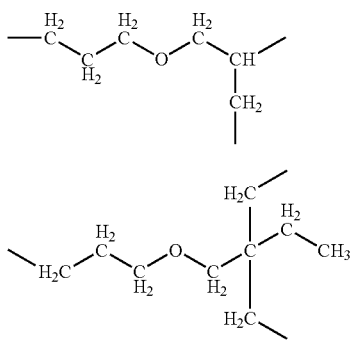

and the alkyl group constituting W in the group X is an alkyl group having 1 to 4 carbon atoms;

[4] The polyether-modified organopolysiloxane according to [1], [2], or [3], wherein n and m satisfy $0.9 \leq n/(n+m) \leq 1$;

[5] The polyether-modified organopolysiloxane according to [4], wherein m=0 and n/(n+m)=1; and

[6] A method of producing the polyether-modified organopolysiloxane of [1], comprising
carrying out a hydrosilylation reaction between
(a) a silicon-bonded hydrogen atom-containing organopolysiloxane represented by average unit formula (6)

$$R^1_a H_b SiO_{(4-a-b)/2} \quad (6)$$

($R^1$, a, and b in the formula are defined as in [1]) and
(b) a double bond-terminated polyether represented by general formula (7)

$$R(\!-\!O\!-\!X_n\!-\!Z_m\!-\!Y)_p \quad (7)$$

[in the formula, R is a double bond-terminated p-valent hydrocarbyl group having 2 to 20 carbon atoms or a group comprising said hydrocarbyl group having an ether linkage (C—O—C) therein, and X, n, Z, m, Y, p, and the configuration of X and Z groups are defined as in [1]]
in the presence of
(c) a hydrosilylation reaction catalyst.

The aforementioned objects are also achieved by

[7] The polyether-modified organopolysiloxane according to [1], wherein the polyether-modified organopolysiloxane is represented by average structural formula (8)

$$A[(R^6)_2SiO]_x[(R^6)(R^2)SiO]_y Si(R^6)_2 A \quad (8)$$

{in the formula, $R^6$ is a monovalent hydrocarbyl group that does not contain an aliphatically unsaturated bond;
$R^2$ is an organic group represented by general formula (3)

$$-R^3(\!-\!O\!-\!X_n\!-\!Z_m\!-\!Y)_p \quad (3)$$

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above (wherein W in the group X is an alkyl group), Z is an alkyleneoxy group having 2 to 6 carbon atoms, n is 1-200, m is 0-200, n and m satisfy $0.5 < n/(n+m) \leq 1$, Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond, and p is an integer from 1 to 6, wherein the configuration of the X and Z groups may be random, block, alternating, or a combination of the preceding];
A is $R^6$ or $R^2$; x is 0-500; y is 0-100; x+y is 1-600; and when y is 0, at least one of A is $R^2$};

[8] The polyether-modified organopolysiloxane according to [7], wherein at least 50 mol % of the monovalent hydrocarbyl group that does not contain an aliphatically unsaturated bond constituting $R^6$ is methyl; $R^3$ is an alkylene or alkyleneoxyalkylene having 2 to 20 carbon atoms; Z is an alkyleneoxy having 2 or 3 carbon atoms; Y is hydrogen atom; W in the group X is an alkyl group having 1 to 4 carbon atoms; and p is 1 or 2;

[9] The polyether-modified organopolysiloxane according to [8], wherein the monovalent hydrocarbyl group that does not contain an aliphatically unsaturated bond constituting $R^6$ is methyl; the alkylene group constituting $R^3$ is propylene or butylene; the alkyleneoxyalkylene group constituting $R^3$ is propyleneoxyethylene, ethyleneoxyethylene, propyleneoxypropylene, or a group represented by formula (20) or (21) given above; the alkyleneoxy group constituting Z is ethyleneoxy; and the alkyl group constituting W in the group X is methyl, ethyl, propyl, or butyl;

[10] The polyether-modified organopolysiloxane according to [7], [8], or [9], wherein n and m satisfy $0.9 \leq n/(n+m) \leq 1$;

[11] The polyether-modified organopolysiloxane according to [10], wherein m=0 and n/(n+m)=1; and

[12] A method of producing the polyether-modified organopolysiloxane represented by average structural formula (8)

$$A[(R^6)_2SiO]_x[(R^6)(R^2)SiO]_y Si(R^6)_2 A \quad (8)$$

{A, $R^6$, $R^2$, x, and y in the formula are defined as in [7]} according to [7], comprising
carrying out a hydrosilylation reaction between
(a) a silicon-bonded hydrogen atom-containing organopolysiloxane represented by average structural formula (9)

$$B[(R^6)_2SiO]_x[(R^6)HSiO]_y Si(R^6)_2 B \quad (9)$$

(in the formula, $R^6$ is a monovalent hydrocarbyl group that does not contain an aliphatically unsaturated bond, x is 0-500, y is 0-100, x+y is 1-600, and B is $R^6$ or H, wherein when y is 0 at least one of B is H) and
(b) a double bond-terminated polyether represented by general formula (7)

$$R(\!-\!O\!-\!X_n\!-\!Z_m\!-\!Y)_p \quad (7)$$

{in the formula, R is a double bond-terminated p-valent hydrocarbyl group having 2 to 20 carbon atoms or a group comprising said hydrocarbyl group having an ether linkage (C—O—C) therein, X is a divalent group represented by general formula (4) or general formula (5) given above (wherein W in the group X is an alkyl group), and n, Z, m, Y, p, and the configuration of X and Z groups are defined as in [7]}
in the presence of
(c) a hydrosilylation reaction catalyst.

The aforementioned objects are also achieved by

[13] The polyether-modified organopolysiloxane according to [1], wherein the polyether-modified organopolysiloxane is represented by average structural formula (10)

$$A[(R^6)_2SiO]_x[(R^6)(R^2)SiO]_y[(R^6)(R^7)SiO]_z Si(R^6)_2 A \quad (10)$$

(in the formula, $R^6$ is a monovalent hydrocarbyl group having 2 to 20 carbon atoms that does not contain an aliphatically unsaturated bond or is a group comprising said hydrocarbyl having an ether linkage (C—O—C) therein;

$R^2$ is an organic group represented by general formula (3)

$$-R^3(-O-X_n-Z_m-Y)_p \quad (3)$$

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above (wherein W in the group X is an alkyl group), Z is an alkyleneoxy group having 2 to 6 carbon atoms, n is 1-200, m is 0-200, n and m satisfy $0.5<n/(n+m)\leq 1$, Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond, and p is an integer from 1 to 6, wherein the configuration of the X and Z groups may be random, block, alternating, or a combination of the preceding];

$R^7$ is an organic group represented by general formula (2)

$$-R^3(-O-Z_m-Y)_p \quad (2)$$

{in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, Z is an alkyleneoxy group, m is 0-200, Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond, and p is an integer from 1 to 6};

A is $R^6$ or $R^2$; x is 0-500; y is 0-100; z is 1-100; x+y+z is 1-600; and when y is 0, at least one of A is $R^2$);

[14] The polyether-modified organopolysiloxane according to [13], wherein at least 50 mol % of the monovalent hydrocarbyl group that does not contain an aliphatically unsaturated bond constituting $R^6$ is methyl; $R^3$ is an alkylene or alkyleneoxyalkylene group having 2 to 20 carbon atoms; Z is an alkyleneoxy group having 2 or 3 carbon atoms; Y is hydrogen atom; W in the group X is an alkyl group having 1 to 4 carbon atoms; and p is 1 or 2;

[15] The polyether-modified organopolysiloxane according to [14], wherein the monovalent hydrocarbyl group that does not contain an aliphatically unsaturated bond constituting $R^6$ is methyl; the alkylene group constituting $R^3$ is propylene or butylene; the alkyleneoxyalkylene group constituting $R^3$ is propyleneoxyethylene, ethyleneoxyethylene, propyleneoxypropylene, or a group represented by formula (20) or (21) given above; the alkyleneoxy group constituting Z is ethyleneoxy; and the alkyl constituting W in the group X is methyl, ethyl, propyl, or butyl;

[16] The polyether-modified organopolysiloxane according to [13], [14], or [15], wherein n and m satisfy $0.9\leq n/(n+m)\leq 1$;

[17] The polyether-modified organopolysiloxane according to [16], wherein m=0 and n/(n+m)=1;

and

[18] A method of producing the polyether-modified organopolysiloxane represented by average structural formula (10)

$$A[(R^6)_2SiO]_x[(R^6)(R^2)SiO]_y[(R^6)(R^7)SiO]_zSi(R^6)_2A \quad (10)$$

{A, $R^6$, $R^2$, x, y, and z in the formula are defined as in [13]}, comprising
carrying out a hydrosilylation reaction between (a) a silicon-bonded hydrogen atom-containing organopolysiloxane represented by average structural formula (11)

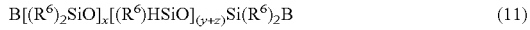
$$B[(R^6)_2SiO]_x[(R^6)HSiO]_{(y+z)}Si(R^6)_2B \quad (11)$$

(in the formula, $R^6$, x, y, and z are defined as in [13] and B is $R^6$ or H, wherein when y+z is 0 at least one of B is H)

and (b) a double bond-terminated polyether represented by general formula (7)

$$R(-O-X_n-Z_m-Y)_p \quad (7)$$

(in the formula, R is defined as in [12] and X, n, Z, m, Y, p, and the configuration of X and Z groups are defined as in [13])

and (b-1) a double bond-terminated polyether represented by general formula (12)

$$R(-O-_m-)_p \quad (12)$$

(in the formula, R is defined as in [12] and Z, m, Y, and p are defined as in [13])

in the presence of (c) a hydrosilylation reaction catalyst.

The aforementioned objects are also achieved by

[19] A diorganopolysiloxane-polyether block copolymer, characterized in that the main chain thereof is represented by general formula (13)

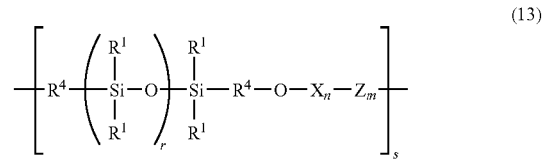

(in the formula, $R^1$ is a monovalent hydrocarbyl group that does not contain an aliphatically unsaturated bond or is a monovalent fluorohydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above, Z is an alkyleneoxy group, n is 1-200, m is 0-200, n and m satisfy $0.5<n/(n+m)\leq 1$, the configuration of the X and Z groups may be random, block, alternating, or a combination of the preceding, r is an integer from 1 to 1000, and s is an integer with a value of at least 2);

[20] A diorganopolysiloxane-polyether block copolymer represented by average structural formula (14)

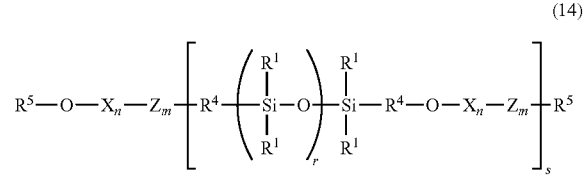

(in the formula, $R^1$ is a monovalent hydrocarbyl group that does not contain an aliphatically unsaturated bond or is a monovalent fluorohydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above, Z is an alkyleneoxy group, n is 1-200, m is 0-200, n and m satisfy $0.5<n/(n+m)\leqq 1$, the configuration of the X and Z groups may be random, block, alternating, or a combination of the preceding, r is an integer from 1 to 1000, s is an integer with a value of at least 2, and $R^5$ is a double bond-terminated monovalent hydrocarbyl group or a group comprising said hydrocarbyl group having an ether linkage (C—O—C) therein);

[21] The diorganopolysiloxane-polyether block copolymer according to [19] or [20], wherein $R^1$ is a monovalent hydrocarbyl group that does not contain an aliphatically unsaturated bond and at least 50 mol % thereof is methyl; the divalent hydrocarbyl group having 2 to 20 carbon atoms that does not contain an aliphatically unsaturated bond or group comprising said hydrocarbyl group having an ether linkage (C—O—C) therein, i.e., $R^4$, is an alkylene or alkyleneoxyalkylene group having 2 to 20 carbon atoms; Z is an alkyleneoxy group having 2 to 6 carbon atoms; and W in the group X is an alkyl group;

[22] The diorganopolysiloxane-polyether block copolymer according to [21], wherein the monovalent hydrocarbyl group that does not contain an aliphatically unsaturated bond constituting $R^1$ is methyl; the alkylene group constituting $R^3$ or $R^4$ is propylene or butylene; the alkyleneoxyalkylene group constituting $R^3$ or $R^4$ is propyleneoxyethylene, ethyleneoxyethylene, or propyleneoxypropylene; the alkyleneoxy group constituting Z is ethyleneoxy; and the alkyl group constituting W in the group X is methyl, ethyl, propyl, or butyl;

[23] The diorganopolysiloxane-polyether block copolymer according to [19], [20], [21], or [22], wherein n for the group X and m for the group Z satisfy $0.9\leqq n/(n+m)\leqq 1$; and

[24] The diorganopolysiloxane-polyether block copolymer according to [23], wherein m=0 and n/(n+m)=1.

The aforementioned objects are also achieved by

[25] A method of producing the diorganopolysiloxane-polyether block copolymer that has a main chain represented by general formula (13) that is defined in [19], comprising carrying out a hydrosilylation reaction between (d) a diorganopolyorganosiloxane that has silicon-bonded hydrogen atoms at both terminals and that is represented by average structural formula (15)

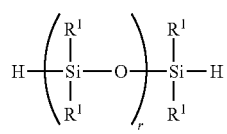

(15)

(in the formula, $R^1$ is a monovalent hydrocarbyl group that does not contain an aliphatically unsaturated bond or is monovalent fluorohydrocarbyl group that does not contain an aliphatically unsaturated bond and r is an integer from 1 to 1000)

and (e) a double bond-diterminated polyether that is represented by general formula (16)

(16)

(in the formula, $R^5$ is a double bond-terminated monovalent hydrocarbyl group having 2 to 20 carbon atoms or is a group comprising said hydrocarbyl group having an ether linkage (C—O—C) therein, X is a divalent group represented by general formula (4) or general formula (5) given above, Z is an alkyleneoxy group, n is 1-200, m is 0-200, and n and m satisfy $0.5<n/(n+m)\leqq 1$, wherein the configuration of the X and Z groups may be random, block, alternating, or a combination of the preceding)

in the presence of (c) a hydrosilylation reaction catalyst;

and

[26] The method of producing the diorganopolysiloxane-polyether block copolymer with average structural formula (14) that is defined in [20] according to [25], wherein the hydrosilylation reaction is carried out at a ratio [(number of moles of polyether represented by general formula (16))/(number of moles of diorganopolysiloxane represented by average structural formula (15))] that is larger than 1.0 and no larger than 1.2.

The aforementioned objects are also achieved by

[27] a diorganopolysiloxane-polyether block copolymer represented by average structural formula (17)

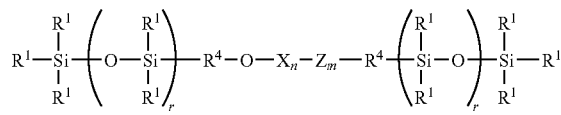

(17)

(in the formula, $R^1$ is a monovalent hydrocarbyl group that does not contain an aliphatically unsaturated bond or is monovalent fluorohydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above, Z is an alkyleneoxy group, n is 1-200, m is 0-200, n and m satisfy $0.5<n/(n+m)\leqq 1$, r is an integer from 1 to 1000, and the configuration of the X and Z groups may be random, block, alternating, or a combination of the preceding);

and

[28] a method of producing the diorganopolysiloxane-polyether block copolymer according to [27], comprising carrying out a hydrosilylation reaction between (f) (1) a diorganopolysiloxane that has a silicon-bonded hydrogen atom at one terminal and that is represented by average structural formula (18)

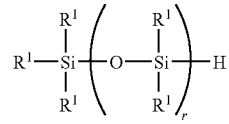

(18)

(in the formula, $R^1$ is a monovalent hydrocarbyl group that does not contain an aliphatically unsaturated bond or is a monovalent fluorohydrocarbyl group that does not contain an aliphatically unsaturated bond and r is an integer from 1 to 1000)
and
(e) a double bond-terminated polyether that is represented by general formula (16)

(in the formula, $R^5$, X, n, Z, and m are defined as in [25])
in the presence of
(c) a hydrosilylation reaction catalyst
at a ratio [(number of moles of polyether represented by general formula (16))/(number of moles of diorganopolysiloxane represented by average structural formula (18)×2)] that is larger than 1.0 and no larger than 1.2.

The aforementioned objects are also achieved by

[29] A diorganopolysiloxane-polyether block copolymer represented by average structural formula (19)

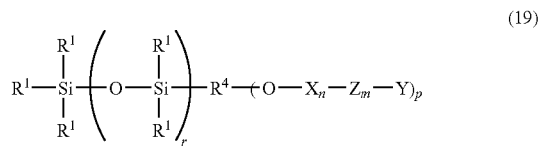

(in the formula, $R^1$ is a monovalent hydrocarbyl group that does not contain an aliphatically unsaturated bond or is a monovalent fluorohydrocarbyl group that does not contain an aliphatically unsaturated bond; $R^4$ is a divalent hydrocarbyl group having 2 to 20 carbon atoms that does not contain an aliphatically unsaturated bond or is a group comprising said hydrocarbyl group having an ether linkage (C—O—C) therein; r is an integer from 1 to 1000; X is a divalent group represented by general formula (4) or general formula (5) given above; Z is an alkyleneoxy group; n is 1-200; m is 0-200; n and m satisfy $0.5<n/(n+m)\leq 1$; Y is hydrogen atom or is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and glycidyl group; and the configuration of the X and Z groups may be random, block, alternating, or a combination of the preceding);
and

[30] A method of producing the diorganopolysiloxane-polyether block copolymer according to [29], comprising carrying out a hydrosilylation reaction between
(f) a diorganopolysiloxane that has a silicon-bonded hydrogen atom at one terminal and that is represented by average structural formula (18)

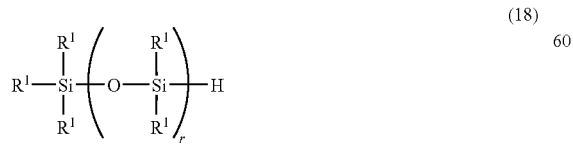

(in the formula, $R^1$ is a monovalent hydrocarbyl group that does not contain an aliphatically unsaturated bond or is a monovalent fluorohydrocarbyl group that does not contain an aliphatically unsaturated bond and r is an integer from 1 to 1000)
and
(b) a double bond-terminated polyether represented by general formula (7)

(in the formula, R is a double bond-terminated p-valent hydrocarbyl group having 2 to 20 carbon atoms or a group comprising said hydrocarbyl group having an ether linkage (C—O—C) therein, X is a divalent group represented by general formula (4) or general formula (5) given above, Z is an alkyleneoxy group, n is 1-200, m is 0-200, n and m satisfy $0.5<n/(n+m)\leq 1$, Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond, p is an integer from 1 to 6, and the configuration of the X and Z groups may be random, block, alternating, or a combination of the preceding)
in the presence of
(c) a hydrosilylation reaction catalyst
at a ratio [(number of moles of polyether represented by general formula (7))/(number of moles of diorganopolysiloxane represented by average structural formula (18))] that is larger than 1.0 and no larger than 1.2.

The aforementioned objects are also achieved by

[31] A diorganopolysiloxane-polyether block copolymer characterized in that its main chain is represented by general formula (59)

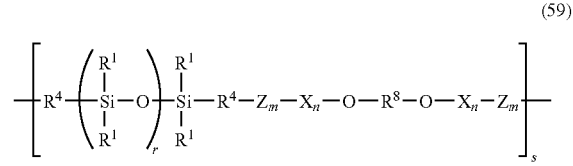

(in the formula, $R^1$ is a monovalent hydrocarbyl group that does not contain an aliphatically unsaturated bond or is a monovalent fluorohydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, $R^8$ is a divalent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above, Z is an alkyleneoxy group, n is 1-200, m is 0-200, n and m satisfy $0.5<n/(n+m)\leq 1$, the configuration of the X and Z groups may be random, block, alternating, or a combination of the preceding, r is an integer from 1 to 1000, and s is an integer with a value of at least 2);-

[32] A diorganopolysiloxane-polyether block copolymer represented by average structural formula (60)

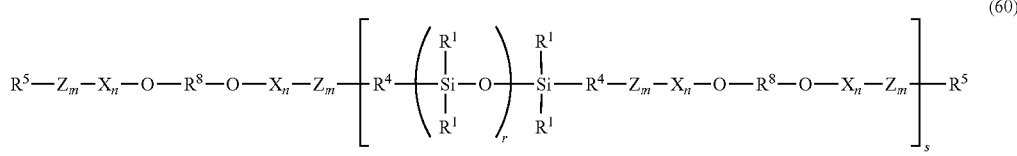
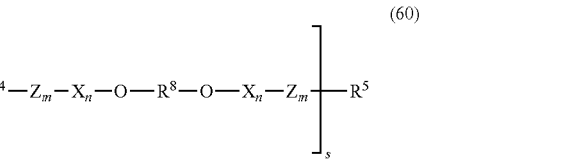

(in the formula, $R^1$ is a monovalent hydrocarbyl group that does not contain an aliphatically unsaturated bond or is a monovalent fluorohydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, $R^5$ is double bond-terminated monovalent hydrocarbyl group having 2 to 20 carbon atoms or is a group comprising said hydrocarbyl group having an ether linkage (C—O—C) therein, $R^8$ is a divalent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above, Z is an alkyleneoxy group, n is 1-200, m is 0-200, n and m satisfy $0.5<n/(n+m)\leq 1$, the configuration of the X and Z groups may be random, block, alternating, or a combination of the preceding, r is an integer from 1 to 1000, and s is an integer with a value of at least 2);

[33] A method of producing the diorganopolysiloxane-polyether block copolymer represented by general formula (59) that is defined in [31], comprising
carrying out a hydrosilylation reaction between
(d) a diorganopolyorganosiloxane that has silicon-bonded hydrogen atoms at both terminals and that is represented by average structural formula (15)

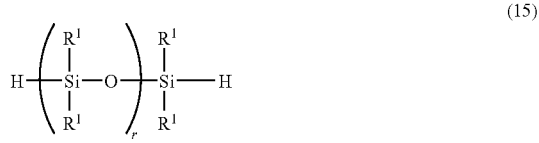

(in the formula, $R^1$ is a monovalent hydrocarbyl group that does not contain an aliphatically unsaturated bond or is a monovalent fluorohydrocarbyl group that does not contain an aliphatically unsaturated bond and r is an integer from 1 to 1000)
and
(g) a double bond-diterminated polyether that is represented by general formula (61)

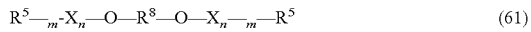

(in the formula, $R^5$ is a double bond-terminated monovalent hydrocarbyl group having 2 to 20 carbon atoms or is a group comprising said hydrocarbyl having an ether linkage (C—O—C) therein, $R^8$ is a divalent hydrocarbyl group that does not contain an aliphatically unsaturated bond or is a divalent group comprising said hydrocarbyl group having an ether linkage (C—O—C) therein, X is a divalent group represented by general formula (4) or general formula (5) given above, Z is an alkyleneoxy group, n is 1-200, m is 0-200, and n and m satisfy $0.5<n/(n+m)\leq 1$, wherein the configuration of the X and Z groups may be random, block, alternating, or a combination of the preceding)
in the presence of
(c) a hydrosilylation reaction catalyst;

[34] The method of producing the diorganopolysiloxane-polyether block copolymer with average structural formula (60) defined in [32] according to [33], wherein the hydrosilylation reaction is carried out at a ratio [(number of moles of polyether represented by general formula (61))/(number of moles of diorganopolysiloxane represented by average structural formula (15))] that is larger than 1.0 and no larger than 1.2;

[35] The method of producing the polyether-modified organopolysiloxane according to [6], [12], or [18], wherein the hydrosilylation reaction catalyst (c) is a platinum compound catalyst; and

[36] The method of producing the diorganopolysiloxane-polyether block copolymer according to [25], [26], [28], [30], [33], or [34], wherein the hydrosilylation reaction catalyst (c) is a platinum compound catalyst.

The aforementioned objects are also accomplished by

[37] A cosmetic that contains at least one selection from the group consisting of the polyether-modified organopolysiloxanes and the diorganopolysiloxane-polyether block copolymers listed below:

a polyether-modified organopolysiloxane represented by average unit formula (1), wherein $R^1$ therein is a monovalent hydrocarbyl group that does not contain an aliphatically unsaturated bond, W in the X in the organic group represented by general formula (3) is a monovalent hydrocarbyl group that does not contain an aliphatically unsaturated bond, Z is an oxyalkylene group having 2 to 6 carbon atoms, n and m satisfy $0.9\leq n/(n+m)\leq 1$, and Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond;

a polyether-modified organopolysiloxane represented by average structural formula (8), wherein W in the X in the organic group represented by genera formula (3) is a monovalent hydrocarbyl group that does not contain an aliphatically unsaturated bond, Z is an oxyalkylene group having 2 to 6 carbon atoms, n and m satisfy $0.9\leq n/(n+m)\leq 1$, and Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond;

a polyether-modified organopolysiloxane represented by average structural formula (10), wherein Z in the organic group represented by general formula (2) is an oxyalkylene group having 2 to 6 carbon atoms, W in the X group in the organic group represented by general formula (3) is a monovalent hydrocarbyl that does not contain an aliphatically unsaturated bond, Z is an oxyalkylene group having 2 to 6 carbon atom, n and m satisfy $0.9\leq n/(n+m)\leq 1$, and Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond;

a diorganopolysiloxane-polyether block copolymer having a main chain represented by general formula (13) or general formula (59), wherein $R^1$ therein is a monovalent hydrocarbyl group that does not contain an aliphatically unsaturated bond, W in the group X is a monovalent hydrocarbyl group that does not contain an aliphatically unsaturated bond, and Z is not present (that is, m=0);

a diorganopolysiloxane-polyether block copolymer represented by average structural formula (14), average structural formula (17), or average structural formula (60), wherein $R^1$ therein is a monovalent hydrocarbyl group that does not contain an aliphatically unsaturated bond, W in the group X is a monovalent hydrocarbyl group that does not contain an aliphatically unsaturated bond, and Z is not present (that is, m=0); and a diorganopolysiloxane-polyether block copolymer represented by average structural formula (19), wherein $R^1$ therein is a monovalent hydrocarbyl group that does not contain an aliphatically unsaturated bond, Z is not present (that is, m=0), W in the group X is a monovalent hydrocarbyl group that does not contain an aliphatically unsaturated bond, and Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond;

[38] The cosmetic according to [37], wherein the monovalent hydrocarbyl group that does not contain an aliphatically unsaturated bond constituting $R^1$ is alkyl; the divalent hydrocarbyl group having 2 to 20 carbon atoms that does not contain an aliphatically unsaturated bond constituting $R^4$ or $R^8$ is an alkylene group having 2 to 20 carbon atoms; the group comprising said divalent hydrocarbyl group having an ether linkage therein is an alkyleneoxyalkylene group having 2 to 20 carbon atoms; $R^3$ in the organic group represented by general formula (3) is an alkylene or alkyleneoxyalkylene group having 2 to 20 carbon atoms; Z is not present (that is, m=0); W in the group X is an alkyl group; Y is hydrogen atom or an alkyl group having no more than 20 carbon atoms or saturated aliphatic acyl group having no more than 20 carbon atoms; and p is 1 or 2;

and

[39] The cosmetic according to [38], wherein the alkyl group constituting $R^1$ is methyl; the alkylene group constituting $R^3$ or $R^4$ is propylene or butylene; the alkyleneoxyalkylene group constituting $R^3$, $R^4$, or $R^8$ is propyleneoxyethylene, ethyleneoxyethylene, propyleneoxypropylene, the group represented by formula (20) as given above, or the group represented by formula (21) as given above; and the alkyl group constituting W in the group X is an alkyl group having 1 to 4 carbon atoms.

EFFECTS OF THE INVENTION

The polyether-modified organopolysiloxane of the present invention is a novel organopolysiloxane modified by polyglycidyl ether or by glycidyl ether/alkylene oxide copolymer. The polyether-modified organopolysiloxane of the present invention is resistant to oxidation in the presence of air and as a result resists the production of allergenically antigenic oxidation products (formaldehyde, other aldehydes, formate esters, and so forth) during elapsed time in storage and thus exhibits strong environmental compatibility and high product stability.

The methods according to the present invention of producing the polyether-modified organopolysiloxane enable the precise and convenient production of this polyether-modified organopolysiloxane.

The diorganopolysiloxane-polyether block copolymer of the present invention is resistant to oxidation in the presence of air and as a result resists the production of allergenically antigenic oxidation products (formaldehyde, other aldehydes, formate esters, and so forth) during elapsed time in storage and thus exhibits strong environmental compatibility and high product stability.

The methods according to the present invention of producing the diorganopolysiloxane-polyether block copolymer enable the precise and convenient production of this diorganopolysiloxane-polyether block copolymer.

The cosmetics according to the present invention are resistant to oxidation in the presence of the air and as a result resist the production of allergenically antigenic oxidation products (formaldehyde, other aldehydes, formate esters, and so forth) and thus exhibit strong environmental compatibility and high product stability.

BRIEF DESCRIPTION OF THE DRAWINGS

FIG. 1 is the IR chart of the poly(methyl glycidyl ether)-modified dimethylpolysiloxane per se of Example 20 after holding for 3 weeks under seal in a 50° C. oven.

FIG. 2 is the IR chart of a comparative polyoxyethylene-modified dimethylpolysiloxane per se after holding for 3 weeks under seal in a 50° C. oven.

BEST MODE FOR CARRYING OUT THE INVENTION

The polyether-modified organopolysiloxane of the present invention is represented by the average unit formula (1).

$$R^1_a R^2_b SiO_{(4-a-b)/2} \quad (1)$$

In the formula, $R^1$ is selected from the group consisting of a monovalent hydrocarbyl group that does not contain an aliphatically unsaturated bond, a monovalent fluorohydrocarbyl group that does not contain an aliphatically unsaturated bond, and a organic group represented by general formula (2)

$$—R^3(—O—Z_m—Y)_p \quad (2)$$

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, Z is an alkyleneoxy group, m is 0-200, Y is hydrogen atom or is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and glycidyl group, and p is an integer from 1 to 6]

wherein at least 80 mol % of $R^1$ in the molecule is a monovalent hydrocarbyl group that does not contain an aliphatically unsaturated bond;

$R^2$ is an organic group represented by general formula (3)

$$—R^3(—O—X_n—Z_m—Y)_p \quad (3)$$

[in the formula, $R^3$, Z, m, Y, and p are defined as above, n is 1-200, n and m satisfy $0.5<n/(n+m)\leq 1$, X is a divalent group represented by general formula (4) or general formula (5)

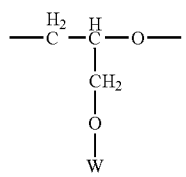  (4)

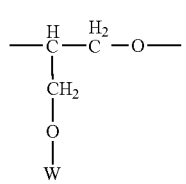  (5)

(in the preceding formulas, W is a monovalent hydrocarbyl group that does not contain an aliphatically unsaturated bond or is a monovalent fluorohydrocarbyl group that does not contain an aliphatically unsaturated bond), wherein the configuration of the X and Z groups may be random, block, alternating, or a combination of the preceding];

a has an average value of $1.0 \leq a \leq 2.5$; b has an average value of $0.001 \leq b \leq 1.5$; and a and b satisfy an average of $1.001 \leq a+b \leq 3.0$\}.

The silicon-bonded $R^1$ in general formula (1) is selected from the group consisting of a monovalent hydrocarbyl group that does not contain an aliphatically unsaturated bond, a monovalent fluorohydrocarbyl group that does not contain an aliphatically unsaturated bond, and an organic group represented by general formula (2)

$$-R^3(-O-Z_m-Y)_p \quad (2)$$

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, Z is an alkyleneoxy group, m is 0-200, Y is hydrogen atom or is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and glycidyl group, and p is an integer from 1 to 6], and preferably 100 mol % of $R^1$ is a monovalent hydrocarbyl group that does not contain an aliphatically unsaturated bond. An alkyl group is preferred for the monovalent hydrocarbyl group that does not contain an aliphatically unsaturated bond, while a perfluoroalkyl group is preferred for the monovalent fluorohydrocarbyl group that does not contain an aliphatically unsaturated bond. When the organic group represented by general formula (2) contains Z, the organic group represented by general formula (2) is no more than 20 mol % of $R^1$ from the standpoint of oxidation resistance and is preferably 0 mol %.

The monovalent hydrocarbyl group that does not contain an aliphatically unsaturated bond constituting $R^1$ preferably has 1 to 20 carbon atoms and the monovalent hydrocarbyl can be exemplified by an alkyl such as methyl, ethyl, propyl, butyl, pentyl, hexyl, and so forth; an aryl such as phenyl, tolyl, xylyl, and so forth; and an aralkyl such as benzyl. The monovalent fluorohydrocarbyl group that does not contain an aliphatically unsaturated bond preferably has 1 to 20 carbon atoms and the monovalent fluorohydrocarbyl can be exemplified by a perfluoroalkyl such as trifluoropropyl and pentafluoroethyl and so forth. $R^1$ is preferably an alkyl and more preferably is methyl.

$R^3$ in general formula (2) and general formula (3) can be exemplified by an alkylene such as ethylene, propylene, butylene, hexylene, and so forth; an alkylenephenylene such as ethylenephenylene, propylenephenylene, and so forth; an alkylenearalkylene such as ethylenebenzylene and so forth; an alkyleneoxyalkylene such as ethyleneoxyethylene, propyleneoxyethylene, hexyleneoxyethylene, and so forth; an alkyleneoxyphenylene such as ethylenoxyphenylene, propyleneoxyphenylene, and so forth; an alkyleneoxybenzylene such as propyleneoxybenzylene and so forth; and the groups shown below. The number of ether linkages in $R^3$ is preferably no greater than 3 and more preferably is 1.

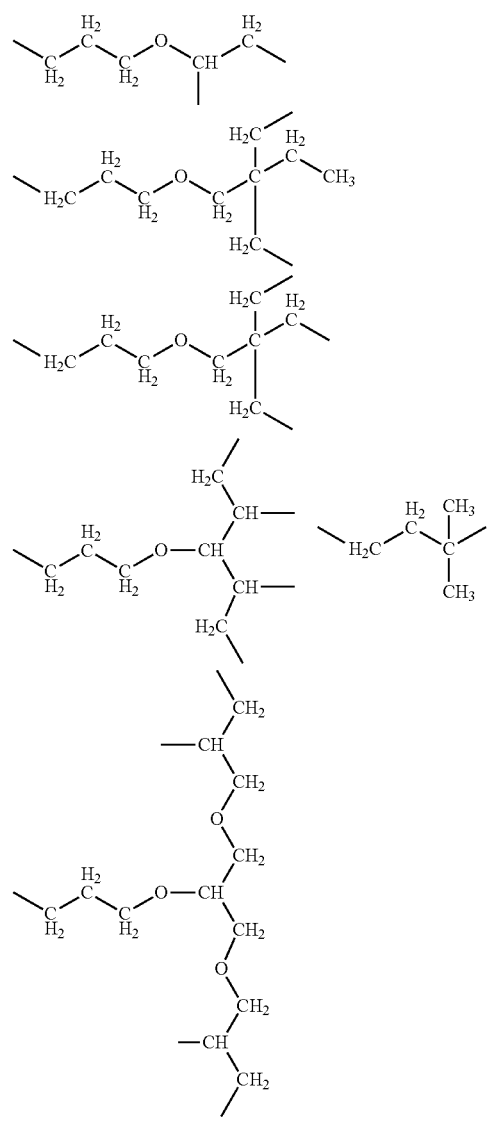

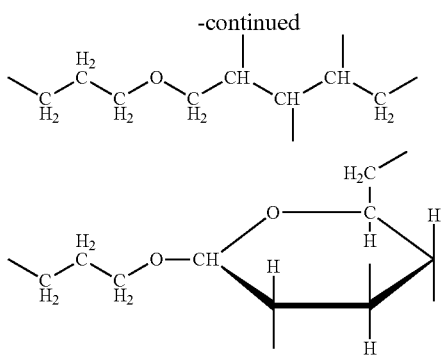

X in general formula (3) is a divalent group represented by general formula (4) or general formula (5). The subscript n represents the average degree of polymerization of —X$_n$— and is 1 to 200. When n is 2 to 200, —X$_n$— is usually a homopolymer, but may be a random copolymer or a block copolymer comprising divalent groups in which the W's are different.

—X$_n$— is the structural element that characterizes the polyether-modified organopolysiloxane of the present invention. The subscript n therein, that is, the average degree of polymerization, is 1 to 200. This n, that is, the average degree of polymerization, is preferably 2 to 70 and more preferably is 3 to 55, viewed from the perspective of obtaining an excellent balance among such properties as the capacity to lower the surface tension, permeation capacity, cleansing performance, emulsification capacity, solubilization capacity, and compatibility.

Z in general formulas (2) and (3) is an alkyleneoxy group and preferably is an alkyleneoxy group having 2 to 6 carbon atoms. Examples are ethyleneoxy, propyleneoxy, butyleneoxy, and cyclohexenoxy wherein ethyleneoxy, propyleneoxy, and ethyleneoxy plus propyleneoxy are preferred. The absence of Z (m=0) is preferred from the standpoint of the oxidation resistance as discussed above. When Z is present, m represents the average degree of polymerization of the poly (alkyleneoxy) group and is 0 (not including 0) to 200. It is preferably 0 (not including 0) to 50 and more preferably is 2 to 25, viewed from the perspective of obtaining an excellent balance among such properties as the capacity to lower the surface tension, permeation capacity, cleansing performance, emulsification capacity, solubilization capacity, and compatibility.

When m is 2 to 200, —Z$_m$— is usually a homopolymer, but may be a random copolymer or block copolymer comprising alkyleneoxy groups having different numbers of carbon atoms.

The configuration of the X and Z groups in general formula (3) may be random, block, alternating, or a combination of the preceding, wherein random, then block, and then a mixture of random and block are preferred from the standpoint of ease of production.

Y in general formulas (2) and (3) is hydrogen atom or is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and glycidyl group. The monovalent hydrocarbyl that does not contain an aliphatically unsaturated bond is exemplified by an alkyl such as methyl, ethyl, propyl, and so forth; an aryl such as phenyl, tolyl, xylyl, ethylphenyl, and so forth; benzyl; and an alkylbenzyl such as tolylmethyl and so forth.

The acyl that does not contain an aliphatically unsaturated bond can be exemplified by acetyl and propionyl.

Y is preferably hydrogen atom from the standpoint of the surface activity of the polyether-modified organopolysiloxane. However, when it is not necessary to provide the polyether-modified organopolysiloxane with a substantial surface activity, Y is preferably an alkyl group having no more than 20 carbon atoms (for example, methyl, ethyl) or a saturated aliphatic acyl group having no more than 20 carbon atoms (for example, acetyl). The glycidyl group is preferred for the purpose of imparting reactivity to the polyether-modified organopolysiloxane.

The subscript p in general formulas (2) and (3) is 1 to 6, and, considered from the standpoints of ease of acquisition of the starting materials for the synthesis and ease of synthesis, is preferably 1 to 3 and more preferably is 1 or 2.

The group X in general formula (3) may be the divalent group represented by general formula (4) or may be the divalent group represented by general formula (5) or may be a combination of the two. W in the group X is a monovalent hydrocarbyl group that does not contain an aliphatically unsaturated bond or is a monovalent fluorohydrocarbyl group that does not contain an aliphatically unsaturated bond, wherein an alkyl group is preferred from the standpoint of ease of starting material acquisition and an alkyl group having 1 to 4 carbon atoms is preferred from the standpoint of the surface activity of the polyether-modified organopolysiloxane.

The monovalent hydrocarbyl that does not contain an aliphatically unsaturated bond constituting $R^1$ is preferably an alkyl and more preferably is methyl. The alkylene constituting $R^3$ is preferably an alkylene having 2 to 4 carbon atoms, and is specifically exemplified by propylene and butylene. The alkylene in the alkyleneoxyalkylene constituting $R^3$ is preferably an alkylene group having 2 to 6 carbon atoms, and the alkyleneoxyalkylene constituting $R^3$ is specifically exemplified by propyleneoxyethylene, ethyleneoxyethylene, propyleneoxypropylene, a group represented by the following formula (20), or a group represented by the following formula (21).

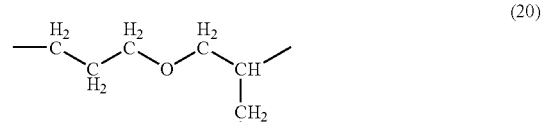

(20)

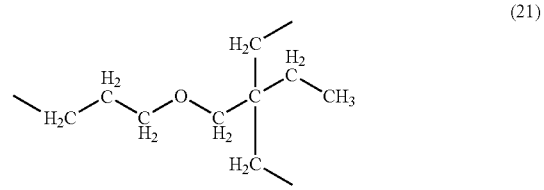

(21)

The alkyl comprising W in the group X is preferably an alkyl having 1 to 4 carbon atoms and can be specifically exemplified by methyl, ethyl, propyl, and butyl. The alkyleneoxy having 2 to 6 carbon atoms constituting Z is preferably ethyleneoxy, propyleneoxy, or ethyleneoxy plus propyleneoxy.

The organic group represented by general formula (3) preferably originates from a polyether with general formula (7) that has a molecular weight distribution (polydispersity) determined versus a polystyrene standard of 1.25 to 1.00 and particularly 1.10 to 1.00.

n and m in general formula (3) satisfy $0.5<n/(n+m)\leq 1$ from the standpoint of the oxidation resistance of the polyether-modified organopolysiloxane and preferably satisfy $0.9\leq n/(n+m)\leq 1$, wherein m=0 and n/(n+m)=1 is more preferred. m=0 and n/(n+m)=1, that is, the absence of the group Z, is preferred when the polyether-modified organopolysiloxane is to be used as a component of cosmetics or drugs for topical preparation to the skin.

a in average unit formula (1) has an average of $1.0\leq a\leq 2.5$; b has an average of $0.001\leq b\leq 1.5$; and a and b satisfy an average of $1.001\leq a+b\leq 3.0$. The surface-active performance is inadequate when there is too little $R^2$, while synthesis is difficult when $R^2/Si$ exceeds an average of 1.0, and for these reasons $0.01\leq b\leq 1.0$ is preferred and $0.05\leq b\leq 0.50$ is more preferred. The molecular structure of the polyether-modified organopolysiloxane with average unit formula (1) may be a straight chain, partially branched straight chain, cyclic, branched, network, or cage structure, but is ordinarily straight chain.

Siloxane units constituting the polyether-modified organopolysiloxane represented by average unit formula (1) can be $(R^1)_3SiO_{1/2}$, $(R^1)_2(R^2)SiO_{1/2}$, $(R^1)_2SiO_{2/2}$, $(R^1)(R^2)SiO_{2/2}$, $(R^1)SiO_{3/2}$, $(R^2)SiO_{3/2}$, and $SiO_{4/2}$.

The polyether-modified organopolysiloxane having a straight chain structure can be exemplified by a polyether-modified organopolysiloxane comprising $(R^1)_3SiO_{1/2}$, $(R^1)_2SiO_{2/2}$, and $(R^1)(R^2)SiO_{2/2}$; a polyether-modified organopolysiloxane comprising $(R^1)_3SiO_{1/2}$, $(R^1)_2(R^2)SiO_{1/2}$, $(R^1)_2SiO_{2/2}$, and $(R^1)(R^2)SiO_{2/2}$; a polyether-modified organopolysiloxane comprising $(R^1)_2(R^2)SiO_{1/2}$, $(R^1)_2SiO_{2/2}$, and $(R^1)(R^2)SiO_{2/2}$; and a polyether-modified organopolysiloxane comprising $(R^1)_3SiO_{1/2}$ and $(R^1)(R^2)SiO_{2/2}$. The cyclic polyether-modified organopolysiloxane can be exemplified by a polyether-modified organopolysiloxane comprising $(R^1)_2SiO_{2/2}$ and $(R^1)(R^2)SiO_{2/2}$ and a polyether-modified organopolysiloxane comprising only $(R^1)(R^2)SiO_{2/2}$. The polyether-modified organopolysiloxane having a branched chain or resin structure can be exemplified by a polyether-modified organopolysiloxane comprising only $(R^1)SiO_{3/2}$; a polyether-modified organopolysiloxane comprising $(R^1)SiO_{3/2}$ and $(R^2)SiO_{3/2}$; a polyether-modified organopolysiloxane comprising $(R^1)_3SiO_{1/2}$ and $SiO_{4/2}$; a polyether-modified organopolysiloxane comprising a siloxane unit or units described above as a constituent of the straight chain-structured polyether-modified organopolysiloxanes and $(R^1)SiO_{3/2}$ and/or $(R^2)SiO_{3/2}$; and a polyether-modified organopolysiloxane comprising $SiO_{4/2}$ and a siloxane unit or units described above as a constituent of the straight chain-structured polyether-modified organopolysiloxanes. It may also be a dimer comprising $(R^1)_3SiO_{1/2}$ and $(R^1)_2(R^2)SiO_{1/2}$. A small fraction of $R^1$ in these siloxane units may be replaced by hydrogen atom, hydroxyl group, and/or an alkoxy group.

The average degree of polymerization of the polyether-modified organopolysiloxane represented by average unit formula (1) is any synthesizable degree of polymerization and is not otherwise particularly limited; however, it is generally 2 to 600 and preferably is 3 to 100, when one considers the properties of the polyether-modified organopolysiloxane and the polymerization-attainable average degree of polymerization of the organopolysiloxane containing silicon-bonded hydrogen atoms, that is, organohydrogenpolysiloxane which is the precursor. The polyether-modified organopolysiloxane represented by average unit formula (1) is ordinarily a fluid at ambient temperature, but may also be a solid.

The polyether-modified organopolysiloxane represented by average unit formula (1) can be easily produced by carrying out a hydrosilylation reaction between (a) an organopolysiloxane containing silicon-bonded hydrogen atoms represented by average unit formula (6)

(in the formula, $R^1$ is selected from the group consisting of a monovalent hydrocarbyl group that does not contain an aliphatically unsaturated bond, a monovalent fluorohydrocarbyl group that does not contain an aliphatically unsaturated bond, and an organic group represented by general formula (2)

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, Z is an alkyleneoxy group, m is 0-200, Y is hydrogen atom or is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and glycidyl group, and p is an integer from 1 to 6] wherein at least 80 mol % of $R^1$ in the molecule is a monovalent hydrocarbyl group that does not contain an aliphatically unsaturated bond;

a has an average value of $1.0\leq a\leq 2.5$; b has an average value of $0.001\leq b\leq 1.5$; and a and b satisfy an average of $1.001\leq a+b\leq 3.0$)

and (b) a polyether represented by general formula (7)

[in the formula, R is a double bond-terminated p-valent hydrocarbyl group having 2 to 20 carbon atoms or a group comprising said hydrocarbyl group having an ether linkage (C—O—C) therein, X is a divalent group represented by the general formula (4) or general formula (5) given above, Z is an alkyleneoxy group, n is 1-200, m is 0-200, n and m satisfy $0<n/(n+m)\leq 1$, Y is hydrogen atom or is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and glycidyl group, p is an integer from 1 to 6, and the configuration of the X and Z groups may be random, block, alternating, or a combination of the preceding];

in the presence of (c) a hydrosilylation reaction catalyst.

The silicon-bonded hydrogen atoms in the silicon-bonded hydrogen atom-containing organopolysiloxane represented by average unit formula (6) undergoes a hydrosilylation reaction in the presence of the hydrosilylation reaction catalyst (c) with the R (a double bond-terminated p-valent hydrocarbyl group having 2 to 20 carbon atoms or a group comprising said hydrocarbyl group having an ether linkage (C—O—C) therein) in the polyether represented by general formula (7) to form the organic group ($=R^2$) represented by general formula (3).

R in the polyether represented by general formula (7) is a double bond-terminated p-valent hydrocarbyl group having 2 to 20 carbon atoms or is a group comprising said hydrocarbyl group having an ether linkage (C—O—C) therein, wherein, based on considerations of ease of starting material acquisition and ease of synthesis, p is preferably 1 to 3 and more preferably is 1 or 2. R is preferably an alkenyl group having an aliphatic double bond in terminal position and can be exemplified by an alkenyl such as vinyl, allyl, methallyl, 3-butenyl, 1,1-dimethyl-2-propenyl, i.e., the group represented by the following formula (22),

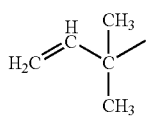
(22)

5-hexenyl, and so forth; an alkenylphenyl such as vinylphenyl, allylphenyl, and so forth; an alkenylaralkyl such as vinylbenzyl and so forth; an alkenoxyalkyl such as vinyloxyethyl, allyloxyethyl, hexenyloxyethyl, and so forth; an alkenoxyphenyl such as vinyloxyphenyl, allyloxyphenyl, and so forth; an alkenoxybenzyl group such as allyloxybenzyl and so forth; and the groups shown below.

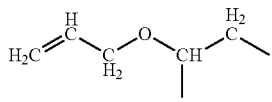

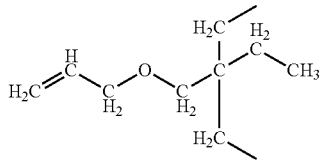

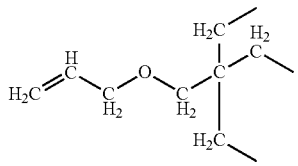

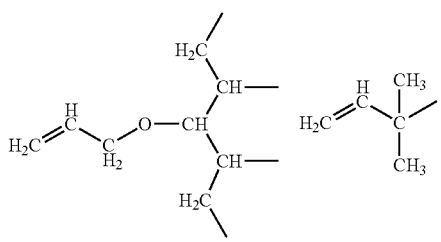

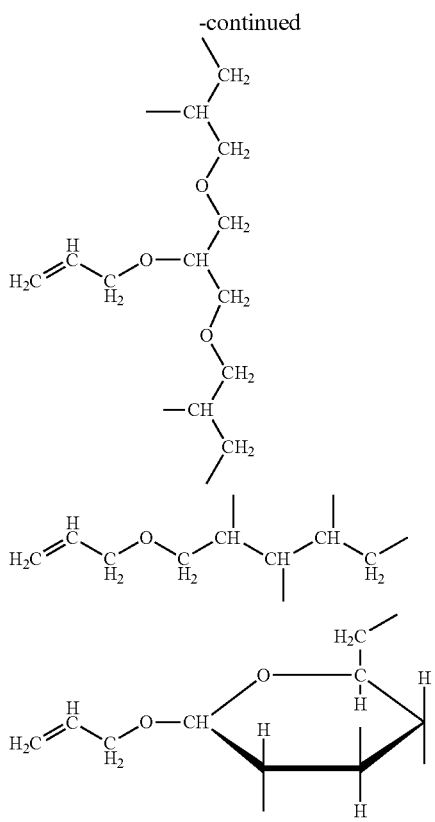

The double bond-terminated polyether represented by general formula (7) given above preferably has a molecular weight distribution (polydispersity) determined versus a polystyrene standard of 1.25 to 1.00. The reason for this is as follows: as the polydispersity approaches 1, there is less production from secondary reactions during polymerization and a higher likelihood of there being a double bond at only one terminal. Viewed from this perspective, the aforementioned molecular weight distribution (polydispersity) is preferably 1.25 to 1.00 and more preferably is 1.10 to 1.00. A high yield of the target polyether-modified organopolysiloxane is obtained when the double bond-terminated polyether with general formula (7) subjected to the hydrosilylation reaction has a value preferably of 1.25-1.00 and more preferably of 1.10-1.00 for the aforementioned molecular weight distribution (polydispersity). The molecular weight distribution (polydispersity) determined versus a polystyrene standard is determined by the procedure described at the beginning of the Examples.

n and m in the double bond-terminated polyether represented by general formula (7) given above satisfy $0.5 < n/(n+m) \leq 1$ and, viewed from the perspective of the oxidation resistance, preferably satisfy $0.9 \leq n/(n+m) \leq 1$ wherein m=0 and n/(n+m)=1, that is, the absence of Z, is most preferred.

The double bond-terminated polyether represented by general formula (7) (wherein Y is hydrogen atom), and particularly the species in which the molecular weight distribution (polydispersity) determined versus a polystyrene standard is 1.25-1.00, can be readily produced by (1) polymerizing or copolymerizing, in the presence of a base catalyst, only the glycidyl ether represented by general formula (23)

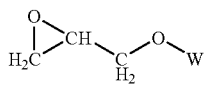

(in the formula, W is a monovalent hydrocarbyl group or a monovalent fluorohydrocarbyl group), or said glycidyl ether and an alkyleneoxide, in the presence of a p-valent hydric alcohol represented by the general formula $R(OH)_p$ (in the formula, R is a double bond-terminated monovalent hydrocarbyl group having 2 to 20 carbon atoms or a group comprising said monovalent hydrocarbyl group having an ether linkage (C—O—C) therein), and then (2) stopping the polymerization by adding an acidic substance.

When this polymerization or copolymerization is carried out in the presence of a basic ring-opening polymerization catalyst (for example, an alkali metal hydroxide or an alkali metal alcoholate), the polymerization reaction proceeds as an ideal living polymerization reaction and the molecular weight distribution (polydispersity) determined versus a polystyrene standard is low and approaches 1. As the polydispersity approaches 1, there is less production from secondary reactions and a higher likelihood of there being a double bond at only one terminal.

The double bond-terminated polyether represented by the aforementioned general formula (7)

$$R(—O—X_n—Z_m—Y)_p \quad (7)$$

(wherein Y is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and glycidyl group), and particularly the species in which the molecular weight distribution (polydispersity) determined versus a polystyrene standard is 1.25-1.00, can be readily produced by (1) polymerizing or copolymerizing, in the presence of a base catalyst, only the glycidyl ether represented by general formula (23)

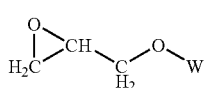

(in the formula, W is a monovalent hydrocarbyl group or a monovalent fluorohydrocarbyl group), or said glycidyl ether and an alkylene oxide, in the presence of a p-valent hydric alcohol represented by the general formula $R(OH)_p$ (in the formula, R is a double bond-terminated p-valent hydrocarbyl group having 2 to 20 carbon atoms or a group comprising said monovalent hydrocarbyl group having an ether linkage (C—O—C) therein and p is an integer from 1 to 6);

(2) converting the H in the terminal hydroxyl group to an alkali metal by reacting the polymerization product with an alkali metal hydroxide; and then (3) reacting with a hydrocarbyl monohalide that contains no more than 20 carbon atoms and that does not contain an aliphatically unsaturated bond, or with an acyl monohalide that contains no more than 20 carbon atoms and that does not contain an aliphatically unsaturated bond, or with epichlorohydrin.

The hydrosilylation reaction catalyst (c) catalyzes the hydrosilylation reaction between the silicon-bonded hydrogen atom in the silicon-bonded hydrogen atom-containing organopolysiloxane represented by average unit formula (6) and the R (a double bond-terminated p-valent hydrocarbyl group having 2 to 20 carbon atoms or a group comprising said hydrocarbyl group having an ether linkage (C—O—C) therein) in the polyether represented by general formula (7). This results in the formation of the organic group ($=R^2$) represented by general formula (3): $—R^3(—O—X_n—Z_m—Y)_p$ bonded to silicon atom.

The hydrosilylation reaction catalyst (c) can be exemplified by platinum-type catalysts, rhodium-type catalysts, and palladium-type catalysts and is preferably platinum-type catalysts. This platinum-type catalyst can be exemplified by platinum-on-silica micropowder, platinum-on-carbon micropowder, chloroplatinic acid, alcohol solutions of chloroplatinic acid, olefin complexes of platinum, alkenylsiloxane complexes of platinum, and carbonyl complexes of platinum; the platinum-type catalyst is preferably a liquid or is preferably soluble in the silicon-bonded hydrogen atom-containing organopolysiloxane represented by average unit formula (6). The alkenylsiloxane complexes of platinum can be exemplified by platinum 1,3-divinyltetramethyldisiloxane complexes and 1,3-divinyltetramethyldisiloxane complexes of chloroplatinic acid.

Component (c) is used in the aforementioned reaction in an amount sufficient to accelerate the hydrosilylation reaction, that is, in a catalytic amount, and in those instances where a platinum-type catalyst is used, the platinum-type catalyst is preferably used in an amount that provides 0.1-1,000 weight-ppm platinum metal in component (c) with reference to the total amount of the starting materials for the synthesis. The molar ratio for the amount of R (double bond-terminated group) charged with reference to the silicon-bonded hydrogen atoms is preferably 0.7 to 2.0 and more preferably is 0.8 to 1.2. This ratio is preferably 1.0 to 2.0 and more preferably 1.0 to 1.5 when it is desired to cause all of the silicon-bonded hydrogen atoms in the starting silicon-bonded hydrogen atom-containing organopolysiloxane molecule to undergo the hydrosilylation reaction.

The hydrosilylation reaction runs even at ambient temperature and is accelerated by heating. The hydrosilylation reaction may optionally be carried out in an organic solvent, and this organic solvent can be exemplified by aliphatic alcohols such as methanol, ethanol, 2-propanol, butanol, and so forth; aromatic hydrocarbons such as toluene, xylene, and so forth; aliphatic and alicyclic hydrocarbons such as n-pentane, n-hexane, cyclohexane, and so forth; and halogenated hydrocarbons such as dichloromethane, chloroform, carbon tetrachloride, and so forth. A post-treatment may be carried out in order to completely react silicon-bonded hydrogen atoms or completely eliminate silicon-bonded hydrogen atoms; for example, a hydrosilylation reaction can be carried out between the residual silicon-bonded hydrogen atom and an aliphatic hydrocarbon compound that has an aliphatic double bond in terminal position, for example, 1-hexene, or a dehydrogenation reaction can be run on silicon-bonded hydrogen atoms by the addition of a base such as sodium hydroxide.

The hydrosilylation reaction under consideration may be carried out in a batch or continuous mode. In the case of the continuous mode, a highly suitable method is described in Japanese Unexamined Patent Application Publication No. 2001-294666 (JP 2001-294666 A), wherein the hydrosilylation reaction is carried out in a cylindrical reaction apparatus that is provided in its interior with a stirring means in combination with a means that maintains plug flow.

After completion of the hydrosilylation reaction, and particularly in those instances where an organic solvent is used, the polyether-modified organopolysiloxane represented by general formula (1) is obtained, after execution of the post-treatment described above, by removing low-boiling materials by the application of heat and reduced pressure.

A representative example of the polyether-modified organopolysiloxane given by general formula (1) is the straight chain diorganopolysiloxane shown by average structural formula (8)

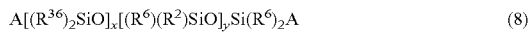

{in the formula, $R^6$ is a monovalent hydrocarbyl group that does not contain an aliphatically unsaturated bond;
$R^2$ is an organic group represented by general formula (3)

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above (wherein W in the group X is an alkyl group), Z is an alkyleneoxy group having 2 to 6 carbon atoms, n is 1-200, m is 0-200, n and m satisfy $0.5 < n/(n+m) \leq 1$, Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond, and p is an integer from 1 to 6, wherein the configuration of the X and Z groups may be random, block, alternating, or a combination of the preceding];
A is $R^1$ or $R^2$; x is 0-500; y is 0-100; x+y is 1-600; and when y is 0, at least one of A is $R^2$}.

$R^6$ is a monovalent hydrocarbyl group that does not contain an aliphatically unsaturated bond and corresponds to the monovalent hydrocarbyl group that does not contain an aliphatically unsaturated bond encompassed by $R^1$ in general formula (1). $R^6$ preferably contains 1 to 20 carbon atoms and is preferably an alkyl group and at least 50 mol % thereof is preferably methyl. $R^3$ is preferably an alkylene or alkyleneoxyalkylene having 2 to 20 carbon atoms; Z is preferably an alkyleneoxy group having 2 or 3 carbon atoms; Y is preferably hydrogen atom; W in the group X is preferably an alkyl having 1 to 4 carbon atoms; and p is preferably 1 or 2.

In more preferred embodiments, the monovalent hydrocarbyl that does not contain an aliphatically unsaturated bond constituting $R^6$ is methyl; the alkylene constituting $R^3$ has 2 to 4 carbon atoms and is specifically exemplified by propylene and butylene; the alkyleneoxyalkylene constituting $R^3$ has 2 to 6 carbon atoms in the alkylene moiety thereof and is specifically exemplified by propyleneoxyethylene, ethyleneoxyethylene, propyleneoxypropylene, the group with formula (20) as provided above, and the group with formula (21) as provided above; the alkyleneoxy constituting Z is ethyleneoxy, propyleneoxy, or ethyleneoxy plus propyleneoxy; and the alkyl constituting W in the group X is methyl, ethyl, propyl, or butyl. Viewed from the perspective of the oxidation resistance, n and m preferably satisfy $0.9 \leq n/(n+m) \leq 1$ and more preferably m=0 and n/(n+m)=1.

The configuration of the $[(R^6)_2SiO]$ and $[(R^6)(R^2)SiO]$ units is generally random, but may be block or alternating. When the main chain comprises only the $[(R^1)_2SiO]$ unit, x, defined as the number of $[(R^6)_2SiO]$ units, is 3 to 100 as a practical matter. When the main chain comprises the $[(R^6)_2SiO]$ unit and the $[(R^6)(R^2)SiO]$ unit, as a practical matter x is 3 to 100 and y, defined as the number of $[(R^6)(R^2)SiO]$ units, is 1 to 20 (wherein x>y).

The straight chain diorganopolysiloxane shown by average structural formula (8) can be specifically exemplified by
a dimethylpolysiloxane in which polyglycidyl ether is bonded through a linker group (for example, alkyleneoxy, alkyleneoxyalkyleneoxy) to silicon atoms at both terminals and
a dimethylpolysiloxane endblocked by trimethylsiloxy groups at both terminals, in which a portion of the pendant methyl groups therein is replaced by polyglycidyl ether groups through an interposed linker group (for example, alkyleneoxy, alkyleneoxyalkyleneoxy) (refer to the examples).

Average structural formula (8) may not be encompassed by general formula (1) depending on the numerical values of x and y in average structural formula (8), and in such cases the straight chain diorganopolysiloxane shown by average structural formula (8) is not an embodiment of the polyether-modified organopolysiloxane defined in claim 1.

The straight chain, polyether-modified organopolysiloxane shown by average structural formula (8) can be easily produced by carrying out a hydrosilylation reaction between
(a) a silicon-bonded hydrogen atom-containing organopolysiloxane represented by average structural formula (9)

(in the formula, $R^6$ is a monovalent hydrocarbyl group that does not contain an aliphatically unsaturated bond, x is 0-500, y is 0-100, x+y is 1-600, and B is $R^6$ or H, wherein when y is 0 at least one of B is H)
and
(b) a polyether represented by general formula (7)

{in the formula, R is a double bond-terminated p-valent hydrocarbyl group having 2 to 20 carbon atoms or a group comprising said hydrocarbyl group having an ether linkage (C—O—C) therein, X is a divalent group represented by general formula (4) or general formula (5) given above, Z is an alkyleneoxy group having 2 to 6 carbon atoms, n is 1-200, m is 0-200, n and m satisfy $0.5 < n/(n+m) \leq 1$, Y is hydrogen atom or is a group selected from a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and glycidyl group, p is an integer from 1 to 6, and the configuration of the X and Z groups may be random, block, alternating, or a combination of the preceding}
in the presence of
(c) a hydrosilylation reaction catalyst.

$R^6$, X, n, Z, m, Y, p, W, n/(n+m), the configuration of the X and Z groups, the hydrosilylation reaction catalyst, and the hydrosilylation reaction conditions can be exemplified as described above in connection with the polyether-modified organopolysiloxane given by average structural formula (8) and its method of production and in connection with the method of producing the polyether-modified organopolysiloxane shown by average unit formula (1), and these examples are preferred. The ratio [number of moles of R (double bond-terminated group) in the polyether shown by general formula (7)]/[number of moles of silicon-bonded hydrogen atoms in average structural formula (9)] in the hydrosilylation reaction under consideration is preferably 1.0 to 2.0, more preferably 1.0 to 1.5, and even more preferably 1.0 to 1.2

The configuration of the $[(R^6)_2SiO]$ and $[(R^6)HSiO]$ units is generally random, but may be block or alternating. When the main chain comprises only the $[(R^1)_2SiO]$ unit, x, defined as the number of $[(R^1)_2SiO]$ units, is 3 to 100 as a practical matter. When the main chain comprises the $[(R^6)_2SiO]$ unit and the $[(R^6)HSiO]$ unit, as a practical matter x is 3 to 100 and y, defined as the number of $[(R^6)HSiO]$ units, is 1 to 20 (wherein x>y). Applicable specific examples are a dimethylpolysiloxane having hydrogendimethylsiloxy groups at both terminals and dimethylsiloxane.methylhydrogensiloxane copolymer having trimethylsiloxy groups at both terminals.

Another representative example of the polyether-modified organopolysiloxane represented by general formula (1) is a straight chain, polyether-modified organopolysiloxane represented by average structural formula (10)

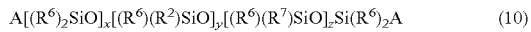  (10)

{in the formula, $R^6$ is a monovalent hydrocarbyl group that does not contain an aliphatically unsaturated bond; $R^2$ is an organic group represented by general formula (3)

  (3)

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above (wherein W in the group X is an alkyl group), Z is an alkyleneoxy group having 2 to 6 carbon atoms, n is 1-200, m is 0-200, n and m satisfy $0.5<n/(n+m)\leq 1$, Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond, and p is an integer from 1 to 6, wherein the configuration of the X and Z groups may be random, block, alternating, or a combination of the preceding];
$R^7$ is an organic group represented by general formula (2)

  (2)

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, Z is an alkyleneoxy group having 2 to 6 carbon atoms, m is 0-200, Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond, and p is an integer from 1 to 6];
A is $R^6$ or $R^2$; x is 0-500; y is 0-100; z is 1-100; x+y+z is 1-600; and when y is 0, at least one of A is $R^2$}.

The polyether-modified organopolysiloxane given by average structural formula (10) differs from the polyether-modified organopolysiloxane given by average structural formula (8) only by the additional presence of the $[(R^6)(R^7)SiO]$ unit in the former. While $R^7$ is defined as the organic group with general formula (2), m is preferably 0 to 6 from the standpoint of the oxidation resistance.

$R^6$, $R^2$, $R^3$, X, n, Z, m, Y, p, W, n/(n+m), and the configuration of the X and Z groups can be exemplified as described above in connection with the polyether-modified organopolysiloxane given by average unit formula (8), and these examples are preferred.

Average structural formula (10) may not be encompassed by general formula (1) depending on the numerical values of x, y, and z in average structural formula (10), and in such cases the straight chain diorganopolysiloxane shown by average structural formula (10) is not an embodiment of the polyether-modified organopolysiloxane defined in claim 1.

The polyether-modified organopolysiloxane represented by average structural formula (10) can be easily synthesized by carrying out a hydrosilylation reaction between (a) a silicon-bonded hydrogen atom-containing organopolysiloxane represented by average structural formula (11)

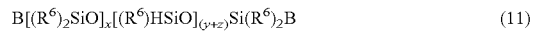  (11)

(in the formula, $R^6$ is a monovalent hydrocarbyl group that does not contain an aliphatically unsaturated bond, x is 0-500, y is 0-100, z is 1-100, x+y+z is 1-600, B is $R^6$ or hydrogen, and when y+z is 0 at least one of B is hydrogen atom)
and
(b) a double bond-terminated polyether represented by general formula (7)

  (7)

(in the formula, R is a double bond-terminated p-valent hydrocarbyl group having 2 to 20 carbon atoms or is a group comprising said hydrocarbyl group having an ether linkage (C—O—C) therein, X is a divalent group represented by general formula (4) or general formula (5) given above, Z is an alkyleneoxy group having 2 to 6 carbon atoms, n is 1-200, m is 0-200, n and m satisfy $0.5<n/(n+m)\leq 1$, Y is hydrogen atom or is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and glycidyl group, and p is an integer from 1 to 6, wherein the configuration of the X and Z groups may be random, block, alternating, or a combination of the preceding) and (b-1) a double bond-terminated polyether represented by general formula (12)

  (12)

(in the formula, R is a double bond-terminated p-valent hydrocarbyl group having 2 to 20 carbon atoms or is a group comprising said hydrocarbyl group having an ether linkage (C—O—C) therein, Z is an alkyleneoxy group having 2 to 6 carbon atoms, m is 0-200, Y is hydrogen atom or is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and glycidyl, and p is an integer from 1 to 6)
in the presence of
(c) a hydrosilylation reaction catalyst.

$R^6$, X, n, Z, m, Y, p, W, n/(n+m), the configuration of the X and Z groups, the hydrosilylation reaction catalyst, and the hydrosilylation reaction conditions can be exemplified as described above in connection with the polyether-modified organopolysiloxane given by average structural formula (8) and its method of production and in connection with the method of producing the polyether-modified organopolysiloxane shown by average unit formula (1), and these examples are preferred. The ratio [number of moles of R (double bond-terminated group) in the polyether shown by general formula (7) and number of moles of R (double bond-terminated group) in the polyether shown by general formula (7-1)]/[number of moles of silicon-bonded hydrogen atoms in average structural formula (11)] in the hydrosilylation reaction under consideration is preferably 1.0 to 2.0, more preferably 1.0 to 1.5, and even more preferably 1.0 to 1.2. The molar ratio between the double bond-terminated polyether with general formula (7) and the double bond-terminated polyether with general formula (12) may be adjusted in correspondence to the ratio between y and z in average structural formula (10).

A diorganopolysiloxane-polyether block copolymer according to the present invention is characterized in that the main chain thereof is represented by general formula (13)

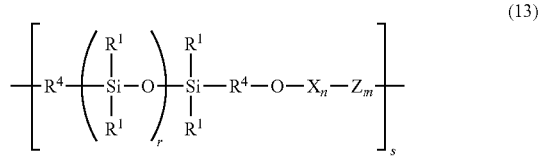

(13)

(in the formula, $R^1$ is a monovalent hydrocarbyl group that does not contain an aliphatically unsaturated bond or is a monovalent fluorohydrocarbyl group that does not contain an aliphatically unsaturated bond, X is a divalent group represented by general formula (4) or general formula (5) given above, Z is an alkyleneoxy group, n is 1-200, m is 0-200, n and m satisfy $0.5<n/(n+m)\leq 1$, r is an integer from 1 to 1000, s is an integer with a value of at least 2, $R^4$ is a divalent hydrocarbyl group having 2 to 20 carbon atoms that does not contain an aliphatically unsaturated bond or is a group comprising said hydrocarbyl group having an ether linkage (C—O—C) therein, and the configuration of the X and Z groups may be random, block, alternating, or a combination of the preceding).

With regard to the end groups, both ends may be $R^5$—as in the diorganopolysiloxane-polyether block copolymer given by average structural formula (14), or one end may be $R^5$—and the other end may be SiH, or both ends may be SiH.

The diorganopolysiloxane-polyether block copolymer having a main chain represented by general formula (13) can be easily produced by carrying out a hydrosilylation reaction between
(d) a diorganopolyorganosiloxane that has silicon-bonded hydrogen atoms at both terminals and that is represented by average structural formula (15)

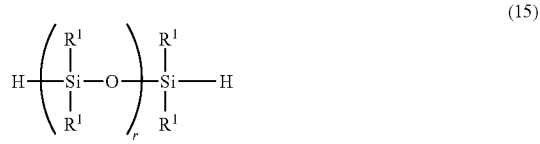

(15)

(in the formula, $R^1$ is a monovalent hydrocarbyl group that does not contain an aliphatically unsaturated bond or is a monovalent fluorohydrocarbyl group that does not contain an aliphatically unsaturated bond and r is an integer from 1 to 1000)
and
(e) a double bond-diterminated polyether that is represented by general formula (16)

$R^5$—O—$X_n$—$Z_m$—$R^5$ (16)

(in the formula, $R^5$ is a double bond-terminated monovalent hydrocarbyl group having 2 to 20 carbon atoms or is a group comprising said hydrocarbyl group having an ether linkage (C—O—C) therein, X is a divalent group represented by general formula (4) or general formula (5) given above, Z is an alkyleneoxy group, n is 1-200, m is 0-200, and n and m satisfy $0.5<n/(n+m)\leq 1$, wherein the configuration of the X and Z groups may be random, block, alternating, or a combination of the preceding)
in the presence of
(c) a hydrosilylation reaction catalyst.

This hydrosilylation reaction is preferably carried out at [number of moles of double bond-diterminated polyether with general formula (16)]/[number of moles of diorganopolyorganosiloxane that has silicon-bonded hydrogen atoms at both terminals and that is represented by average structural formula (15)] around 1.0. However, when this molar ratio is less than 1.0, the product tends to have silicon-bonded hydrogen atoms at both terminals; when this molar ratio is 1.0, the product tends to have a silicon-bonded hydrogen atom at only one terminal. This molar ratio is therefore preferably greater than 1.0 but no greater than 1.2 and more preferably is greater than 1.0 and no greater than 1.1. By doing this, a diorganopolysiloxane-polyether block copolymer represented by average structural formula (14) is obtained

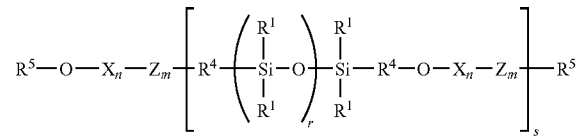

(14)

(in the formula, $R^1$ is a monovalent hydrocarbyl group that does not contain an aliphatically unsaturated bond or is a monovalent fluorohydrocarbyl group that does not contain an aliphatically unsaturated bond, X is a divalent group represented by general formula (4) or general formula (5) given above, Z is an alkyleneoxy group, n is 1-200, m is 0-200, n and m satisfy $0.5<n/(n+m)\leq 1$, r is an integer from 1 to 1000, s is an integer with a value of at least 2, $R^4$ is a divalent hydrocarbyl group having 2 to 20 carbon atoms that does not contain an aliphatically unsaturated bond or is a group comprising said hydrocarbyl group having an ether linkage (C—O—C) therein, $R^5$ is a double bond-terminated monovalent hydrocarbyl group or a group comprising said hydrocarbyl group having an ether linkage (C—O—C) therein, and the configuration of the X and Z groups may be random, block, alternating, or a combination of the preceding).

Primarily a diorganopolysiloxane-polyether block copolymer given by average structural formula (24) is obtained by carrying out a hydrosilylation reaction between the diorganopolysiloxane-polyether block copolymer with average structural formula (14) and the diorganopolysiloxane having a silicon-bonded hydrogen atom at one terminal that is shown by average structural formula (18), infra, at a molar ratio of approximately 1:1 in the presence of the hydrosilylation reaction catalyst (c).

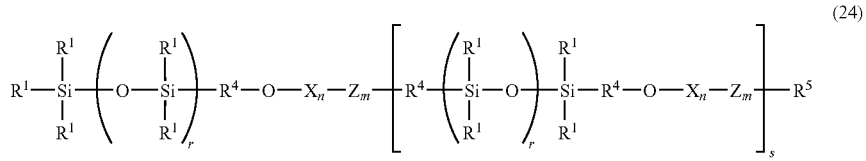
(24)

Primarily a diorganopolysiloxane-polyether block copolymer given by average structural formula (25) is obtained by carrying out a hydrosilylation reaction between the diorganopolysiloxane-polyether block copolymer with average structural formula (14) and the diorganopolysiloxane having a silicon-bonded hydrogen atom at one terminal that is shown by average structural formula (18), infra, at a molar ratio of approximately 1:2 in the presence of the hydrosilylation reaction catalyst (c).

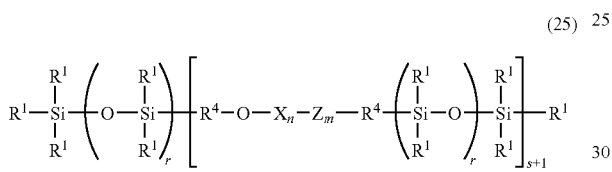
(25)

Average structural formula (17) shows a diorganopolysiloxane-polyether block copolymer that is another embodiment of the present invention

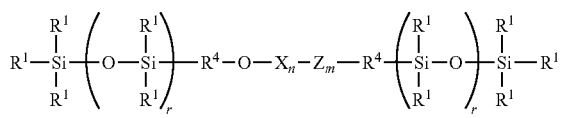
(17)

(in the formula, $R^1$ is a monovalent hydrocarbyl group that does not contain an aliphatically unsaturated bond or is a monovalent fluorohydrocarbyl group that does not contain an aliphatically unsaturated bond, X is a divalent group represented by general formula (4) or general formula (5) given above, Z is an alkyleneoxy group, n is 1-200, m is 0-200, n and m satisfy $0.5 < n/(n+m) \leq 1$, $R^4$ is a divalent hydrocarbyl group having 2 to 20 carbon atoms that does not contain an aliphatically unsaturated bond or is a group comprising said hydrocarbyl group having an ether linkage (C—O—C) therein, r is an integer from 1 to 1000, and the configuration of the X and Z groups may be random, block, alternating, or a combination of the preceding).

The aforementioned diorganopolysiloxane-polyether block copolymer can be easily produced by carrying out a hydrosilylation reaction between (f) a diorganopolysiloxane that has a silicon-bonded hydrogen atom at one terminal and that is represented by average structural formula (18)

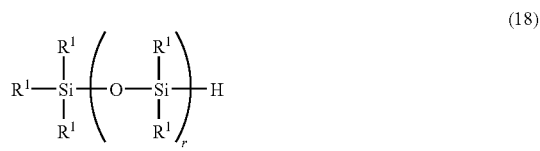
(18)

(in the formula, $R^1$ is a monovalent hydrocarbyl group that does not contain an aliphatically unsaturated bond or is a monovalent fluorohydrocarbyl group that does not contain an aliphatically unsaturated bond and r is an integer from 1 to 1000)
and
(e) a double bond-terminated polyether that is represented by general formula (16)

$$R^5-O-X_n-Z_m-R^5 \tag{16}$$

(in the formula, $R^5$ is a double bond-terminated monovalent hydrocarbyl group having 2 to 20 carbon atoms or is a group comprising said hydrocarbyl group having an ether linkage (C—O—C) therein, X is a divalent group represented by general formula (4) or general formula (5) given above, Z is an alkyleneoxy group, n is 1-200, m is 0-200, and n and m satisfy $0.5 < n/(n+m) \leq 1$, wherein the configuration of the X and Z groups may be random, block, alternating, or a combination of the preceding)
in the presence of
(c) a hydrosilylation reaction catalyst
at a ratio [(number of moles of polyether represented by general formula (16))/(number of moles of diorganopolysiloxane represented by average structural formula (18)×2)] that is larger than 1.0 and no larger than 1.2. This ratio is preferably larger than 1.0 and no larger than 1.1.

Average structural formula (19) shows a diorganopolysiloxane-polyether block copolymer that is another embodiment of the present invention

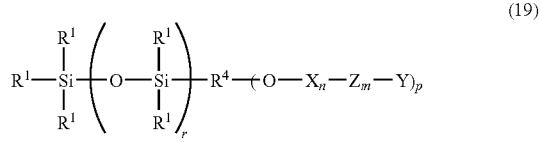
(19)

(in the formula, $R^1$ is a monovalent hydrocarbyl group that does not contain an aliphatically unsaturated bond or is a monovalent fluorohydrocarbyl group that does not contain an aliphatically unsaturated bond; $R^4$ is a divalent hydrocarbyl group having 2 to 20 carbon atoms that does not contain an aliphatically unsaturated bond or is a group comprising said hydrocarbyl group having an ether linkage (C—O—C) therein; r is an integer from 1 to 1000; X is a divalent group represented by general formula (4) or general formula (5) given above; Z is an alkyleneoxy group; n is 1-200; m is 0-200; n and m satisfy $0.5 < n/(n+m) \leq 1$; Y is hydrogen atom or is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and glycidyl group; p is an integer with a value from 1 to 6; and the configuration of the X and Z groups may be random, block, alternating, or a combination of the preceding).

The aforementioned diorganopolysiloxane-polyether block copolymer can be easily produced by carrying out a hydrosilylation reaction between (f) a diorganopolysiloxane that has a silicon-bonded hydrogen atom at one terminal and that is represented by average structural formula (18)

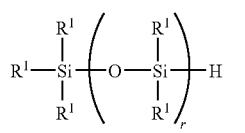

(18)

(in the formula, $R^1$ is a monovalent hydrocarbyl group that does not contain an aliphatically unsaturated bond or is a monovalent fluorohydrocarbyl group that does not contain an aliphatically unsaturated bond and r is an integer from 1 to 1000)

and (b) a double bond-terminated polyether represented by general formula (7)

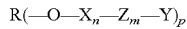

$$R(-O-X_n-Z_m-Y)_p \quad (7)$$

(in the formula, R is a double bond-terminated p-valent hydrocarbyl group having 2 to 20 carbon atoms or a group comprising said hydrocarbyl group having an ether linkage (C—O—C) therein; X is a divalent group represented by general formula (4) or general formula (5) given above; Z is an alkyleneoxy group; n is 1-200; m is 0-200; n and m satisfy $0.5 < n/(n+m) \leq 1$; Y is hydrogen atom or is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and glycidyl group; p is an integer from 1 to 6; and the configuration of the X and Z groups may be random, block, alternating, or a combination of the preceding)

in the presence of (c) a hydrosilylation reaction catalyst at a ratio [(number of moles of polyether represented by general formula (7))/(number of moles of diorganopolysiloxane represented by average structural formula (18))] that is larger than 1.0 and no larger than 1.2. This ratio is preferably larger than 1.0 but no larger than 1.1.

General formula (59) shows a diorganopolysiloxane-polyether block copolymer that is another embodiment of the present invention

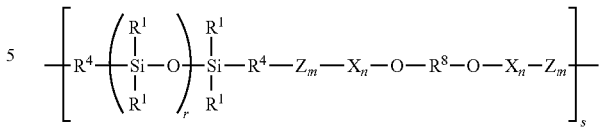

(59)

(in the formula, $R^1$ is a monovalent hydrocarbyl group that does not contain an aliphatically unsaturated bond or is a monovalent fluorohydrocarbyl group that does not contain an aliphatically unsaturated bond, X is a divalent group represented by general formula (4) or general formula (5) given above, $R^4$ is a divalent hydrocarbyl group having 2 to 20 carbon atoms that does not contain an aliphatically unsaturated bond or is a group comprising said hydrocarbyl group having an ether linkage (C—O—C) therein, $R^8$ is a divalent hydrocarbyl group having 2 to 20 carbon atoms that does not contain an aliphatically unsaturated bond or is a group comprising said hydrocarbyl group having an ether linkage (C—O—C) therein, Z is an alkyleneoxy group, n is 1-200, m is 0-200, n and m satisfy $0.5 < n/(n+m) \leq 1$, r is an integer from 1 to 1000, s is an integer with a value of at least 2, and the configuration of the X and Z groups may be random, block, alternating, or a combination of the preceding).

The diorganopolysiloxane-polyether block copolymer represented by general formula (59) can be easily produced by carrying out a hydrosilylation reaction between (d) a diorganopolyorganosiloxane that has silicon-bonded hydrogen atoms at both terminals and that is represented by average structural formula (15)

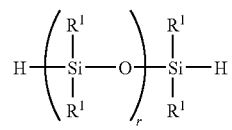

(15)

(in the formula, $R^1$ is a monovalent hydrocarbyl group that does not contain an aliphatically unsaturated bond or is a monovalent fluorohydrocarbyl group that does not contain an aliphatically unsaturated bond and r is an integer from 1 to 1000)

and (g) a double bond-diterminated polyether that is represented by general formula (61)

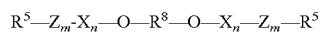

$$R^5-Z_m-X_n-O-R^8-O-X_n-Z_m-R^5 \quad (61)$$

(in the formula, $R^5$ is a double bond-terminated monovalent hydrocarbyl group having 2 to 20 carbon atoms or is a group comprising said hydrocarbyl group having an ether linkage (C—O—C) therein, $R^4$ is a divalent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above, Z is an alkyleneoxy group, n is 1-200, m is 0-200, and n and m satisfy $0.5 < n/(n+m) \leq 1$, wherein the configuration of the X and Z groups may be random, block, alternating, or a combination of the preceding)

in the presence of (c) a hydrosilylation reaction catalyst.

This hydrosilylation reaction is preferably carried out at [number of moles of double bond-diterminated polyether with general formula (61)]/[number of moles of diorganopolyorganosiloxane that has silicon-bonded hydrogen atoms at both terminals and that is represented by average structural formula (15)] around 1.0. However, when this molar ratio is less than 1.0, the product tends to have silicon-bonded hydrogen atoms at both terminals; when this molar ratio is 1.0, the product tends to have a silicon-bonded hydrogen atom at only one terminal. This molar ratio is therefore preferably greater than 1.0 but no greater than 1.2 and more preferably is greater than 1.0 and no greater than 1.1. By doing this, a diorganopolysiloxane-polyether block copolymer represented by average structural formula (60) is obtained

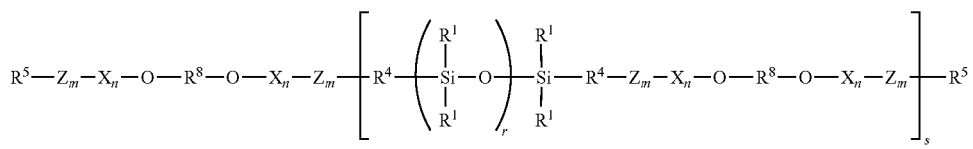

(in the formula, $R^1$ is a monovalent hydrocarbyl group that does not contain an aliphatically unsaturated bond or is a monovalent fluorohydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, $R^5$ is a double bond-terminated monovalent hydrocarbyl group having 2 to 20 carbon atoms or is a group comprising said hydrocarbyl group having an ether linkage (C—O—C) therein, $R^8$ is a divalent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above, Z is an alkyleneoxy group, n is 1-200, m is 0-200, n and m satisfy $0.5<n/(n+m)\leq 1$, r is an integer from 1 to 1000, s is an integer with a value of at least 2, and the configuration of the X and Z groups may be random, block, alternating, or a combination of the preceding).

With regard to the above-cited general formula that represent the main chain of the diorganopolysiloxane-polyether block copolymer and the above-cited average structural formulas for the diorganopolysiloxane-polyether block copolymer series:

$R^1$ is a monovalent hydrocarbyl group that does not contain an aliphatically unsaturated bond or is a monovalent fluorohydrocarbyl group that does not contain an aliphatically unsaturated bond, and is preferably a monovalent hydrocarbyl group that does not contain an aliphatically unsaturated bond. The monovalent hydrocarbyl that does not contain an aliphatically unsaturated bond preferably contains 1 to 20 carbon atoms and is exemplified by an alkyl such as methyl, ethyl, propyl, butyl, pentyl, hexyl, and so forth; an aryl such as phenyl, tolyl, xylyl, and so forth; and aralkyl such as benzyl, wherein alkyl is preferred and methyl is more preferred. The monovalent fluorohydrocarbyl that does not contain an aliphatically unsaturated bond preferably has 1 to 20 carbon atoms and can be exemplified by a perfluoroalkyl such as trifluoropropyl and pentafluoroethyl and so forth. At least 50 mol % of $R^1$ in each molecule is methyl and more preferably $R^1$ is entirely methyl.

$R^4$, which is a divalent hydrocarbyl group having 2 to 20 carbon atoms that does not contain an aliphatically unsaturated bond or is a group comprising said hydrocarbyl group having an ether linkage (C—O—C) therein, is preferably an alkylene or alkyleneoxyalkylene having 2 to 20 carbon atoms. $R^4$ preferably has no more than three ether linkages and more preferably has one ether linkage. The alkylene preferably has 2 to 6 carbon atoms and can be specifically exemplified by propylene and butylene; the alkylene in the alkyleneoxyalkylene preferably has 2 to 6 carbon atoms and the alkyleneoxyalkylene can be specifically exemplified by propyleneoxyethylene, ethyleneoxyethylene, propyleneoxypropylene, the group shown by formula (20), and the group shown by formula (21).

$R^5$ is a double bond-terminated monovalent hydrocarbyl group having 2 to 20 carbon atoms or a group comprising said hydrocarbyl group having an ether linkage (C—O—C) therein and preferably is an alkenyl group bearing an aliphatic double bond in terminal position, e.g., vinyl, allyl, methallyl, 3-butenyl, 1,1-dimethyl-2-propenyl, i.e., the group represented by the following formula (22),

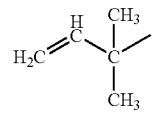

and 5-hexenyl.

$R^8$ which is a divalent group having 2 to 20 carbon atoms that does not contain an aliphatic double bond or is a group comprising said hydrocarbyl group having an ether linkage (C—O—C) therein, is preferably an alkylene or alkyleneoxyalkylene group having 2 to 20 carbon atoms. $R^8$ preferably contains no more than three ether linkages and more preferably has one ether linkage. The alkylene in the alkyleneoxyalkylene preferably has 2 to 6 carbon atoms and the alkyleneoxyalkylene can be specifically exemplified by propyleneoxyethylene, ethyleneoxyethylene, propyleneoxypropylene, the group shown by formula (20), and the group shown by formula (21).

X is a divalent group with general formula (4) or general formula (5), supra, or is a mixture of the two. W in the group X is a monovalent hydrocarbyl group that does not contain an aliphatically unsaturated bond or is a monovalent fluorohydrocarbyl group that does not contain an aliphatically unsaturated bond, and is preferably an alkyl group from the standpoint of ease of starting material acquisition and is preferably an alkyl group having 1 to 4 carbon atoms; from the standpoint of the surface activity of the polyether-modified organopolysiloxane.

—X$_n$— is typically a homopolymer for n equal to 2 to 200, but may be a random copolymer or a block copolymer comprising divalent groups in which the W's are different. —X$_n$— is the structural element that characterizes the diorganopolysiloxane-polyether block copolymers cited above. The subscript n therein, that is, the average degree of polymerization, is 1 to 200. This n, that is, the average degree of polymerization, is preferably 2 to 70 and more preferably is 3 to 55, viewed from the perspective of obtaining an excellent balance among such properties as the capacity to lower the surface tension, permeation capacity, cleansing performance, emulsification capacity, solubilization capacity, and compatibility.

Z is an alkyleneoxy group and preferably is an alkyleneoxy group having 2 to 6 carbon atoms. Examples are ethyleneoxy, propyleneoxy, butyleneoxy, and cyclohexenoxy. Z is more preferably an alkyleneoxy group having 2 or 3 carbon atoms, i.e., ethyleneoxy, propyleneoxy, and ethyleneoxy plus propyleneoxy. The absence of Z (m=0) is preferred from the standpoint of the oxidation resistance as discussed above. When Z is present, m represents the average degree of polymerization of the poly(alkyleneoxy) group and is 0 (not including 0) to 200. It is preferably 0 (not including 0) to 50 and more preferably is 2 to 25, viewed from perspective of obtaining an excellent balance among such properties as the capacity to lower the surface tension, permeation capacity, cleansing performance, emulsification capacity, solubilization capacity, and compatibility.

—$_m$— is usually a homopolymer for m equal to 2 to 200, but may be a random copolymer or block copolymer comprising alkyleneoxy groups having different numbers of carbon atoms.

The configuration of the X and Z groups may be random, block, alternating, or a combination of the preceding, wherein random, then block, and then a mixture of random and block are preferred from the standpoint of ease of production.

Y preferably is hydrogen atom, a monovalent hydrocarbyl group that contains no more than 20 carbon atoms and that does not contain an aliphatically unsaturated bond, or an acyl group that contains no more than 20 carbon atoms and that does not contain an aliphatically unsaturated bond. The monovalent hydrocarbyl that does not contain an aliphatically unsaturated bond is exemplified by an alkyl such as methyl, ethyl, propyl, and so forth; an aryl such as phenyl, tolyl, xylyl, ethylphenyl, and so forth; benzyl; and an alkylbenzyl such as tolylmethyl and so forth. The acyl that does not contain an aliphatically unsaturated bond can be exemplified by acetyl and propionyl. Y is preferably hydrogen atom from the standpoint of the surface activity of the diorganopolysiloxane-polyether block copolymer. However, when it is not necessary to provide the diorganopolysiloxane-polyether block copolymer with a substantial surface activity, Y is preferably an alkyl group having no more than 20 carbon atoms (for example, methyl, ethyl) or a saturated aliphatic acyl group having no more than 20 carbon atoms (for example, acetyl).

p is preferably 1 or 2.

n and m preferably satisfy 0.9≦n/(n+m)≦1 from the standpoint of the oxidation resistance of the diorganopolysiloxane-polyether block copolymer, and m=0 and n/(n+m)=1 is more preferred.

In more preferred embodiments, R$^1$ is methyl; R$^4$ is propylene or butylene or is propyleneoxyethylene, ethyleneoxyethylene, or propyleneoxypropylene; R$^5$ is methallyl; R$^8$ is propylene or butylene or is propyleneoxyethylene, ethyleneoxyethylene, or propyleneoxypropylene; W in the group X is methyl, ethyl, propyl, or butyl; Y is hydrogen atom; and m=0 and n/(n+m)=1.

r is an integer from 1 to 1000 and preferably is 1 to 200. s is an integer with a value of at least 2 and preferably is 2 to 50.

The double bond-terminated polyether represented by general formula (16) given above and the double bond-terminated polyether represented by general formula (61) given above preferably have a molecular weight distribution (polydispersity) determined versus a polystyrene standard of 1.25 to 1.00. The reason for this is as follows: as the polydispersity approaches 1, there is less production of by-products during polymerization and a higher likelihood of there being a double bond at only one terminal. Viewed from this perspective, the aforementioned molecular weight distribution (polydispersity) is preferably 1.25 to 1.00 and more preferably is 1.10 to 1.00. A high yield of the target diorganopolysiloxane-polyether block copolymer is obtained and by-products are reduced when the double bond-terminated polyether with general formula (16) or (61) subjected to the hydrosilylation reaction has a value preferably of 1.25-1.00 and more preferably of 1.10-1.00 for the aforementioned molecular weight distribution (polydispersity).

The double bond-terminated polyether represented by the aforementioned general formula (16), and particularly the species in which the molecular weight (polydispersity) determined versus a polystyrene standard is 1.25-1.00, can be readily produced by (1) polymerizing or copolymerizing, in the presence of a base catalyst, only the glycidyl ether represented by general formula (23)

(23)

(in the formula, W is a monovalent hydrocarbyl group or a monovalent fluorohydrocarbyl group), or said glycidyl ether and an alkylene oxide, in the presence of a monohydric alcohol represented by the general formula R$^5$OH (in the formula, R$^5$ is a double bond-terminated monovalent hydrocarbyl group having 2 to 20 carbon atoms or a group comprising said monovalent hydrocarbyl group having an ether linkage (C—O—C) therein);

(2) converting the H in the terminal hydroxyl group to an alkali metal by reacting the polymerization product with an alkali metal hydroxide; and then (3) condensing with a double bond-terminated hydrocarbyl monohalide having 2 to 20 carbon atoms.

The double bond-terminated polyether represented by the aforementioned general formula (61), and particularly the species in which the molecular weight distribution (polydispersity) determined versus a polystyrene standard is 1.25-1.00, can be readily produced by (1) polymerizing or copolymerizing, in the presence of a base catalyst, only the glycidyl ether represented by general formula (23)

(23)

(in the formula, W is a monovalent hydrocarbyl group or a monovalent fluorohydrocarbyl group), or said glycidyl ether and an alkylene oxide, in the presence of a dihydric alcohol represented by the general formula $HOR^8OH$ (in the formula, $R^8$ is a divalent hydrocarbyl group having 2 to 20 carbon atoms that does not contain an aliphatically unsaturated bond or is a group comprising said monovalent hydrocarbyl group having an ether linkage (C—O—C) therein);

(2) converting the H in the terminal hydroxyl group to an alkali metal by reacting the polymerization product with an alkali metal hydroxide; and then (3) condensing with a double bond-terminated hydrocarbyl monohalide having 2 to 20 carbon atoms.

The hydrosilylation reaction catalyst, the hydrosilylation reaction conditions, and so forth in these methods of producing the aforementioned series of diorganopolysiloxane-polyether block copolymers can be exemplified as described above in connection with the method of producing the polyether-modified organopolysiloxane given by average unit formula (1), and these examples are preferred.

The polyether-modified organopolysiloxane of the present invention and the diorganopolysiloxane-polyether block copolymer of the present invention exhibit, inter alia, surface-active behavior because they contain both a hydrophilic moiety and a hydrophobic moiety in the same molecule, and because of this, and because they have a polysiloxane moiety and a polyether moiety in the same molecule, they can be used in a variety of applications in correspondence to their particular molecular structure and characteristics, for example, as an emulsifying agent, dispersing agent, agent for imparting lubricity, agent for imparting hydrophilicity, agent for imparting oleophilicity, compatibilizer, cleansing agent, and so forth. They are useful in particular as a component of cosmetics for external application to the skin or hair and as a component of drugs for topical application to the skin.

Among the preceding, the following are useful as a component of cosmetics for external application to the skin or hair or as a component of drugs for topical application to the skin:

the polyether-modified organopolysiloxane represented by average unit formula (1), wherein $R^1$ therein is a monovalent hydrocarbyl group that does not contain an aliphatically unsaturated bond, W in the X in the organic group represented by general formula (3) is a monovalent hydrocarbyl group that does not contain an aliphatically unsaturated bond, Z is an alkyleneoxy group having 2 to 6 carbon atoms, n and m satisfy $0.9 \leq n/(n+m) \leq 1$, and Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond;

the polyether-modified organopolysiloxane represented by average structural formula (8), wherein W in the X in the organic group represented by genera formula (3) is a monovalent hydrocarbyl group that does not contain an aliphatically unsaturated bond, Z is an alkyleneoxy group having 2 to 6 carbon atoms, n and m satisfy $0.9 \leq n/(n+m) \leq 1$, and Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond;

the polyether-modified organopolysiloxane represented by average structural formula (10), wherein W in the X in the organic group represented by general formula (3) is a monovalent hydrocarbyl group that does not contain an aliphatically unsaturated bond, Z is an alkyleneoxy group having 2 to 6 carbon atoms, n and m satisfy $0.9 \leq n/(n+m) \leq 1$, and Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond;

the diorganopolysiloxane-polyether block copolymer having a main chain represented by general formula (13) or general formula (59), wherein $R^1$ therein is a monovalent hydrocarbyl group that does not contain an aliphatically unsaturated bond, W in the group X is a monovalent hydrocarbyl group that does not contain an aliphatically unsaturated bond, and Z is not present (that is, m=0);

the diorganopolysiloxane-polyether block copolymer represented by average structural formula (14), average structural formula (17), or average structural formula (60), wherein $R^1$ therein is a monovalent hydrocarbyl group that does not contain an aliphatically unsaturated bond, W in the group X is a monovalent hydrocarbyl group that does not contain an aliphatically unsaturated bond, and Z is not present (that is, m=0); and the diorganopolysiloxane-polyether block copolymer represented by average structural formula (19), wherein W in the group X is a monovalent hydrocarbyl group that does not contain an aliphatically unsaturated bond, Z is not present (that is, m=0), and Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond (the preceding are collectively designated as "(a) polyether-modified organopolysiloxane or diorganopolysiloxane-polyether block copolymer of the present invention"). In addition, two or more of the preceding may be used in combination.

In preferred embodiments of the polyether-modified organopolysiloxane or diorganopolysiloxane-polyether block copolymer (a) of the present invention, the monovalent hydrocarbyl group that does not contain an aliphatically unsaturated bond constituting $R^1$ is an alkyl group; Z is not present (that is, m=0); the divalent hydrocarbyl group having 2 to 20 carbon atoms that does not contain an aliphatically unsaturated bond constituting $R^4$ is an alkylene group having 2 to 20 carbon atoms; the group comprising said divalent hydrocarbyl group having an ether linkage therein is an alkyleneoxyalkylene group having 2 to 20 carbon atoms; $R^3$ in the organic group with general formula (3) is an alkylene or alkyleneoxyalkylene group having 2 to 20 carbon atoms; Y is hydrogen atom or an alkyl group having no more than 20 carbon atoms or a saturated aliphatic acyl group having no more than 20 carbon atoms and in particular is hydrogen atom; W in the group X is an alkyl group; and p is 1 or 2.

Viewed from the standpoint of obtaining an excellent balance among such properties as the capacity to lower the surface tension, permeation capacity, cleansing performance, emulsification capacity, solubilization capacity, and compatibility with water and organic solvents, the n in $—X_n—$ is preferably 2 to 70 and more preferably is 3 to 55.

In more preferred embodiments among the preceding from the standpoints of ease of synthesis and properties, the alkyl constituting $R^1$ is methyl; the alkylene constituting $R^3$ and $R^4$ is propylene or butylene; the alkyleneoxyalkylene constituting $R^3$, $R^4$, and $R^8$ is propyleneoxyethylene, ethyleneoxyethylene, propyleneoxypropylene, or a group with the aforementioned formula (20) or formula (21), and the alkyl that is W in the group X is an alkyl having 1 to 4 carbon atoms.

The amount of incorporation of the polyether-modified organopolysiloxane or diorganopolysiloxane-polyether block copolymer (a) of the present invention into a cosmetic may be selected as appropriate and suitable in accordance with such factors as the type of cosmetic and its properties, applications, intended use, and so forth; however, the range of 0.05 to 40 weight % of the cosmetic as a whole and the range of 0.1 to 20 weight % of the cosmetic as a whole may be taken as guidelines. The polyether-modified organopolysiloxane or diorganopolysiloxane-polyether block copolymer (a) of the present invention is also well suited for use as a component of drugs for topical application to the skin (referred to hereafter as a topical drug). In this case the amount of incorporation into the topical drug may be selected as appropriate and suitable in view of such factors as the type of topical drug and its properties, applications, intended use, and so forth; however, the range of 0.05 to 40 weight % of the topical drug as a whole and the range of 0.1 to 20 weight % of the topical drug as a whole may be taken as guidelines.

The cosmetic of the present invention may be any cosmetic whose properties are improved by the incorporation of the polyether-modified organopolysiloxane or diorganopolysiloxane-polyether block copolymer (a) of the present invention or by the incorporation of both the polyether-modified organopolysiloxane and the diorganopolysiloxane-polyether block copolymer (a) of the present invention, and the type of the cosmetic is not otherwise particularly limited. The cosmetic of the present invention can be exemplified by skin cosmetic products, such as skin cleansing products, skin care products, makeup cosmetic products, antiperspirant products, UV protective products, and so forth; by hair cosmetic products, such as hair cleansing products, hair styling products, hair dyeing products, hair maintenance products, hair rinse products, and so forth; by bath cosmetic products; and by perfumed water and colognes.

The aforementioned skin cosmetic can be used at various locations, such as on the scalp, face (including lips, eyebrows, and cheeks), fingers, nails, and entire body. This skin cosmetic can be specifically exemplified by skin cleansing products such as cleansing gels, cleansing creams, cleansing foams, cleansing milks, cleansing lotions, facial cleansing creams, eye make-up removers, facial cleansing foams, liquid whole-body soaps, hand soaps, gel soaps, solid soaps, facial rinses, body rinses, shaving creams, nail polish removers, anti-acne products, and so forth; skin care products such as skin creams, hot-oil scalp treatments, skin milks, milk lotions, emulsions, toilet waters, moisturizers, beauty liquids, facial compact powders, body powders, essences, shaving lotions, and so forth; makeup products such as foundations, makeup bases, white powders, face powders, lipsticks, lip creams, lip colors, lip glosses, eye shadows, eyeliners, eye creams, eyebrow pencils, eyelash cosmetic products, eyebrow cosmetics, eyebrow brushes, mascaras, rouges, cheek cosmetic products (cheek color, cheek rouge), nail polishes, toenail polishes, nail colors, nail lacquers, enamel removers, and so forth; deodorants and other antiperspirants; and UV protectants such as sunscreens, suntanning preparations (suntanning agents), and so forth.

The aforementioned hair cosmetics can be exemplified by hair cleansing agents, such as shampoos, shampoos with rinse, and so forth; hair styling products such as hair oils, hair curl retention agents, setting agents, hair creams, hair sprays, hair liquids, and so forth; hair coloring products such as hair dyes, hair color sprays, hair color rinses, hair color sticks, and so forth; hair maintenance products such as hair tonics, hair treatments, hair packs, and so forth; and hair rinses such as oil rinses, cream rinses, treatment rinses, and so forth. The bath cosmetic products are exemplified by bath oils, bath salts, and foam bath products.

The state and properties of the cosmetic of the present invention are not particularly limited and can be exemplified by liquids, W/O liquid emulsions, O/W liquid emulsions, W/O creams, O/W creams, pastes, gels, multilayered formulations, mousses, mists, sticks, solids, powders, fine granules, flakes, crushed stones, and so forth.

There are also no particular restrictions on containers used to hold the cosmetic of the present invention, and the containers can be exemplified by jars, pump cans, tubes, bottles, pressure spray containers, pressure-resistant aerosol containers, light-resistant containers, compact containers, metal cans, lipstick containers, dispensing containers, aerosol containers, partitioned containers with an outlet for discharging a mixed fluid, and so forth.

The cosmetic of the present invention contains the above-described polyether-modified organopolysiloxane or diorganopolysiloxane-polyether block copolymer (a) of the present invention as an essential component, and preferably additionally contains at least one other cosmetic component. This other cosmetic component can be (b) an oil, (c) a compound that contains an alcoholic hydroxyl group in the molecular structure, (d) water, (e) a powder and/or a colorant, (f) a water-soluble polymer, (g) a surfactant, (h) a silicone, (i) a UV protective component, (j) a salt, or (k) an antiseptic preservative, physiologically active component, oil-soluble gelling agent, pH adjuster, chelating agent, solvent, propellant, oxidation inhibitor, moisture-retention component, fragrance, and so forth. In addition to the aforementioned polyether-modified organopolysiloxane or diorganopolysiloxane-polyether block copolymer (a) of the present invention, the cosmetic of the present invention typically contains at least one selection from the group consisting of (b) an oil, (c) a compound that contain an alcoholic hydroxyl group in the molecular structure, and (d) water, and may contain at least one selection from the group consisting of (e) a powder and/or colorant, (f) a water-soluble polymer, (g) a surfactant, (h) a silicone, (i) a UV protective component, (j) a salt, and (k) an antiseptic preservative, physiologically active component, oil-soluble gelling agent, pH adjuster, chelating agent, solvent, propellant, oxidation inhibitor, moisture-retention component, fragrance, and so forth. While an excellent cosmetic of the present invention is obtained when the cosmetic contains just (a) polyether-modified organopolysiloxane or diorganopolysiloxane-polyether block copolymer of the present invention, (b) an oil, and (c) a compound that contains an alcoholic hydroxyl group in the molecular structure, an even more suitable cosmetic may be obtained by the additional incorporation of at least one selection from the group consisting of (d) water, (e) a powder and/or colorant, (f) a water-soluble polymer, (g) a surfactant, (h) a silicone, (i) a UV protective component, (j) a salt, and (k) an antiseptic preservative, physiologically active component, oil-soluble gelling agent, pH adjuster, chelating agent, solvent, propellant, oxidation inhibitor, moisture-retention component, fragrance, and so forth.

The oil (b) is incorporated, in correspondence to the formulation and type of the cosmetic, in order to improve the use sensation of the cosmetic, in order to improve the water repellency of the cosmetic, in order to impart moisture retention, and so forth. This oil (b) is an oil as used in the usual cosmetics and may be a liquid, semisolid, or solid. All or a portion of the oil is preferably a liquid at 5 to 100° C., and a liquid, semisolid, or solid (at room temperature in each case) oil is used as appropriate for the particular application.

The oil (b) is exemplified by animal and vegetable oils, semisynthetic oils, hydrocarbon oils, higher fatty acids, fatty acid ester oils, glyceride oils, fluorohydrocarbon oils, and fluoropolyether oils, wherein the oils normally used in cosmetics are preferred.

The animal and vegetable oils and the semisynthetic oils are exemplified by avocado oil, linseed oil, almond oil, ibota wax, *perilla* oil, olive oil, cacao butter, kapok wax, kaya oil, carnauba wax, cod liver oil, candelilla wax, beef tallow, bovine hoof oil, bovine bone fat, hardened beef tallow, apricot kernel oil, spermaceti wax, hardened oils, wheat germ oil, sesame oil, rice germ oil, rice bran oil, sugarcane wax, sasanqua oil, safflower oil, shea butter, paulownia oil, cinnamon oil, jojoba wax, shellac wax, turtle oil, soybean oil, tea seed oil, camellia oil, evening primrose oil, corn oil, lard, rapeseed oil, Japanese tung oil, rice bran wax, germ oil, horse fat, persic oil, palm oil, palm kernel oil, castor oil, hardened castor oil, the methyl esters of castor oil fatty acids, sunflower oil, grape seed oil, bayberry wax, jojoba oil, *macadamia* nut oil, yellow beeswax, mink oil, cottonseed oil, cotton wax, Japan wax, sumac kernel oil, montan wax, palm oil, hardened palm oil, cocofatty acid triglycerides, mutton tallow, peanut oil, lanolin, liquid lanolin, reduced lanolin, lanolin alcohol, hardened lanolin, lanolin acetate, isopropyl esters of lanolin fatty acids, hexyl laurate, POE lanolin alcohol ether, POE lanolin alcohol acetate, lanolin fatty acid polyethylene glycol, POE hydrogenated lanolin alcohol ether, and egg yolk oil, etc.

The hydrocarbon oils can be exemplified by ozokerite, squalane, squalene, ceresin, paraffin, paraffin wax, liquid paraffin, pristane, polyisobutylene, microcrystalline wax, vaseline, isododecane, isohexadecane, isohexapentacontahectane, and isopentane.

The higher fatty acids can be exemplified by lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid.

The ester oils can be exemplified by diisobutyl adipate, 2-hexyldecyl adipate, di-2-heptylundecyl adipate, N-alkylglycol monoisostearate, isocetyl isostearate, trimethylolpropane triisostearate, ethylene glycol di-2-ethylhexanoate, cetyl 2-ethylhexanoate, isocetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, isononyl isononanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, 2-ethylhexyl myristate, octyldodecyl myristate, 2-hexyldecyl myristate, myristyl myristate, hexyldecyl dimethyloctanoate, ethyl laurate, hexyl laurate, N-lauroyl L-glutamic acid/2-octyldodecyl ester, diisostearyl malate, and so forth.

The glyceride oils can be exemplified by glyceryl acetate, glyceryl triisooctanoate, glyceryl triisostearate, glyceryl triisopalmitate, glyceryl tri(caprylate caprate), glyceryl monostearate, glyceryl di-2-heptylundecanoate, glyceryl trimyristate, diglyceryl myristate isostearate, and so forth The fluorohydrocarbon oils can be exemplified by perfluorodecalin, perfluorooctane, and fluorinated pitch. Perfluoroalcohols are also examples.

Two or more types of these oils (b) can be used as necessary. The content of the oil (b) in the cosmetic of the present invention varies with the particular cosmetic formulation, but in general is 0.1 to 90.0 weight %. 1.0 to 50 weight % is preferred. The effects of the oil (b) in the cosmetic cannot be manifested at less than the cited lower limit, while the effect of the polyether-modified organopolysiloxane or diorganopolysiloxane-polyether block copolymer (a) of the present invention may, depending on the cosmetic, be inadequate at above the cited upper limit.

The compound (c) that contains an alcoholic hydroxyl group in the molecular structure is incorporated, in correspondence to the cosmetic type or cosmetic formulation, in order to improve the cosmetic's use sensation; impart a refreshing sensation, cooling sensation, moisture retention, and so forth; or as a highly human-safe solvent when a hydrophobic component is incorporated into the cosmetic. This component (c) can be exemplified by lower alcohols, sugars, sugar alcohols, and polyhydric alcohols, but may be any alcoholic hydroxy-bearing compound that is typically used in cosmetics and is not otherwise particularly limited.

Examples of preferred lower alcohols are alcohols having 2 to 5 carbon atoms. Specific examples are ethanol, isopropanol, butanol, and so forth.

The sugars can be exemplified by glucose, maltose, fructose, tetroses, and pentoses. The sugar alcohols produced by the hydrogenation (mainly catalytic reduction) of these sugars can be exemplified by sorbitol, maltose, maltitol, erythritol, xylitol, and lactitol.

The higher alcohols can be exemplified by lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, phytosterols, POE cholesterol ether, monostearyl glycerol ether (batyl alcohol), and monooleyl glyceryl ether (selachyl alcohol).

The polyhydric alcohols can be exemplified by polyhydric alcohols and polyols having 2 to 20 carbon atoms and are specifically exemplified by 1,2-ethylene glycol, 1,3-butanediol, 2-ethyl-1,3-hexanediol, 2, -diethyl-1,5-pentanediol, 2-butyl-2-ethyl-1,3-propanediol, glycerol, and polyethylene polyol.

Two or more of the compound (c) that contain an alcoholic hydroxyl group in the molecular structure can be used as necessary. The content in the cosmetic of the present invention of the compound (c) that contains an alcoholic hydroxyl group in the molecular structure will vary with the particular cosmetic formulation and the purpose of incorporating this component (c), but is generally 0.1 to 98 weight %. The effects of component (c) in the cosmetic cannot be manifested at less than the cited lower limit, while the effect of the polyether-modified organopolysiloxane or diorganopolysiloxane-polyether block copolymer (a) of the present invention may, depending on the cosmetic, be inadequate at above the cited upper limit.

The water (d) is incorporated in order, for example, to dissolve water-soluble components, emulsify oil components, moisten the cosmetic, and so forth. Examples are purified water, ion-exchanged water, and mineral water. Component (d) is an essential constituent component when the cosmetic of the present invention is a water-based cosmetic such as a liquid emulsion, but need not be incorporated when the cosmetic is a non-water-based cosmetic, such as a foundation or lipstick. The content in the cosmetic of the present invention is 0 to 90.0 weight % and is increased or decreased in accordance with the type and state of the cosmetic.

The powder and/or colorant as component (e) is incorporated in order, for example, to thicken, extend, particulate, or color the cosmetic. Any powder and/or colorant ordinarily used in cosmetics can be used, regardless of the shape (spherical, cylindrical, acicular, plate shaped, irregular, spindle shaped, and so forth), the particle diameter (fumed, microparticulate, pigment grade), and the particle structure (porous, nonporous, etc.). When this powder and/or colorant is incorporated as a pigment, at least one selection from inorganic pigment powders, organic pigment powders, and resin powders, in each case with an average particle diameter in the range from 1 nm to 20 µm, is preferably incorporated.

The powder and/or colorant (e) can be exemplified by inorganic powders, organic powders, surface-active metal salt powders (metal soaps), colored pigments, pearlescent pigments, and metal powder pigments. Composites of these pigments are also examples. The inorganic powder can be exemplified by titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic silica, phlogopite, rose mica, biotite, lepidolite, silicic acid, silicic anhydride (dry-method silica, wet-method silica), colloidal silica, aluminum silicate, magnesium silicate, aluminum magnesium silicate, sodium silicate, sodium magnesium silicate, calcium silicate, barium silicate, strontium silicate, metal salts of tungstic acid, hydroxyapatite, vermiculite, Higilite, bentonite, montmorillonite, hectorite, organically modified clay minerals (organobentonite, organomontmorillonite, organohectorite, and so forth), zeolite, ceramic powders, calcium secondary phosphate, alumina, aluminum hydroxide, boron nitride, and so forth.

The organic powders can be exemplified by powders of thermoplastic resins such as polyamides (e.g., nylon 6, nylon 66, nylon 12, and so forth), polyesters, polyethylenes, polypropylenes, polystyrenes, polyurethanes, polycarbonate resins, fluororesins such as polytetrafluoroethylene, polymethyl methacrylate, styrene.acrylic acid copolymers, divinylbenzene.styrene copolymers, and so forth; powders of thermosetting resins such as unsaturated polyester resins, urea resins, phenolic resins, thermosetting acrylic resins, melamine resins, epoxy resins, benzoguanamine, polymethylbenzoguanamine, and so forth; and powders of natural materials such as natural fibers, cellulose, silk, wool, starch, lauroylysine, and so forth.

The surface-active metal salt powders can be exemplified by powders of zinc stearate, aluminum stearate, calcium stearate, magnesium stearate, zinc myristate, magnesium myristate, zinc cetyl phosphate, calcium cetyl phosphate, sodium cetyl phosphate, and so forth.

The colored pigments can be exemplified by inorganic red pigments such as iron oxide, iron hydroxide, and iron titanate; inorganic brown pigments such as γ-iron oxide and so forth; inorganic yellow pigments such as iron oxide yellow, ocher, and so forth; inorganic black pigments such as iron oxide black, carbon black, and so forth; inorganic purple pigments such as magnesium violet, cobalt violet, and so forth; inorganic green pigments such as chromium hydroxide, chromium oxide, cobalt oxide, cobalt titanate, and so forth; inorganic blue pigments such as Prussian blue, ultramarine blue, and so forth; lakes prepared from tar dyes such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, and so forth; and lakes prepared from natural dyes such as carminic acid, laccaic acid, carthamin, brazilin, crocin, and so forth.

The pearlescent pigments can be exemplified by titanium oxide-coated mica, bismuth oxychloride, titanium oxide-coated bismuth oxychloride, titanium oxide-coated talc, fish scale flake, titanium oxide-coated colored mica, and so forth. The metal powder pigments can be exemplified by the powders of metals such as aluminum, gold, silver, copper, platinum, stainless steel, and so forth.

It is particularly preferred that the powder and/or colorant as component (d) be subjected to a treatment that imparts water repellency. The polyether-modified organopolysiloxane or diorganopolysiloxane-polyether block copolymer (a) of the present invention has an affinity for such water-repellent pigments, which has the effect of stopping the loss of uniformity and impaired appearance by the cosmetic that are the results of pigment migration. This can improve the keeping qualities and durability of the cosmetic. It also makes possible an improvement in the sebum resistance of the cosmetic.

The water repellency treatment for the powder and/or colorant can be exemplified by an organosiloxane treatment, for example, a methylhydrogenpolysiloxane treatment, silicone resin treatment, silicone gum treatment, acrylic-modified silicone treatment, fluorinated silicone treatment, and so forth; a silane treatment, for example, a silane coupling agent treatment, alkylalkoxysilane treatment, alkylchlorosilane treatment, hexamethyldisilazane treatment, and so forth; treatment with a fluorinated compound, such as treatment with a perfluoroalkylalkoxysilane, perfluoroalkyl phosphate ester salt, perfluoropolyether, and so forth; treatment with an amino acid such as N-lauroyl-L-lysine and so forth; treatment with an oil such as a squalane treatment; and an acrylic treatment such as treatment with an alkyl acrylate. Two or more of these treatments may be used in combination.

Two or more of these powders and/or colorants as component (d) (including the species that have been subjected to a treatment that imparts water repellency) can be used as necessary. The amount of incorporation varies broadly as a function of the particular cosmetic formulation, but ordinarily is generally 0.1 to 50 weight % and preferably 0.5 to 30 weight %, in each case with reference to the total quantity of the cosmetic. Among the cited powders, polyethylene powder, polypropylene powder, polytetrafluoroethylene powder, polyurethane powder, and so forth improve the use sensation and temporal stability of the cosmetic.

The water-soluble polymer as component (f) is incorporated in order to thicken the cosmetic, improve its use sensation, and so forth. Any of the amphoteric, cationic, anionic, and nonionic water-soluble polymers and water-swellable clay minerals that are typically used in cosmetics can be used as this component, and two or more water-soluble polymers can be used in combination.

The amphoteric water-soluble polymers can be exemplified by amphoteric starch, dimethyldiallylammonium chloride derivatives (e.g., acrylamide.acrylic acid. dimethyldiallylammonium chloride copolymers, acrylic acid.dimethyldiallylammonium chloride copolymers) and methacrylic acid derivatives (e.g., polymethacryloylethyldimethylbetaine, N-methacryloyloxyethyl-N,N-dimethylammonium-α-methylcarboxybetaine. alkyl methacrylate copolymer, and so forth).

The cationic water-soluble polymers can be exemplified by quaternary nitrogen-modified polysaccharides (e.g., cationically modified cellulose, cationically modified hydroxyethyl cellulose, cationically modified guar gum, cationically modified locust bean gum, cationically modified starch, and so forth), dimethyldiallylammonium chloride derivatives (e.g., dimethyldiallylammonium chloride.acrylamide copolymers, polydimethylmethylenepiperidinium chloride, and so forth), vinylpyrrolidone derivatives (e.g., vinylpyrrolidone.dimethylaminoethyl methacrylate copolymer salts, vinylpyrrolidone methacrylamidopropyltrimethylammonium chloride copolymers, vinylpyrrolidone. methylvinylimidazolium chloride copolymers, and so forth), methacrylic acid derivatives (e.g., methacryloylethyldimethylbetaine.methacryloylethyltrimethylammonium chloride. 2-hydroxyethyl methacrylate copolymers, methacryloylethyldimethylbetaine.methacryloylethyltrimethylammonium Chloride.methoxypolyethylene glycol methacrylate copolymers, and so forth).

The anionic water-soluble polymer can be exemplified by water-soluble polymers of aliphatic carboxylic acids and their metal salts, for example, polyacrylic acid and its alkali metal salts, polymethacrylic acid and its alkali metal salts, hyaluronic acid and its alkali metal salts, acetylated hyaluronic acid and its alkali metal salts, hydrolyzates of methyl vinyl ether.maleic anhydride copolymers, and so forth, and by carboxymethyl cellulose and its alkali metal salts, methyl vinyl ether.maleate hemiester copolymers, alkanolamine solutions of acrylic resins, and carboxyvinyl polymers.

The nonionic water-soluble polymer can be exemplified by polyvinylpyrrolidone, high degree of polymerization polyethylene glycol, vinylpyrrolidone/vinyl acetate copolymers, vinylpyrrolidone/dimethylaminoethyl methacrylate copolymers, and vinylcaprolactam/vinylpyrrolidone/dimethylaminoethyl methacrylate copolymers, and also by natural polymer compounds such as cellulose and derivatives thereof (e.g., methyl cellulose, ethyl cellulose, hydroxyethyl cellulose, hydroxypropyl cellulose, carboxymethyl cellulose), keratin and collagen and derivatives thereof, calcium alginate, pullulan, agar, gelatin, tamarind seed polysaccharides, xanthan gum, carrageenan, high-methoxyl pectin, low-methoxyl pectin, guar gum, pectin, gum arabic, crystalline cellulose, arabinogalactan, karaya gum, tragacanth gum, alginic acid, albumin, casein, curdlan, gellan gum, dextran, quince seed gum, traganth gum, chitin. chitosan derivatives, starch (rice, corn, potato, wheat, and so forth), keratin and collagen and derivatives thereof, and so forth.

The water-swellable clay minerals may be natural or synthetic. A typical example is colloidal aluminum silicate with a three-layer structure, for example, with formula (11)

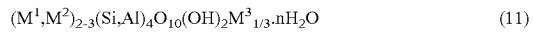
$$(M^1,M^2)_{2-3}(Si,Al)_4O_{10}(OH)_2M^3{}_{1/3}.nH_2O \qquad (11)$$

(wherein $M^1$ is Al, Fe(III), Mn(III), or Cr(III); $M^2$ is Mg, Fe(II), Ni, Zn, or Li; and $M^3$ is K, Na, or Ca). Examples are bentonite, montmorillonite, beidellite, nontronite, saponite, hectorite, organically modified clay minerals (organobentonite, organomontmorillonite, organohectorite, and so forth), and magnesium aluminum silicate.

The amount of incorporation of this component (f) varies with the particular cosmetic formulation, but is preferably 0.01 to 25.0 weight % with reference to the total quantity of the cosmetic product. The thickening performance and the film-forming performance are inadequate when the quantity of incorporation is less than the cited lower limit; the stickiness increases when the cited upper limit is exceeded, which is generally undesirable for a cosmetic.

The surfactant as component (g) is incorporated, in correspondence to the particular type and formulation of the cosmetic, in order to emulsify an oleophilic component in water, to bring about a uniform dispersion of various components of the cosmetic, to induce the appearance of or improve the cleansing performance of the cosmetic, and so forth.

This component (g) can be an anionic surfactant, a cationic surfactant, a nonionic surfactant, an amphoteric surfactant, or a semipolar surfactant. While the polyether-modified organopolysiloxane or diorganopolysiloxane-polyether block copolymer (a) of the present invention does exhibit a surface-active performance, the cleansing activity and the blending stability of the cosmetic can be improved by the additional incorporation of the surfactant (g).

The anionic surfactant can be exemplified by saturated and unsaturated fatty acid salts (e.g., sodium laurate, sodium stearate, sodium oleate, sodium linolenate, and so forth), alkyl sulfate salts, alkylbenzenesulfonic acids (e.g., hexylbenzenesulfonic acid, octylbenzenesulfonic acid, dodecylbenzenesulfonic acid, and so forth) and their salts, polyoxyalkylene alkyl ether sulfate salts, polyoxyalkylene alkenyl ether sulfate salts, polyoxyethylene alkyl sulfate ester salts, alkyl sulfosuccinate salts, salts of alkyl esters of polyoxyalkylenesulfosuccinic acid, polyoxyalkylene alkylphenyl ether sulfate salts, alkanesulfonic acid salts, salts of alkyl esters of polyoxyalkylene-modified silicone sulfosuccinic acid, polyoxyalkylene-modified silicone alkyl sulfate salts, polyoxyalkylene-modified silicone sulfate ester salts, polyoxyalkylene-modified silicone pentenyl phosphate salts, polyoxyalkylene-modified silicone phosphate ester salts, octyltrimethylammonium hydroxide, dodecyltrimethylammonium hydroxide, alkylsulfonate, polyoxyethylene alkylphenyl ether sulfate salts, polyoxyalkylene alkyl ether acetate salts, alkyl phosphate salts, polyoxyalkylene alkyl ether phosphate salts, acylglutamate salts, α-acylsulfonate salts, alkylsulfonate salts, alkylallylsulfonate salts, α-olefinsulfonate salts, alkylnaphthalenesulfonate salts, alkanesulfonate salts, alkyl or alkenyl sulfate salts, alkylamide sulfate salts, alkyl or alkenyl phosphate salts, alkylamide phosphate salts, alkyloylalkyltaurine salts, N-acylamino acid salts, sulfosuccinate salts, alkyl ether carboxylic acid salts, amide ether carboxylic acid salts, α-sulfofatty acid ester salts, alanine derivatives, glycine derivatives, and arginine derivatives. The salts can be exemplified by alkali metal salts such as the sodium salt and so forth, alkaline-earth metal salts such as the magnesium salt and so forth, alkanolamine salts such as the triethanolamine salt and so forth, and the ammonium salt.

The cationic surfactants are exemplified alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, benzalkonium chloride, alkylbenzalkonium chloride, alkyldimethylbenzalkonium chloride, benzethonium chloride, stearyldimethylbenzylammonium chloride, lanolin-derived quaternary ammonium salts, the diethylaminoethylamide of stearic acid, the dimethylaminopropylamide of stearic acid, behenamidopropyldimethylhydroxypropylammonium chloride, stearoylcolaminoformylmethylpyridinium chloride, cetylpyridinium chloride, tall oil alkylbenzylhydroxyethylimidazolinium chloride, and benzylammonium salts.

The nonionic surfactants can be exemplified by polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hydrogenated) castor oils, polyoxyalkylene alkylphenols, polyoxyalkylene alkylphenyl ethers, polyoxyalkylene phenylphenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycols, diethylene glycol, polyoxyethylene.polyoxypropylene block polymers, alkyl polyoxyethylene.polyoxypropylene block polymer ethers, fluorosurfactants, polyglyceryl-modified organopolysiloxanes, glyceryl-modified organopolysiloxanes, and polyoxyalkylene-modified organopolysiloxanes. However, nonionic surfactants that have a polyoxyalkylene chain exhibit a poor oxidation resistance and should be used only in very small amounts.

The amphoteric surfactants can be exemplified by imidazoline types, amidobetaine types, alkylbetaine types, alkylamidobetaine types, alkylsulfobetaine types, amidosulfobetaine types, hydroxysulfobetaine types, carbobetaine types, phosphobetaine types, aminocarboxylic acid types, and amidoamino acid types. Specific examples are as follows: imidazoline-type amphoteric surfactants such as sodium 2-undecyl-N,N,N-(hydroxyethylcarboxymethyl)-2-imidazoline, disodium salt of 2-cocoyl-2-imidazolinium hydroxide-1-carboxyethyloxy, and so forth; alkylbetaine-type amphoteric surfactants such as lauryldimethylaminoacetic acid betaine, myristylbetaine, and so forth; amidobetaine-type amphoteric surfactants such as cocofatty acid amidopropyldimethylaminoacetic acid betaine, palm kernel oil fatty acid amidopropyldimethylaminoacetic acid betaine, beef tallow fatty acid amidopropyldimethylaminoacetic acid betaine, hydrogenated beef tallow fatty acid amidopropyldimethylaminoacetic acid betaine, lauramidopropyldimethylaminoacetic acid betaine, myristamidopropyldimethylaminoacetic acid betaine, palmitamidopropyldimethylaminoacetic acid betaine, stearamidopropyldimethylaminoacetic acid betaine, oleamidopropyldimethylaminoacetic acid betaine, and so forth; alkylsulfobetaine-type amphoteric surfactants such as cocofatty acid dimethylsulfopropylbetaine and so forth; alkylhydroxysulfobetaine-type amphoteric surfactants such as lauryldimethylaminohydroxysulfobetaine and so forth; phosphobetaine-type amphoteric surfactants such as laurylhydroxyphosphobetaine and so forth; amidoamino acid-type amphoteric surfactants such as sodium N-lauroyl-N'-hydroxyethyl-N'-carboxymethylethylenediamine, sodium N-oleoyl-N'-hydroxyethyl-N'-carboxymethylethylenediamine, sodium N-cocoyl-N'-hydroxyethyl-N'-carboxymethylethylenediamine, potassium N-lauroyl-N'-hydroxyethyl-N'-carboxymethylethylenediamine, potassium N-oleoyl-N'-hydroxyethyl-N'-carboxymethylethylenediamine, sodium N-lauroyl-N-hydroxyethyl-N'-carboxymethylethylenediamine, sodium N-oleoyl-N-hydroxyethyl-N'-carboxymethylethylenediamine, sodium N-cocoyl-N-hydroxyethyl-N'-carboxymethylethylenediamine, monosodium N-lauroyl-N-hydroxyethyl-N',N'-dicarboxymethylethylenediamine, monosodium N-oleoyl-N-hydroxyethyl-N',N'-dicarboxymethylethylenediamine, monosodium N-cocoyl-N-hydroxyethyl-N',N'-dicarboxymethylethylenediamine, disodium N-lauroyl-N-hydroxyethyl-N',N'-dicarboxymethylethylenediamine, disodium N-oleoyl-N-hydroxyethyl-N',N'-dicarboxymethylethylenediamine, disodium N-cocoyl-N-hydroxyethyl-N',N'-dicarboxymethylethylenediamine, and so forth; and also dimethylsiloxane.methyl[3-[3-{N-carboxylatomethyl-N-(2-hydroxyethyl)-N-methylammonio}-2-hydroxypropoxy]propyl]siloxane copolymers, and sulfobetaine group-containing polysiloxanes.

The semipolar surfactant can be exemplified by alkylamine oxide-type surfactants, alkylamine oxides, alkylamidoamine oxides, and alkylhydroxyamine oxides, wherein the use is preferred of alkyldimethylamine oxides having 10 to 18 carbon atoms and alkoxyethyldihydroxyethylamine oxides having 8 to 18 carbon atoms. Specific examples are dodecyldimethylamine oxide, dimethyloctylamine oxide, diethyldecylamine oxide, bis(2-hydroxyethyl)dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, cocofatty acid alkyldimethylamine oxide, caprylamidopropyldimethylamine oxide, capramidopropyldimethylamine oxide, lauramidopropyldimethylamine oxide, myristamidopropyldimethylamine oxide, palmitamidopropyldimethylamine oxide, stearamidopropyldimethylamine oxide, isostearamidopropyldimethylamine oxide, oleamidopropyldimethylamine oxide, ricinoleamidopropyldimethylamine oxide, 12-hydroxystearamidopropyldimethylamine oxide, cocofatty acid amidopropyldimethylamine oxide, palm kernel oil fatty acid amidopropyldimethylamine oxide, castor oil fatty acid amidopropyldimethylamine oxide, lauramidoethyldimethylamine oxide, myristamidoethyldimethylamine oxide, cocofatty acid amidoethyldimethylamine oxide, lauramidoethyldiethylamine oxide, myristamidoethyldiethylamine oxide, cocofatty acid amidoethyldiethylamine oxide, lauramidoethyldihydroxyethylamine oxide, myristamidoethyldihydroxyethylamine oxide, and cocofatty acid amidoethyldihydroxyethylamine oxide.

Skin cleansers (e.g., cleansing gels, cleansing creams, cleansing milks, cleansing lotions, facial cleansers), hair cleansers (e.g., shampoos), hair rinses, and so forth that incorporate the polyether-modified organopolysiloxane or diorganopolysiloxane-polyether block copolymer (a) of the present invention and the surfactant as component (g) exhibit an excellent cleansing capacity for the skin and hair and have the advantage of providing a post-washing sensation that is refreshing without being sticky. The amount of incorporation of this component (g) is preferably 1 to 20 weight % and more preferably 0.5 to 10 weight %, in each case with reference to the total quantity of the cosmetic.

The silicone (h) is a component that is incorporated in order to improve various properties of the cosmetic, and (h1) silicone oils, (h2) silicone gums, (h3) silicone resins, (h4) silicone rubber powders, (h5) crosslinked silicone gels and pastes, and (h6) silicone-modified organic polymers are examples of this component as applied to cosmetic products. The silicone (h) of course does not fall within the scope of component (a). The cosmetic of the present invention may contain at least one or two or more of these silicones in correspondence to the particular type and formulation of the cosmetic.

The silicone oil (h1) is incorporated in order to impart, inter alia, slipperiness, lubricity, water repellency, and oleophilicity to the cosmetic. It is generally a liquid at ambient temperature, and its molecular structure may be straight chain, cyclic, or branched. While this silicone oil may be an organopolysiloxane that has functional groups, such as alkyl, it of course does not fall within the scope of component (a).

The silicone oil can be exemplified by the following, in each case which is a liquid at ambient temperature: straight chain organopolysiloxane such as straight chain dimethylpolysiloxane, straight chain methylphenylpolysiloxane, straight chain methylhydrogenpolysiloxane, straight chain dimethylsiloxane.methylphenylsiloxane copolymer, and so forth; cyclic organopolysiloxanes such as octamethylcyclotetrasiloxane, decamethylcyclopentasiloxane, dodecamethylcyclohexasiloxane, tetramethyltetrahydrogencyclotetrasiloxane, tetramethyltetraphenylcyclotetrasiloxane, and so forth; branched organopolysiloxanes such as branched methylpolysiloxane, branched methylphenylpolysiloxane, and so forth; and organomodified silicones such as alkyl-modified organopolysiloxane, acryl-modified organopolysiloxane, sugar-modified organopolysiloxane, epoxy-modified organopolysiloxane, carboxy-modified organopolysiloxane, amino-modified organopolysiloxane, higher fatty acid-modified organopolysiloxane, fluorine-modified organopolysiloxane, and so forth. Among these silicone oils, low degree of polymerization, straight chain dimethylpolysiloxanes, octamethylcyclotetrasiloxane, decamethylcyclopentasiloxane, dodecamethylcyclohexasiloxane, and tetramethyltetrahydrogencyclotetrasiloxane offer the advantage, due to their volatility, of being able to impart a cool, refreshing sensation to the cosmetic.

The silicone gum (h2) is incorporated in order to impart, inter alia, slipperiness, lubricity, water repellency, oleophilicity, and water resistance to the cosmetic. It is generally a gum at ambient temperature, has an ultrahigh degree of polymerization, and has a straight chain molecular structure. This silicone gum (h2) is preferably a straight chain dimethylpolysiloxane that has an ultrahigh degree of polymerization or a straight chain diorganopolysiloxane given by the following general formula

$(CH_3)_3SiO\{(CH_3)_2SiO\}_a\{(CH_3)RSiO\}_bSi(CH_3)_3$ wherein R is a group selected from the group consisting of phenyl, an alkenyl having 2 to 8 carbon atoms, an alkyl having 6 to 20 carbon atoms, an aminoalkyl having 3 to 15 carbon atoms, a perfluoroalkyl having 3 to 15 carbon atoms (for example, 3,3,3-trifluoropropyl), groups represented by $HOOC(CH_2)_n$— (wherein n is an integer from 2 to 20), and an alkyl having 3 to 15 carbon atoms containing a quaternary ammonium salt group; a is 1 to 5000; b is 1 to 5000; and a+b is 2,500 to 25,000. The silicone gum may be incorporated as a cosmetic component in the form of a solution in the above-described component (h1), for example, a cyclic dimethylsiloxane solution or a straight chain dimethylsiloxane solution.

The silicone resin (h3) is incorporated in order to improve, inter alia, the use sensation, water resistance, and sebum resistance of the cosmetic. Insofar as the objects of the present invention are not impaired, any silicone resin ordinarily used in cosmetics can be used as the silicone resin under consideration. This silicone resin may be a solid, semisolid, or liquid at ambient temperature, and may have a branched, network, or cage molecular structure. It is preferably oil soluble and preferably is soluble in octamethyltetrasiloxane (also known as D4), decamethylcyclopentasiloxane (also known as D5), or a mixture thereof.

Siloxane units constituting the silicone resin encompass $(R^1)_3SiO_{1/2}$ (M unit), $(R^1)_2SiO_{2/2}$ (D unit), $(R^1)SiO_{3/2}$ (T unit), and $SiO_{4/2}$ (Q unit) (wherein $R^1$ is a monovalent hydrocarbyl group or a monovalent fluorohydrocarbyl group). Examples of how these siloxane units may be combined are as follows: a silicone resin comprising only $(R^1)SiO_{3/2}$; a silicone resin comprising $(R^1)_3SiO_{1/2}$ and $(R^1)SiO_{3/2}$ (MT resin); a silicone resin comprising $(R^1)_3SiO_{1/2}$, $(R^1)_2SiO_{2/2}$, and $(R^1)SiO_{3/2}$ (MDT resin); a silicone resin comprising $(R^1)_3 SiO_{1/2}$, $(R^1)_2SiO_{2/2}$, and $SiO_{4/2}$ (MDQ resin); a silicone resin comprising $(R^1)_2SiO_{2/2}$ and $(R^1)SiO_{3/2}$ (DT resin); a silicone resin comprising $(R^1)_3SiO_{1/2}$ and $SiO_{4/2}$ (MQ resin); a silicone resin comprising $(R^1)_3SiO_{1/2}$, $(R^1)SiO_{3/2}$, and $SiO_{4/2}$ (MTQ resin); a silicone resin comprising $(R^1)_3SiO_{1/2}$, $(R^1)_2SiO_{2/2}$, $(R^1)SiO_{3/2}$, and $SiO_{4/2}$ (MDTQ resin); a silicone resin comprising $(R^1)SiO_{3/2}$ and $SiO_{4/2}$ (TQ resin); and a silicone resin comprising $(R^1)_2SiO_{2/2}$, $(R^1)SiO_{3/2}$, and $SiO_{4/2}$ (DTQ resin). $R^1$ here can be exemplified by alkyl, aralkyl, phenyl, and vinyl. The alkyl is exemplified as for the alkyl described for $R^1$ in general formula (1) and these examples are preferred, wherein methyl is most preferred. The alkenyl is exemplified as for the double bond-terminated alkenyl described for R in general formula (7) and these examples are preferred, wherein vinyl is most preferred. The aralkyl is exemplified as for the aralkyl described for $R^1$ in general formula (1) and these examples are preferred. The monovalent fluorohydrocarbyl is exemplified by perfluoroalkyl and fluorinated phenyl.

This silicone resin can be incorporated by itself into the cosmetic; however, since mixing with the other components is facilitated when the silicone resin is converted into a solution or paste by dissolution or swelling in a volatile silicone oil (for example, a cyclic dimethyloligosiloxane), a volatile hydrocarbon oil, a nonvolatile silicone oil (for example, a straight chain dimethylpolysiloxane), or a nonvolatile hydrocarbon oil, this latter approach is preferred. Specific examples in this regard are a solution or a paste of a methylpolysiloxane resin or trimethylsiloxysilicic acid yielded by a volatile cyclic dimethylsiloxane or a nonvolatile straight chain dimethylpolysiloxane.

The amount of silicone resin incorporation is preferably 0.1 to 20 weight % and more preferably is 1 to 10 weight %, in each case with reference to the total quantity of the cosmetic. In order to obtain a cosmetic that has a relatively higher adhesiveness for the skin, a composition comprising 100 weight parts of the polyether-modified organopolysiloxane or diorganopolysiloxane-polyether block copolymer (a) of the present invention and 50 to 500 weight parts of the silicone resin is preferably used.

The silicone rubber powder (h4) is incorporated in order to improve the springiness of the cosmetic and to improve, inter alia, its use sensation, water resistance, and resistance to sebum. In the present context, the silicone rubber powder refers to a solid, rubbery elastic powder that is the crosslinked product from a straight chain organopolysiloxane or a lightly branched organopolysiloxane. The shape of the silicone rubber powder may be spherical, elliptical or oval, flat, irregular, and so forth. Spherical is preferred from the standpoint of the use sensation and mixability with the other components. The particle diameter is not particularly limited; however, the primary particle diameter as obtained by observation with an electron microscope or the average primary particle diameter measured by laser diffraction/scattering is preferably in the range of 0.1 to 50 μm. With regard to the hardness of the silicon rubber powder, the hardness using a JIS Type A durometer is preferably 0 to 80 and more preferably is 0 to 65.

The silicone rubber powder can be produced, for example, by preparing a curable composition comprising diorganopolysiloxane having at least two vinyl groups (for example, dimethylpolysiloxane endblocked at both terminals by vinyl groups), organohydrogenpolysiloxane (for example, methylhydrogenpolysiloxane), and a platinum-type catalyst (for example, chloroplatinic acid); emulsifying or dispersing this curable composition in water; and heating in order to bring about curing in a particulate form. Or, production can be carried out by spraying the cited curable composition into a hot gas in order to effect curing in a particulate form. This curable composition may also contain a reinforcing filler such as fumed silica or wet-method silica. The silicone rubber powder may also be prepared using a polymer that has at least two vinylic reactive moieties in the molecule (e.g., diene having aliphatic double bonds at both terminals, polyoxyalkylene diallyl ether, glycerol triallyl ether, polyoxyalkylated glycerol triallyl ether, trimethylolpropane triallyl ether, polyoxyalkylated trimethylolpropane triallyl ether, and so forth) rather than the diorganopolysiloxane having at least two vinyl groups.

Such silicone rubber powders are described, for example, in Japanese Unexamined Patent Application Publication Nos. Hei 02-243612, Hei 08-012545, Hei 08-012546, Hei 08-012524, Hei 09-241511, Hei 10-036219, Hei 11-193331, and 2000-281523. Commercial products include Trefil E series (e.g., Trefil E-505, Trefil E-506, Trefil E-507, Trefil E-508, and so forth) available from Dow Corning Toray Co., Ltd.; these correspond to the crosslinked silicone powders listed in the "Standards for Cosmetic Ingredients".

These silicone rubber powders may be subjected to a surface treatment. This surface treatment can be exemplified by treatment with methylhydrogenpolysiloxane, treatment with dimethylpolysiloxane, treatment with silicone resin micropowder, treatment with silane coupling agent, treatment with fumed silica, treatment with perfluoroalkylalkoxysilane, treatment with a metal soap, and surface treatment using a perfluoroalkyl phosphate ester salt.

The silicone rubber powder may be directly mixed or blended with the other components, or may be used to produce the cosmetic after conversion of the silicone rubber powder into a dispersion by dispersion in a liquid (e.g., water, ester oil, silicone oil, hydrocarbon oil, higher alcohol, vegetable oil, animal oil, and so forth) or into a mixture (e.g., paste, cream, granule, and so forth) with an oil (e.g., ester oil, silicone oil, hydrocarbon oil, higher alcohol, vegetable oil, animal oil, and so forth).

Spherical silicone rubber powders also frequently have particle diameters in excess of 10 μm and as a result have been difficult to fix on the skin; however, their use in combination with the polyether-modified organopolysiloxane or diorganopolysiloxane-polyether block copolymer (a) of the present invention accrues the advantage of enabling the formation of a more stable coating on the skin surface. Furthermore, while these silicone rubber powders scatter light, their incorporation in combination with the polyether-modified organopolysiloxane or diorganopolysiloxane-polyether block copolymer (a) of the present invention improves their dispersibility and attachability onto the skin and offers the advantage of improving the cosmetic coating's luster and durability on the skin in comparison to the absence of this combination.

The amount of silicone rubber powder incorporation varies with the type and properties of the cosmetic and the properties that are to be improved by the incorporation of the silicone rubber powder and thus is not particularly limited, but 0.1 to 30 weight % of the cosmetic is preferred. At below this lower limit, there is little improvement in the properties and, when the cosmetic is coated on a region of the body, the coated surface exhibits a weak water-sliding behavior and the coating is easily disrupted by contact with water. When the cited upper limit is exceeded, the properties inherent to the cosmetic itself are lost, and, while an excellent water-sliding behavior is exhibited, the physical strength of the coating ends up being reduced and the coating becomes relatively weak with respect to, for example, contact.

The crosslinked silicone gel or paste (h5) is a paste or gel composition yielded by swelling a crosslinked organopolysiloxane with a silicone oil or hydrocarbon oil, and is incorporated in order to improve the cosmetic's stability, use sensation, luster, water repellency, resistance to sebum, and so forth. The crosslinked organopolysiloxane for this purpose can be exemplified by condensation products from methylhydrogenpolysiloxanes; the aforementioned silicone rubber powders; the nonspherical cured products from curable compositions comprising a diorganopolysiloxane having at least two vinyl groups (for example, a dimethylpolysiloxane endblocked at both terminals by vinyl groups), an organohydrogenpolysiloxane (for example, methylhydrogenpolysiloxane), and a platinum-type catalyst (for example, chloroplatinic acid); and nonspherical cured products from curable compositions comprising a diene having an aliphatic double bond at both terminals or a polyoxyalkylene diallyl ether, an organohydrogenpolysiloxane (for example, methylhydrogenpolysiloxane), and a platinum-type catalyst (for example, chloroplatinic acid).

Also useful as the crosslinked silicone gels and pastes are the gel and paste compositions afforded by curing—wherein said curing is effected in a silicone oil or hydrocarbon oil—a curable composition comprising a diorganopolysiloxane having at least two vinyl groups (for example, a dimethylpolysiloxane endblocked at both terminals by vinyl), a diene having an aliphatic double bond at both terminals, or a polyoxyalkylene diallyl ether; an organohydrogenpolysiloxane (for example, methylhydrogenpolysiloxane); and platinum-type catalyst (for example, chloroplatinic acid).

The silicone oil used for this purpose can be exemplified by cyclic organosiloxanes such as octamethylcyclotetrasiloxane, decamethylcyclopentasiloxane, dodecamethylcyclohexasiloxane, tetramethyltetraphenylcyclotetrasiloxane, and so forth and by straight chain and lightly branched dimethylpolysiloxanes having a low degree of polymerization. The hydrocarbon oil can be exemplified by isododecane, isohexadecane, and isohexapentacontahectane.

Crosslinked silicone gels and pastes that are available as commercial products include DC9040 (gelled with silicone oil), DC9045 (gelled with cyclic silicone oil), DC9041 (made into a paste with a silicone oil), DC8040 (made into a paste with a hydrocarbon oil), and DC9011 (polyoxyalkylene chain-functional crosslinked organopolysiloxane dispersed in a silicone oil), all from Dow Corning Corporation.

The amount of incorporation of the crosslinked gel or paste (h5) varies as a function of the particular cosmetic formulation, but is preferably 0.01 to 40 weight % and particularly preferably is 0.1 to 30 weight %, in each case with reference to the total amount of the cosmetic.

The silicone-modified organic polymer (h6) is incorporated, inter alia, to improve the cosmetic's use sensation and surface protective behavior. The silicone-modified organic polymer can be exemplified by polydimethylsiloxane-grafted acrylate-type polymers (refer to Japanese Unexamined Patent Application Publication No. Hei 07-196449), carboxysiloxane dendrimer-grafted vinylic polymers (refer to Japanese Unexamined Patent Application Publication Nos. 2000-063225 and 2003-226611), and polydimethylsiloxane-grafted and branched carbosiloxane dendrimer-grafted acrylic copolymers that contain in the molecule at least one selection from the group consisting of alkyl carboxylate esters, pyrrolidone moiety, long-chain alkyl moieties, polyoxyalkylene moieties and fluoroalkyl moieties and anionic moieties such as carboxylic acid and so forth.

The UV protectant (i) is incorporated in order to block the UV radiation in sunlight and prevent it from penetrating to the skin or hair or reduce the amount of UV radiation that does reach the skin or hair. Inorganic UV protectants and organic UV protectants exist. Some of the inorganic powders and metal powder pigments cited above also act as UV protectants, specific examples thereof being metal oxides such as titanium oxide, zinc oxide, cerium oxide, low-valent titanium oxides, iron-doped titanium oxides, and so forth; metal hydroxides such as iron hydroxide and so forth; metal flake such as iron oxide plates, aluminum flake, and so forth; and ceramics such as silicon carbide and so forth. Their average particle diameter is preferably 1 to 100 nm. These powders and particulates are preferably subjected to a heretofore known surface treatment, for example, a fluorinated compound treatment (preferably a perfluoroalkyl phosphate treatment, perfluoroalkylalkoxysilane treatment, perfluoropolyether treatment, fluorosilicone treatment, or fluorinated silicone resin treatment), silicone treatment (preferably a methylhydrogenpolysiloxane treatment, dimethylpolysiloxane treatment, or vapor-phase tetramethyltetrahydrogencyclotetrasiloxane treatment), silicone resin treatment (preferably a trimethylsiloxysilicic acid treatment), pendant treatment (addition of, for example, an alkyl chain after a vapor-phase silicone treatment), titanium coupling agent treatment, silane treatment (preferably an alkylalkoxysilane treatment or alkyldisilazane treatment), oil treatment, N-acylated lysine treatment, polyacrylic acid treatment, metal soap treatment (a stearate salt or myristate salt is preferred), acrylic resin treatment, metal oxide treatment, and so forth; treatment using a combination of a plurality of these treatments is more preferred. For example, the surface of a titanium oxide micropowder may be coated with a metal oxide, e.g., silicon oxide or alumina, followed by treatment of the surface with an alkylalkoxysilane. The amount of surface treatment is preferably in the range of 0.1 to 50 mass % as the total amount of surface treatment with reference to the mass of the powder.

Organic UV protectants exhibit a strong capacity to absorb UV radiation and through their absorption of the UV radiation in sunlight function to prevent UV radiation from reaching the skin or hair or function to reduce the amount reaching the skin or hair. The organic UV protectants can be exemplified by salicylic acid types such as homomethyl salicylate, octyl salicylate, triethanolamine salicylate, and so forth; PABA types such as para-aminobenzoic acid, ethyldihydroxypropyl-para-aminobenzoic acid, glyceryl-para-aminobenzoic acid, octyldimethyl-para-aminobenzoic acid, amyl para-dimethylaminobenzoate, 2-ethylhexyl para-dimethylaminobenzoate, hexyl 2-[4-(diethylamino)-2-hydroxybenzoyl]benzoate, and so forth; benzophenone types such as 4-(2-β-glucopyranosyloxy)propoxy-2-hydroxybenzophenone, dihydroxydimethoxybenzophenone, sodium dihydroxydimethoxybenzophenonedisulfonate, 2-hydroxy-4-methoxybenzophenone, hydroxymethoxybenzophenonesulfonic acid and its trihydrate, sodium hydroxymethoxybenzophenonesulfonate, 2-hydroxy-4-methoxybenzophenone-5-sulfuric acid, 2,2'-dihydroxy-4-methoxybenzophenone, 2,4-dihydroxybenzophenone, 2,2',4,4'-tetrahydroxybenzophenone, 2,2'-dihydroxy-4,4'-dimethoxybenzophenone, 2-hydroxy-4-N-octoxybenzophenone, and so forth; cinnamic acid types such as 2-ethylhexyl para-methoxycinnamate (also known as octyl para-methoxycinnamate), glyceryl mono(2-ethylhexanoate) di-para-methoxycinnamate, methyl 2,5-diisopropylcinnamate, 2,4,6-tris [4-(2-ethylhexyloxycarbonyl)anilino]-1,3,5-triazine, methylbis(trimethylsiloxy)silylisopentyl trimethoxycinnamate, dimethylpolysiloxy diethyl benzalmalonate ester mixtures (dimethicodiethylbenzalmalonate), isopropyl para-methoxycinnamate diisopropylcinnamate ester mixtures, diethanolamine salt of p-methoxyhydrocinnamic acid, and so forth; benzoylmethane types such as 2-phenylbenzimidazole-5-sulfuric acid, 4-isopropyldibenzoylmethane, 4-tert-butyl-4'-methoxydibenzoylmethane, and so forth; 2-ethylhexyl 2-cyano-3,3-diphenylpropane-2-enoate (also known as octocrylene); 2-ethylhexyl dimethoxybenzylidenedioxoimidazolidinepropionate; 1-(3,4-dimethoxyphenyl)-4,4-dimethyl-1,3-pentanedione; cinoxate; methyl o-aminobenzoate; 2-ethylhexyl 2-cyano-3,3-diphenylacrylate; 3-(4-methylbenzylidene)camphor; octyltriazone; 2-ethylhexyl 4-(3,4-dimethoxyphenylmethylene)-2,5-dioxo-1-imidazolidinepropionate; as well as polymeric derivatives of the preceding and silane derivatives of the preceding.

Also usable are polymer powders that contain an organic UV protectant as described above. The polymer powder may or may not be hollow; its average primary particle diameter is preferably in the range from 0.1 to 50 μm; and its particle size distribution may be broad or sharp. The type of polymer can be exemplified by acrylic resins, methacrylic resins, polystyrene resins, polyurethane resins, polyethylenes, polypropylenes, polyethylene terephthalates, silicone resins, nylons, acrylamide resins, polypeptides, silicone-modified polypeptides, and so forth. A preferred powder comprises a polymer powder as described above containing 0.1 to 30 mass % organic UV protection component, and a powder containing 4-tert-butyl-4'-methoxydibenzoylmethane (UV-A absorber) is particularly preferred.

Among the preceding UV protectants, at least one selection from the group consisting of microparticulate titanium oxide, microparticulate zinc oxide, 2-ethylhexyl para-methoxycinnamate, 4-tert-butyl-4'-methoxydibenzoylmethane, and benzophenone-type UV absorbers is preferred because these are in general use, are easy to obtain, and have excellent UV protective effects. The use of an inorganic UV protectant in combination with an organic UV protectant is preferred, and the use of a UV protective component for UV-A in combination with a UV protectant for UV-B is even more preferable.

The content of the UV protectant (i) in the cosmetic of the present invention varies as a function of the particular cosmetic formulation and is preferably in the range of 0.1 to 60 mass % and particularly preferably 3 to 40 mass %, in each case based on the mass of the cosmetic. The amount of incorporation of the inorganic UV protectant is preferably 0.1 to 30 mass % based on the mass of the cosmetic, while the amount of incorporation of the organic UV absorber is preferably 0.1 to 20 mass % based on the mass of the cosmetic. A UV protective effect cannot be exhibited at below the cited lower limit; at above the cited upper limit, the effects of the polyether-modified organopolysiloxane or diorganopolysiloxane-polyether block copolymer (a) of the present invention may be inadequate depending on the particular cosmetic. The UV protectant (i) is preferably incorporated at a range of 0.1 to 20 mass % (based on the total quantity of the cosmetic) for the amount of component (a) incorporation: in this combination range, a more continuous UV protective effect is obtained as compared to the absence of component (a).

The salt (j) is a component that, through its co-use with the aforementioned polyether-modified organopolysiloxane or diorganopolysiloxane-polyether block copolymer (a) of the present invention, enables the formation of a more uniform dispersed state for the cosmetic. The salt (j) can be, for example, an inorganic salt, a salt of an organic acid, an amine salt, or an amino acid salt. The inorganic salt can be exemplified by sodium, potassium, magnesium, calcium, aluminum, zirconium, or zinc salts of inorganic acids such as hydrochloric acid, sulfuric acid, carbonic acid, nitric acid, and so forth; the organic acid salt can be exemplified by salts of organic acids such as acetic acid, dehydroacetic acid, citric acid, malic acid, succinic acid, ascorbic acid, stearic acid, and so forth; and the amine salts and amino acid salts can be exemplified by salts of amines such as triethanolamine and salts of amino acids such as glutamic acid. Also usable in addition to the preceding are salts of hyaluronic acid, chondroitin sulfuric acid, and so forth; aluminum/zirconium/glycine complexes; and neutral acid-base salts used in cosmetic recipes.

In addition to the components cited above, the cosmetic of the present invention may contain, within a range that does not impair the objects of the present invention, various other components such as (k) an antiseptic preservative, physiologically active component, oil-soluble gelling agent, pH adjuster, chelating agent, solvent, propellant, oxidation inhibitor, moisture-retention component, fragrance, and so forth. These components may be dissolved or dispersed in the above-described oil (b), compound that contains an alcoholic hydroxyl group in the molecular structure (c), or water (d) and in this state blended with the other cosmetic components, or they may be dissolved or dispersed—using the polyether-modified organopolysiloxane or diorganopolysiloxane-polyether block copolymer (a) of the present invention—in the above-described oil (b), compound that contains an alcoholic hydroxyl group in the molecular structure (c), or water (d) and in this state blended with the other cosmetic components.

The preservative can be exemplified by alkyl para-hydroxybenzoates, benzoic acid, sodium benzoate, sorbic acid, potassium sorbate, and phenoxyethanol. Antibacterials can be exemplified by benzoic acid, salicylic acid, carbolic acid, sorbic acid, alkyl para-hydroxybenzoates, para-chloro-meta-cresol, hexachlorophene, benzalkonium chloride, chlorhexidine chloride, trichlorocarbanilide, triclosan, photosensitizers, phenoxyethanol, 1,3-dimethylol-5,5-dimethylhydantoin, aqueous solutions of methylchloroisothiazolinone methylisothiazolinone mixtures, N,N"-methylenebis[N'-(3-hydroxymethyl-2,5-dioxo-4-imidazolidinyl)urea], and so forth.

The physiologically active component can be exemplified by substances that impart any physiological activity to the skin when applied to the skin, for example, antiinflammatory agents, aging inhibitors, UV protectants, astringents, antioxidants, hair stimulants and hair growth promoters, moisture-retention agents, blood circulation promoters, antibacterials, antiseptics, desiccants, algefacients, calorifacients, vitamins, amino acids, wound healing promoters, irritation reducers, analgesics, cell activators, enzymatic components, and so forth. Among the preceding, natural vegetable extract components, seaweed extract components, and herbal medicine components are particularly preferred. The addition of one or two or more of these physiological active components is preferred in the present invention.

The following are examples of the physiologically active component: *Angelica keiskei* extract, avocado extract, *Hydrangea serrata* extract, althea extract, arnica extract, aloe extract, apricot extract, apricot kernel extract, *Gingko biloba* extract, fennel fruit extract, turmeric root extract, oolong tea extract, *Rosa multiflora* extract, *Echinacea angustifolia* leaf extract, *Scutellaria baicalensis* root extract, *Phellodendron amurense* extract, coptis rhizome extract, *Hordeum vulgare* seed extract, *Hypericum perforatum* extract, *Lamium album* extract, *Nasturtium officinale* extract, orange extract, dried sea water, seaweed extract, hydrolyzed elastin, hydrolyzed wheat flour, hydrolyzed silk, Chamomile extract, carrot extract, *Artemisia capillaris* flower extract, licorice extract, karkade extract, *Pyracantha fortuneana* extract, kiwi extract, cinchona extract, cucumber extract, guanosine, *Gardenia florida* extract, *Sasa veitchii* extract, *Sophora angustifolia* extract, walnut extract, grapefruit extract, *Clematis vitalba* leaf extract, chlorella extract, *Morus alba* root extract, *Gentiana lutea* extract, black tea extract, yeast extract, burdock extract, fermented rice bran extract, rice germ oil, comfrey extract, collagen, *Vaccinum vitis idaea* extract, *Asiasarum* root extract, *Bupleurum falcatum* extract, umbilical extract, Salvia extract, soapwort extract, Sasa bamboo grass extract, *Crataegus cuneata* fruit extract, *Zanthoxylum piperitum* extract, shiitake extract, *Rehmannia* root extract, *Lithospermum erythrorhizone* root extract, *Perilla ocymoides* extract, *Tilia cordata* flower extract, *Spiraea ulmaria* extract, *Paeonia albiflora* extract, *Acorus calamus* root extract, *Betula alba* extract, *Equisetum arvense* extract, *Hedera helix* extract, *Crataegus oxyacantha* extract, *Sambucus nigra* extract, *Achillea millefolium* extract, *Mentha piperita* leaf extract, sage extract, *Malva sylvestris* extract, *Cnidium officinale* root extract, *Swertia japonica* extract, soybean extract, *Zizyphus jujuba* fruit extract, thyme extract, tea extract, *Eugenia caryophyllus* flower extract, *Imperata cylindrica* extract, *Citrus unshiu* Marc extract, angelica root extract, *Calendula officinalis* extract, *Prunus persica* stone extract, *Citrus aurantium* peel extract, *Houttuynia cordata* extract, tomato extract, natto extract, carrot extract, garlic extract, *Rosa canina* fruit extract, hibiscus extract, Ophiopogon tuber extract, *Nelumbo nucifera* extract, parsley extract, honey, witch hazel extract, *Parietaria officinalis* extract, *Isodonis japonicus* extract, bisabolol, *Eriobotrya japonica* extract, coltsfoot flower extract, *Petasites japonicus* extract, *Poria cocos* extract, butcher's broom extract, grape extract, propolis, *Luffa cylindrica* fruit extract, safflower flower extract, peppermint extract, *Tillia miquellana* extract, *Paeonia suffruticosa* root extract, hops extract, *Pinus sylvestris* cone extract, horse chestnut extract, Japanese skunk cabbage extract, *Sapindus mukurossi* peel extract, melissa extract, peach extract, *Centaurea cyanus* flower extract, eucalyptus extract, *Saxifraga sarementosa* extract, *Citrus junos* extract, *coix* seed extract, *Artemisia princeps* extract, lavender extract, apple extract, lettuce extract, lemon extract, *Astragalus sinicus* extract, rose extract, rosemary extract, Roman chamomile extract, and royal jelly extract.

Additional examples are as follows: biopolymers such as deoxyribonucleic acid, mucopolysaccharides, sodium hyaluronate, sodium chondroitin sulfate, collagen, elastin, chitin, chitosan, hydrolyzed eggshell membrane, and so forth; amino acids such as glycine, valine, leucine, isoleucine, serine, threonine, phenylalanine, arginine, lysine, aspartic acid, glutamic acid, cystine, cysteine, methionine, tryptophan, and so forth; hormones such as estradiol, ethenylestradiol, and so forth; oil components such as sphingolipids, ceramides, cholesterol, cholesterol derivatives, phospholipids, and so forth; antiinflammatories such as ε-aminocaproic acid, glycyrrhizinic acid, β-glycyrrhetinic acid, lysozyme chloride, guaiazulene, hydrocortisone, allantoin, tranexamic acid, azulene, and so forth; vitamins such as vitamins A, B2, B6, C, D, and E, calcium pantothenate, biotin, nicotinamide, vitamin C ester, and so forth; active components such as allantoin, diisopropylamine dichloroacetate, 4-aminomethyl cyclohexanecarboxylic acid, and so forth; antioxidants such as tocopherol, carotinoids, flavonoids, tannins, lignans, saponins, butylhydroxyanisole, dibutylhydroxytoluene, phytic acid, and so forth; cell activators such as α-hydroxy acids, β-hydroxy acids, and so forth; circulation promoters such as γ-orizanol, vitamin E derivatives, and so forth; wound healing agents such as retinol, retinol derivatives, and so forth; algefacients such as cepharanthine, glycyrrhiza extract, *capsicum* tincture, hinokitiol, iodized garlic extract, pyridoxine hydrochloride, dl-α-tocopherol, dl-α-tocopherol acetate, nicotinic acid, nicotinic acid derivatives, calcium pantothenate, D-pantothenyl alcohol, acetyl pantothenyl ethyl ether, biotin, allantoin, isopropylmethylphenol, estradiol, ethynylestradiol, capronium chloride, benzalkonium chloride, diphenhydramine hydrochloride, Takanal, camphor, salicylic acid, nonylic acid vanillylamide, nonanoic acid vanillylamide, piroctone olamine, glyceryl pentadecanoate, 1-menthol, camphor, and so forth; and hair growth promoters such as mononitroguaiacol, resorcinol, γ-aminobutyric acid, benzethonium chloride, mexiletine hydrochloride, auxins, estrogen, cantharis tincture, cyclosporine, zinc pyrithione, hydrocortisone, minoxidil, polyoxyethylene sorbitan monostearate, peppermint oil, sasanishiki extract, and so forth.

The oil-soluble gelling agent can be exemplified by metal soaps such as aluminum stearate, magnesium stearate, zinc myristate, and so forth; amino acid derivatives such as N-lauroyl-L-glutamic acid, α,γ-di-n-butylamine, and so forth; dextrin fatty acid esters such as dextrin palmitate, dextrin stearate, dextrin 2-ethylhexanoate palmitate, and so forth; sucrose fatty acid esters such as sucrose palmitate, sucrose stearate, and so forth; benzylidene derivatives of sorbitol such as monobenzylidene sorbitol, dibenzylidene sorbitol, and so forth; and organomodified clay minerals such as dimethylbenzyldodecylammonium montmorillonite clay, dimethyldioctadecylammonium montmorillonite clay, and so forth. Two or more of the preceding can be used as necessary.

The pH adjuster can be exemplified by lactic acid, citric acid, glycolic acid, succinic acid, tartaric acid, dl-malic acid, potassium carbonate, sodium bicarbonate, and ammonium bicarbonate. The chelating agent can be exemplified by alanine, sodium edetate, sodium polyphosphate, sodium metaphosphate, and phosphoric acid.

The solvent will vary as a function of the particular cosmetic formulation, and can be exemplified by the above-described component (d) and also by component (c)'s that are liquid at room temperature.

The propellant can be exemplified by light liquid isoparaffins, ethers, LPG, N-methylpyrrolidone, and next-generation fluorocarbons.

The oxidation inhibitor can be exemplified by tocopherol, butylhydroxyanisole, dibutylhydroxytoluene, phytic acid, and so forth; the chelating agent can be exemplified by alanine, sodium edetate, sodium polyphosphate, sodium metaphosphate, phosphoric acid, and so forth.

The moisture-retention component can be exemplified by the oils encompassed by the aforementioned component (b) (particularly animal and vegetable oils and hydrocarbon oils), the sugar alcohols encompassed by component (c), and polyhydric alcohols and also by hyaluronic acid, chondroitin sulfate, pyrrolidonecarboxylic acid salts, polyoxyethylene methylglucoside, and polyoxypropylene methylglucoside.

The fragrance is incorporated in order to impart an aroma or scent to the cosmetic or mask an unpleasant odor. This may be any fragrance normally incorporated in cosmetics and is not otherwise particularly limited. The fragrance includes the various extracts provided above as examples of the physiologically active component and can otherwise be exemplified by extracts from flowers, seeds, leaves, roots, and so forth of various plants; fragrances extracted from seaweed; fragrances extracted from various animal parts and secretions (e.g., musk and sperm oil); and artificially synthesized fragrances (e.g., menthol, musk, acetate esters, vanilla). The polyether-modified organopolysiloxane or diorganopolysiloxane-polyether block copolymer (a) of the present invention is not accompanied by a strong odor even after elapsed time and for this reason offers the advantage of not impairing the desirable smell of the fragrance.

With regard to the polyether-modified organopolysiloxane encompassed by the polyether-modified organopolysiloxane or diorganopolysiloxane-polyether block copolymer (a) of the present invention, the polyether moiety thereof comprises only polyether derived from glycidyl ether or comprises polyether at least 90 mol % of which derives from glycidyl ether, and as a result this polyether-modified organopolysiloxane—unlike heretofore known polyether-modified organopolysiloxanes in which the polyether moiety comprises only polyoxyalkylene—resists oxidation in air and resists the production with elapsed time of carbonyl-functional allergenically antigenic compounds, as typified by formaldehyde.

With regard to the diorganopolysiloxane-polyether block copolymer encompassed by the polyether-modified organopolysiloxane or diorganopolysiloxane-polyether block copolymer (a) of the present invention, the polyether moiety thereof comprises only polyether derived from glycidyl ether, and as a result this diorganopolysiloxane-polyether block copolymer—unlike heretofore known diorganopolysiloxane-polyether block copolymers in which the polyether moiety comprises only polyoxyalkylene—resists oxidation in air and resists the production with elapsed time of carbonyl-functional allergenically antigenic compounds, as typified by formaldehyde. Accordingly, the cosmetic of the present invention offers the advantages of resisting oxidation in air and resisting the production with elapsed time of carbonyl-functional allergenically antigenic compounds, as typified by formaldehyde.

EXAMPLES

The conditions for the analyses of the starting materials and products in the reference examples and examples are given below.

[Gel permeation chromatography (GPC)]

The gel permeation chromatographic (GPC) instrument was an HLC-8020 gel permeation chromatograph (product of Tosoh Corporation) equipped with a refractive index detector and two TSKgel $GMH_{XL}$-L columns (product of Tosoh Corporation). The sample was submitted to measurement as the 2 weight % chloroform solution. The calibration curve was constructed using standard polystyrenes of known number-average molecular weight and weight-average molecular weight. The number-average molecular weight and the weight-average molecular weight were then determined in terms of the molecular weight of the standard polystyrenes. The molecular weight distribution (polydispersity) was calculated from the number-average molecular weight and the weight-average molecular weight.

[$^{13}$C-nuclear magnetic resonance ($^{13}$C-NMR) analysis]

The measurements were carried out using a JNM-EX400 Fourier-transform nuclear magnetic resonance instrument from JEOL Ltd.

The sample was dissolved in deuterochloroform or deuteromethanol and was measured with the addition of tris(acetylacetonato)chromium(III) as relaxation reagent.

[Infrared absorption spectroscopic analysis]

The measurements were carried out using a NEXUS 670 Fourier-transform infrared spectroscopic analyzer from Thermo Nicolet. The measurements were carried out by the sandwich method, in which the sample was sandwiched between two KBr plates.

Reference Example 1

$^{13}$C-NMR analysis of a commercial glycidyl methyl ether that contained residual starting material from the synthesis process and organochlorine compound by-products showed that this commercial glycidyl methyl ether contained 3.4 mol % (13700 ppm chlorine) as epichlorohydrin equivalent. 500 g of this glycidyl methyl ether was placed in a four-neck flask equipped with a thermometer, reflux condenser, and stirrer;

25 g of sodium hydroxide powder (average particle diameter ≧300 μm) was introduced (this sodium hydroxide powder had been obtained by crushing sodium hydroxide lumps with a hammer); and stirring was carried out for 3 hours at 80° C. under a nitrogen blanket. Simple distillation was then carried out at a reduced pressure of 40-50 mmHg to obtain a 360 g of fraction. This fraction was analyzed by NMR and was thereby shown to be methyl glycidyl ether with a purity of 99.9%. Signals associated with the impurities did not appear on the NMR analytical chart. This methyl glycidyl ether fraction was dried by the addition of 5 weight % molecular sieve 4A to yield a purified methyl glycidyl ether.

Reference Example 2

3.90 g (37.8 mmol) of ethylene glycol monoallyl ether, 0.05 g (0.90 mmol) of potassium hydroxide powder, and 20.0 g (227 mmol) of methyl glycidyl ether purified as in Reference Example 1 were introduced into a four-neck flask equipped with a thermometer, reflux condenser, and stirrer and were stirred for 2 hours at 120-130° C. under a nitrogen blanket. The reaction was cooled to room temperature and the polymerization was stopped by the addition of 0.060 g of acetic acid with stirring. 10 g toluene was added to the liquid polymerization product; 1 gram Kyoward 500SN, a hydrotalcite-type adsorbent from Kyowa Chemical Industry Co., Ltd., was then added; and stirring was carried out for 2 hours. The potassium acetate by-product and the adsorbent were removed by filtration and the low boilers were distilled off by heating the filtrate under reduced pressure to obtain 22.7 g (yield=95%) of a clear liquid residue. Analysis of this liquid residue by GPC gave a number-average molecular weight in terms of a standard polystyrene of 940 and a polydispersity of 1.124. NMR analysis of this liquid residue showed it to be poly(methyl glycidyl ether) with average structural formula (26) having an average degree of polymerization of 5.3 (calculated value=6) and the following values for general formula (7): R=allyloxyethyl, n=5.3, W=methyl, m=0, p=1, and Y=hydrogen atom.

Average Structural Formula (26):

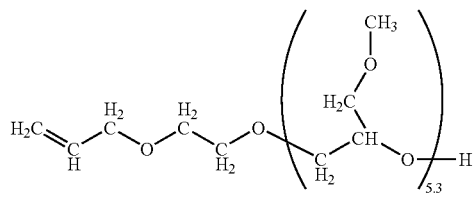

Reference Examples 3 to 5

Liquid poly(methyl glycidyl ether)s having different degrees of polymerization were prepared by carrying out polymerization and so forth under the same conditions as in Reference Example 2, with the following exceptions: the amount of ethylene glycol monoallyl ether charged was changed from that in Reference Example 2 and potassium t-butoxide was used as the polymerization catalyst rather than potassium hydroxide. The values for general formula (7) were as follows: R=allyloxyethyl, n as reported below, W=methyl, m=0, p=1, and Y=hydrogen atom. The amounts charged and the analytical results are reported in Table 1 below.

TABLE 1

| | Reference Example 3 | Reference Example 4 | Reference Example 5 |
|---|---|---|---|
| ethylene glycol monoallyl ether | 1.86 g 18.2 mmol | 0.93 g 9.1 mmol | 0.46 g 4.5 mmol |
| polymerization catalyst | t-BuOK 0.1 g 0.9 mmol | t-BuOK 0.1 g 0.9 mmol | t-BuOK 0.1 g 0.9 mmol |
| yield | 21.4 g | 20.8 g | 20.5 g |
| % yield | 98% | 99.5% | 100% |
| number-average molecular weight | 1638 | 2678 | 4214 |
| polydispersity | 1.063 | 1.053 | 1.078 |
| average degree of polymerization (measured value) | 12.3 | 25 | 48 |
| degree of polymerization (calculated value) | 12.5 | 25 | 50 |

The poly(methyl glycidyl ether) of Reference Example 3 corresponds to n=12.3 in average structural formula (27).

The poly(methyl glycidyl ether) of Reference Example 4 corresponds to n=25 in average structural formula (27).

The poly(methyl glycidyl ether) of Reference Example 5 corresponds to n=48 in average structural formula (27).

Average Structural Formula (27):

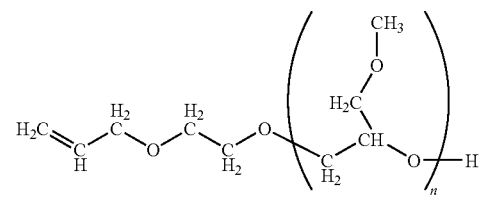

Reference Example 6

31.4 g (yield=99.8%) of a liquid residue was obtained by carrying out polymerization and so forth using the same conditions as in Reference Example 2, with the exception that 29.6 g (227 mmol) of butyl glycidyl ether was used in place of the methyl glycidyl ether used in Reference Example 2. GPC analysis of this liquid residue gave a number-average molecular weight in terms of a standard polystyrene of 1,967 and a polydispersity of 1.088. NMR analysis of this liquid residue demonstrated that it was a poly(butyl glycidyl ether) with average structural formula (28) having an average degree of polymerization of 12.0 (calculated value=12.5) and the following values for general formula (7): R=allyloxyethyl, n=12, W=butyl, m=0, p=1, and Y=hydrogen atom.

Average Structural Formula (28):

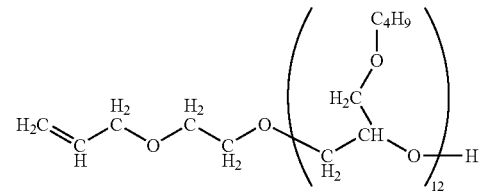

Reference Example 7

26.6 g (yield=100%) of a liquid residue was obtained by carrying out polymerization and so forth using the same conditions as in Example 2, with the exception that a mixture of 14.8 g (113.5 mmol) of butyl glycidyl ether and 10.0 g of methyl glycidyl ether (113.5 mmol) was used in place of the 20.0 g (227 mmol) of methyl glycidyl ether used in Example 2. GPC analysis of this liquid residue gave a number-average molecular weight in terms of a standard polystyrene of 1,836 and a polydispersity of 1.080. NMR analysis of this liquid residue demonstrated that it was a methyl glycidyl ether.butyl glycidyl ether random copolymer with average structural formula (29) having a total average degree of polymerization of 12.3 (calculated value=12.5, average degree of polymerization of the unit originating from methyl glycidyl ether=6.0, average degree of polymerization of the unit originating from butyl glycidyl ether=6.3) and the following values for general formula (7): R=allyloxyethyl, n=6 and 6.3, W=methyl and butyl, m=0, p=1, and Y=hydrogen atom.

Average Structural Formula (29):

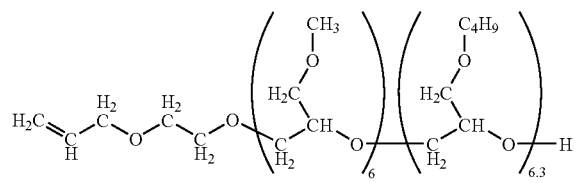

Reference Example 8

2.00 g (18.8 mmol) of diethylene glycol, 0.10 g (0.90 mmol) of potassium t-butoxide, and 20.0 g (227 mmol) of glycidyl methyl ether purified as in Reference Example 1 were introduced into a four-neck flask equipped with a thermometer, reflux condenser, and stirrer and were stirred for 3 hours at 120-130° C. under a nitrogen blanket. After then cooling to 80° C., 1.63 g (40.7 mmol) sodium hydroxide was introduced with stirring. 4.11 g (45.4 mmol) of methallyl chloride was subsequently added dropwise, whereupon the production of a white precipitate was observed. This was followed by stirring for 2 hours at 120° C. and cooling, after which 10 g of toluene was introduced and the white salt by-product was filtered off. The low boilers were distilled from the filtrate by heating under reduced pressure to obtain 22.3 g (yield=93%) of a liquid residue. GPC analysis of this liquid residue gave a number-average molecular weight in terms of a standard polystyrene of 2,144 and a polydispersity of 1.040. NMR analysis of this liquid residue demonstrated that it was a poly(methyl glycidyl ether) with average structural formula (30) that had the following values for general formula (16): $R^5$=methallyl, X=divalent group given by general formula (5) in which W is methyl, Z=ethyleneoxy, n=q and 12.6–q, and m=2.

Average Structural Formula 30:

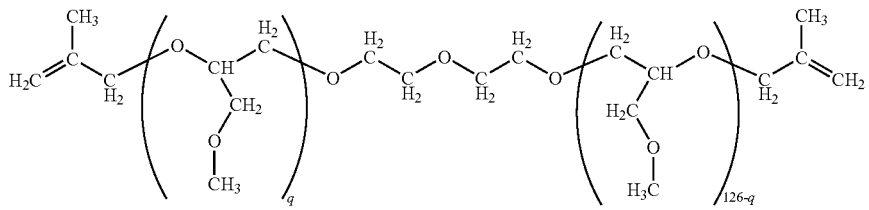

(q in the formula is larger than 0 and less than 12.6)

Reference Example 9

2.40 g (18.2 mmol) of glycerol monoallyl ether, 0.10 g (0.90 mmol) of potassium t-butoxide, and 20.0 g (227 mmol) of methyl glycidyl ether purified as in Reference Example 1 were introduced into a four-neck flask equipped with a thermometer, reflux condenser, and stirrer and were stirred for 2.5 hours at 120-140° C. under a nitrogen blanket. The reaction was cooled to room temperature and the polymerization was stopped by the addition of 0.06 g of acetic acid with stirring. 10 g of toluene was added; Kyoward 500SN, a hydrotalcite-type adsorbent from Kyowa Chemical Industry Co., Ltd., was added; and stirring was carried out for 2 hours. The potassium acetate by-product and the adsorbent were then removed by filtration and the low boilers were distilled off by heating the filtrate under reduced pressure to obtain 22.1 g (yield=99%) of a clear liquid residue. Analysis of this liquid residue by GPC gave a number-average molecular weight in terms of a standard polystyrene of 1,717 and a polydispersity of 1.036. NMR analysis of this liquid residue showed it to be poly (methyl glycidyl ether) with average structural formula (31) having the following values for general formula (7): R=allyloxypropyl, n=q and 12.6–q, m=0, W=methyl, p=2, and Y=hydrogen atom.

Average Structural Formula (31):

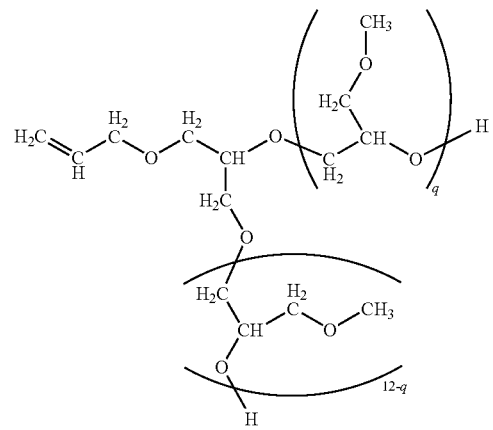

(q in the formula is greater than 0 and less than 12)

Reference Example 10

22.4 g (yield=97%) of a liquid residue was obtained by carrying out polymerization and so forth under the same conditions as in Reference Example 9, with the exception that 3.2 g (18.2 mmol) of pentaerythritol monoallyl ether was used rather than the 2.40 g (18.2 mmol) glycerol monoallyl ether that was used in Reference Example 9. Analysis of this liquid residue by GPC gave a number-average molecular weight in terms of a standard polystyrene of 2,016 and a polydispersity of 1.072. NMR analysis of this liquid residue showed it to be a poly(methyl glycidyl ether) having average structural formula (32) and the following values in general formula (7): R=group shown below

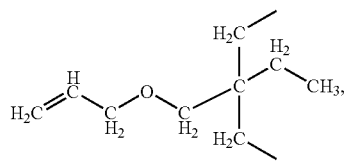

n=q and 12-q, m=0, W=methyl, p=2, and Y=hydrogen atom.
Average Structural Formula (32):

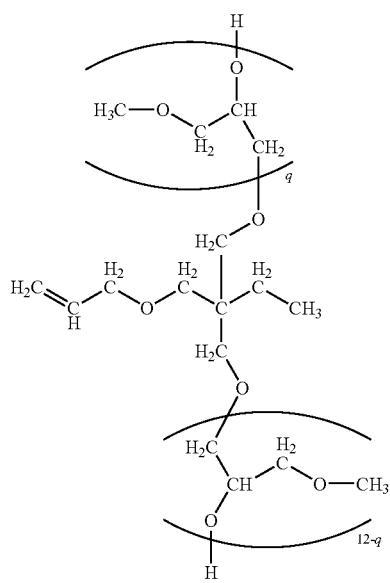

(q in the formula is greater than 0 and less than 12.6)

Reference Example 11

20.5 g (yield=96%) of a liquid residue was obtained by carrying out polymerization and so forth under the same conditions as in Reference Example 9, with the exception that 1.31 g (18.2 mmol) of 3-butenol was used rather than the 2.40 g (18.2 mmol) of glycerol monoallyl ether that was used in Reference Example 9. Analysis of this liquid residue by GPC gave a number-average molecular weight in terms of a standard polystyrene of 1,557 and a polydispersity of 1.095. NMR analysis of this liquid residue showed it to be a poly (methyl glycidyl ether) with average structural formula (33) having an average degree of polymerization of 12.6 (measured value=12.0) and the following values in general formula (7): R=butenyl, n=12.6, m=0, W=methyl, p=1, and Y=hydrogen atom.

Average Structural Formula (33):

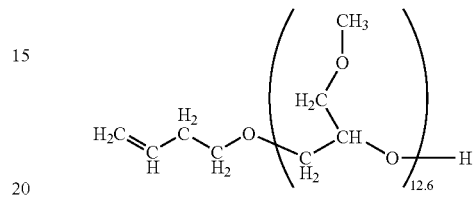

Example 1

5 g (8.8 mmol) of the poly(glycidyl methyl ether) with average structural formula (26) (produced in Reference Example 2) and 5.9 g (3.7 mmol, SiH: 7.3 mmol) of dimethylpolysiloxane endblocked with silicon-bonded hydrogen atom at both terminals and having average structural formula (34) were introduced into a stirrer-equipped four-neck flask and were mixed.

Average Structural Formula (34):

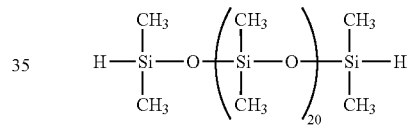

A platinum.1,3-divinyltetramethyldisiloxane complex was added in an amount that provided platinum metal at 5 ppm and mixing was carried out. Stirring was carried out for 5 hours at 80-100° C. and a sample was then taken and submitted to infrared absorption spectroscopy (IR). The results showed that the absorption characteristic of silicon-bonded hydrogen atom had disappeared and the hydrosilylation reaction had gone to completion. 10.9 g (yield=100%) of a clear, light yellow polymer was obtained. The results of $^{29}$Si- and $^{13}$C-nuclear magnetic resonance analyses (NMR) demonstrated that this polymer was a polyether-modified dimethylpolysiloxane with average structural formula (35), in which poly(methyl glycidyl ether) was bonded across a propyleneoxyethyleneoxy group at both ends of the dimethylpolysiloxane.

Average Structural Formula (35):

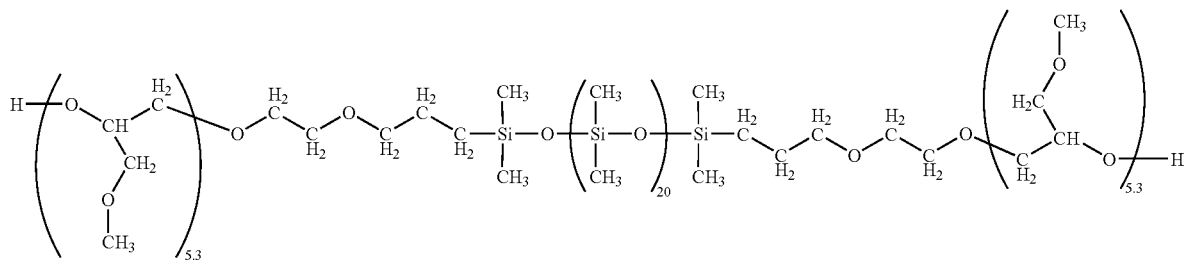

Example 2

6.8 g (11.9 mmol) of the poly(glycidyl methyl ether) with average structural formula (26) (produced in Reference Example 2) and 2.8 g (3.3 mmol, SiH: 9.9 mmol) of dimethylsiloxane.methylhydrogensiloxane copolymer with average structural formula (36) were introduced into a stirrer-equipped four-neck flask and were mixed.

Average Structural Formula (36):

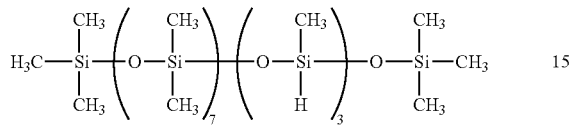

A platinum.1,3-divinyltetramethyldisiloxane complex was added in an amount that provided platinum metal at 5 ppm and mixing was carried out. Stirring was carried out for 3 hours at 100-120° C. and a sample was then taken and submitted to infrared absorption spectroscopy (IR). The results showed that the absorption characteristic of silicon-bonded hydrogen atom had disappeared and the hydrosilylation reaction had gone to completion. 10.0 g (yield=97%) of a clear, light yellow polymer was obtained. The results of $^{29}$Si- and $^{13}$C-nuclear magnetic resonance analyses (NMR) demonstrated that this polymer was a polyether-modified dimethylpolysiloxane with average structural formula (37) comprising a trimethylsiloxy-endblocked dimethylpolysiloxane in which a portion of the pendant methyl has been replaced by poly(methyl glycidyl ether) bonded through the propyleneoxyethyleneoxy group.

Average Structural Formula (37):

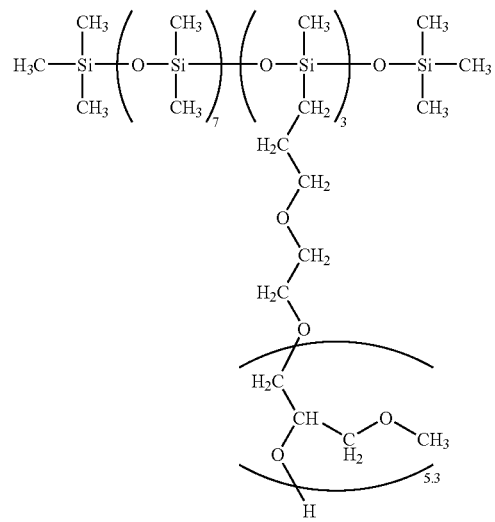

Example 3

The polyether-modified dimethylpolysiloxane with average structural formula (38), in which poly(methyl glycidyl ether) is bonded through propyleneoxyethyleneoxy at both ends of a dimethylpolysiloxane, was obtained by carrying out a reaction under the same conditions as in Example 1, but in this case using the poly(glycidyl methyl ether) with average structural formula (27) (n=12.3, produced in Reference Example 3) in place of the poly(glycidyl methyl ether) with average structural formula (26) (produced in Reference Example 2).

Average Structural Formula (38):

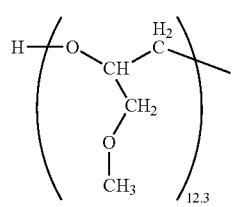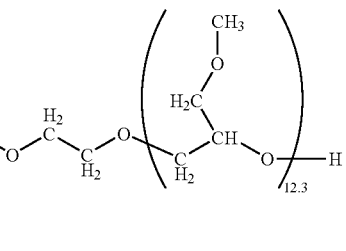

Example 4

A polyether-modified dimethylpolysiloxane with average structural formula (39), comprising a trimethylsiloxy-endblocked dimethylpolysiloxane in which a portion of the pendant methyl has been replaced by poly(methyl glycidyl ether) bonded through the propyleneoxyethyleneoxy group, was obtained by carrying out a reaction under the same conditions as in Example 2, but in this case using the poly(methyl glycidyl ether) with average structural formula (27) (n=12.3, produced in Reference Example 3) in place of the poly(glycidyl methyl ether) with average structural formula (26) (produced in Reference Example 2).

Average Structural Formula (39):

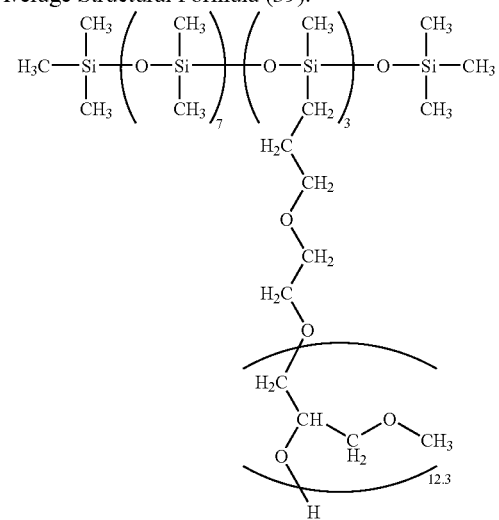

Example 5

A polyether-modified dimethylpolysiloxane with average structural formula (40), in which poly(methyl glycidyl ether) is bonded through propyleneoxyethyleneoxy at both ends of a dimethylpolysiloxane, was obtained by carrying out a reaction under the same conditions as in Example 1, but in this case using the poly(methyl glycidyl ether) with average structural formula (27) (n=25, produced in Reference Example 4) in place of the poly(glycidyl methyl ether) with average structural formula (26) (produced in Reference Example 2).

Average Structural Formula (40):

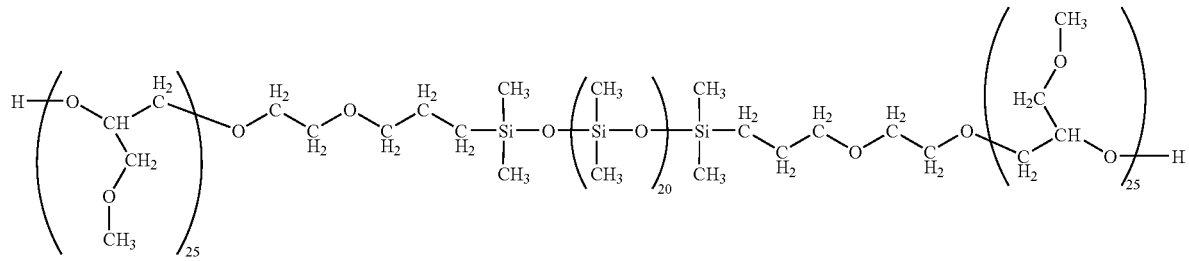

Example 6

A polyether-modified dimethylpolysiloxane with average structural formula (41), comprising a trimethylsiloxy-end-blocked dimethylpolysiloxane in which a portion of the pendant methyl has been replaced by poly(methyl glycidyl ether) bonded through the propyleneoxyethyleneoxy group, was obtained by carrying out a reaction under the same conditions as in Example 2, but in this case using the poly(methyl glycidyl ether) with average structural formula (27) (n=25, produced in Reference Example 4) in place of the poly(glycidyl methyl ether) with average structural formula (26) (produced in Reference Example 2).

Average Structural Formula (41):

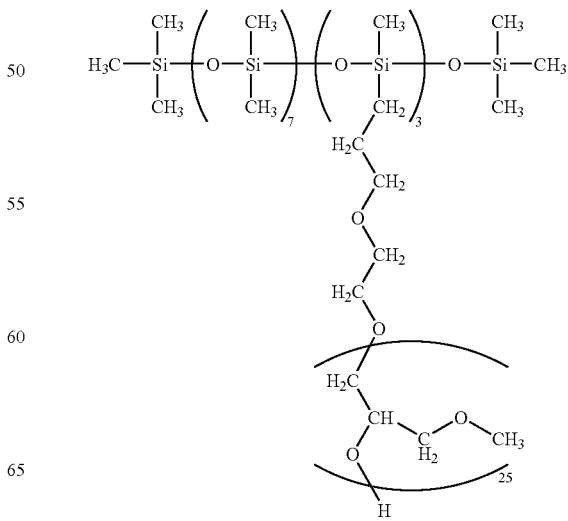

Example 7

A polyether-modified dimethylpolysiloxane with average structural formula (42), in which poly(methyl glycidyl ether) is bonded through propyleneoxyethyleneoxy at both ends of a dimethylpolysiloxane, was obtained by carrying out a reaction under the same conditions as in Example 1, but in this case using the poly(methyl glycidyl ether) with average structural formula (27) (n=48, produced in Reference Example 5) in place of the poly(glycidyl methyl ether) with average structural formula (26) (produced in Reference Example 2).

Average Structural Formula (42):

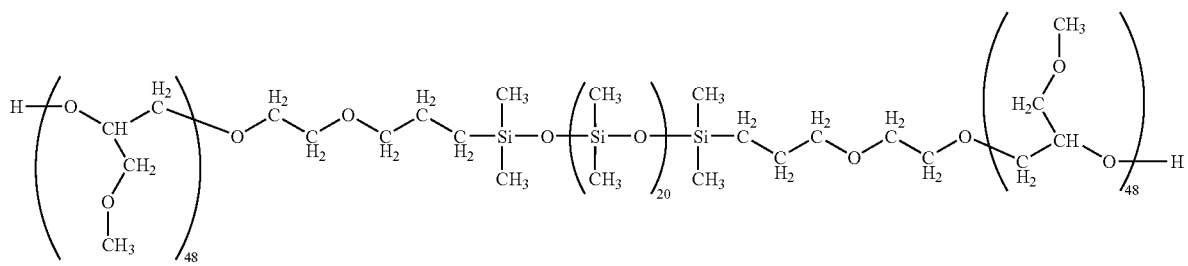

Example 8

A polyether-modified dimethylpolysiloxane with average structural formula (43), comprising a trimethylsiloxy-end-blocked dimethylpolysiloxane in which a portion of the pendant methyl has been replaced by poly(methyl glycidyl ether) bonded through the propyleneoxyethyleneoxy group, was obtained by carrying out a reaction under the same conditions as in Example 2, but in this case using the poly(methyl glycidyl ether) with average structural formula (27) (n=48, produced in Reference Example 5) in place of the poly(glycidyl methyl ether) with average structural formula (26) (produced in Reference Example 2).

Average Structural Formula (43):

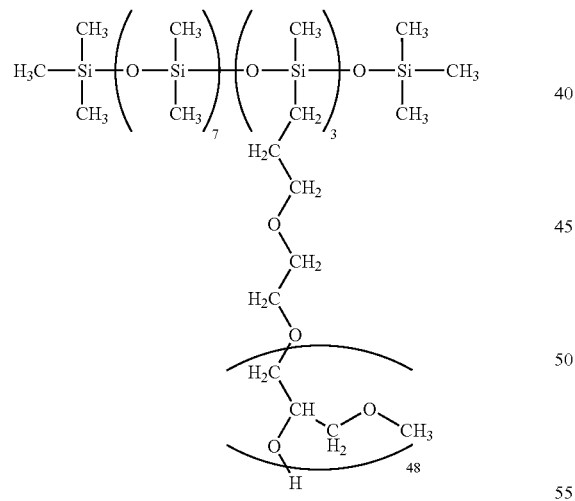

Example 9

A polyether-modified dimethylpolysiloxane with average structural formula (44), in which poly(butyl glycidyl ether) is bonded through propyleneoxyethyleneoxy at both ends of a dimethylpolysiloxane, was obtained by carrying out a reaction under the same conditions as in Example 1, but in this case using the poly(butyl glycidyl ether) with average structural formula (28) (produced in Reference Example 6) in place of the poly(methyl glycidyl ether) with average structural formula (26) (produced in Reference Example 2).

Average Structural Formula (44):

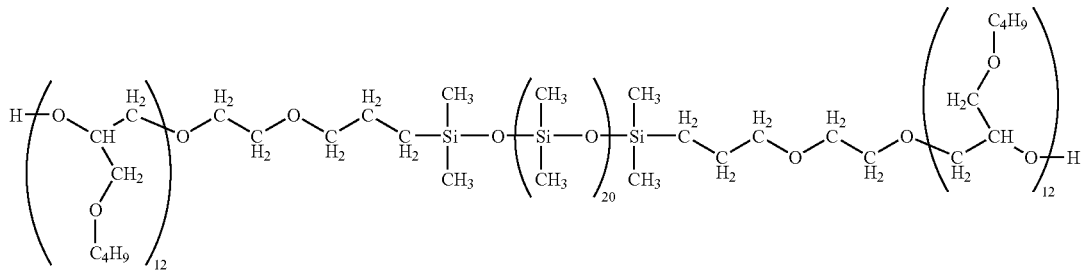

Example 10

A polyether-modified dimethylpolysiloxane with average structural formula (45), in which poly(glycidyl ether) is bonded through propyleneoxyethyleneoxy at both ends of a dimethylpolysiloxane, was obtained by carrying out a reaction under the same conditions as in Example 1, but in this case using the methyl glycidyl ether butyl glycidyl ether random copolymer with average structural formula (29) (produced in Reference Example 7) in place of the poly(methyl glycidyl ether) with average structural formula (26) (produced in Reference Example 2).

Average Structural Formula (45):

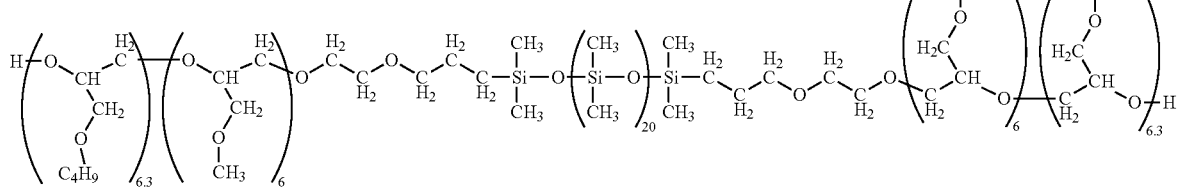

Average Structural Formula (46):

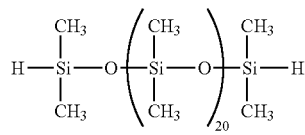

Example 11

The following were introduced into a stirrer-equipped four-neck flask and were mixed: 10 g (7.6 mmol, methallyl group: 15.2 mmol) of the poly(methyl glycidyl ether) with average structural formula (30) (produced in Reference Example 8, endblocked by methallyloxy at both terminals), a platinum 1,3-divinyltetramethyldisiloxane complex in a quantity sufficient to provide 25 ppm platinum metal with reference to the product polymer, and 35 g toluene. After heating to 80° C., 11.3 g (7.0 mmol, SiH: 14.0 mmol) of the SiH-endblocked polydimethylsiloxane with average structural formula (46) was added dropwise.

After the completion of dropwise addition, stirring was carried out for 5 hours at 85-110° C. and then for an additional 1.5 hours at 125-130° C. A sample was thereafter taken and submitted to IR analysis. The results showed that the absorption characteristic of silicon-bonded hydrogen atom had disappeared and the reaction had gone to completion. Distillation of the low boilers, e.g., toluene and so forth, by heating under reduced pressure yielded 20.7 g (yield=97%) of a light brown, slightly cloudy viscous liquid. The results of $^{29}$Si- and $^{13}$C-nuclear magnetic resonance analyses (NMR) demonstrated that this light brown viscous liquid was a poly(methyl glycidyl ether)-dimethylpolysiloxane multiblock copolymer with average structural formula (47).

Average Structural Formula (47):

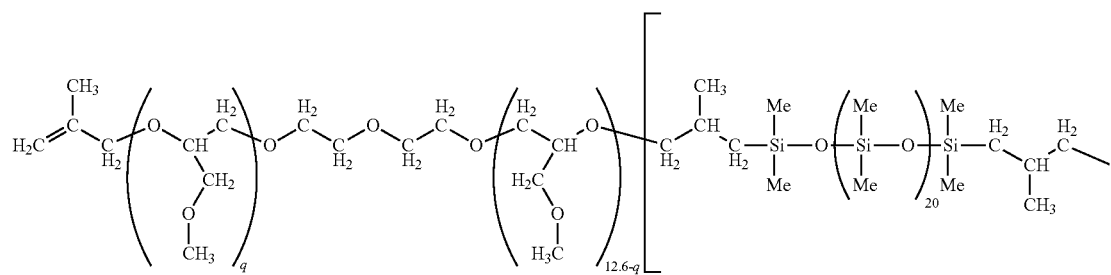

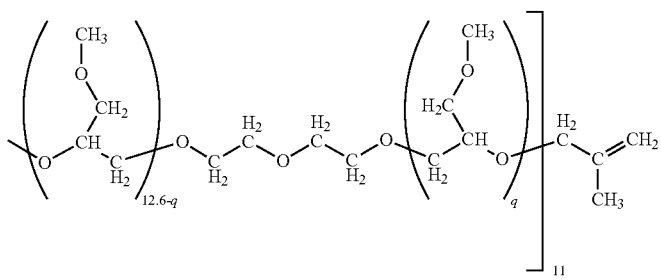

Example 12

A polyether-modified dimethylpolysiloxane with average structural formula (48), in which a branched poly(methyl glycidyl ether) is bonded through propyleneoxypropylenedioxy at both ends of a dimethylpolysiloxane, was obtained by carrying out a reaction under the same conditions as in Example 1, but in this case using the branched poly(methyl glycidyl ether) with average structural formula (31) (produced in Reference Example 9) in place of the poly(glycidyl methyl ether) with average structural formula (26) (produced in Reference Example 2).

Average Structural Formula (48):

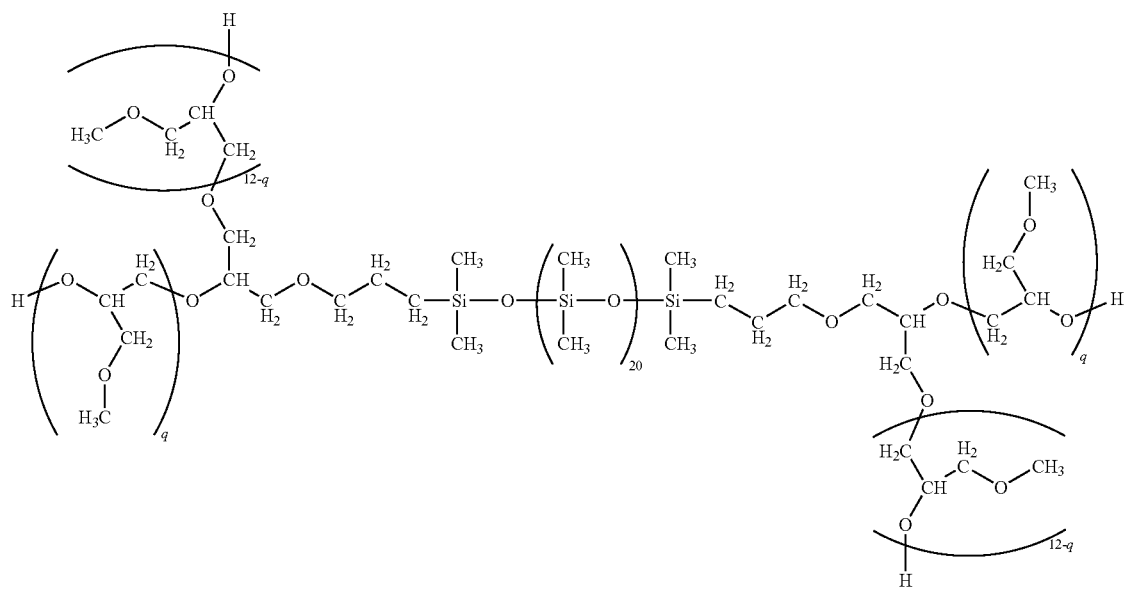

Example 13

A polyether-modified dimethylpolysiloxane with average structural formula (49), comprising a trimethylsiloxy-endblocked dimethylpolysiloxane in which a portion of the pendant methyl has been replaced by branched poly(methyl glycidyl ether) bonded through the propyleneoxypropylenedioxy group, was obtained by carrying out a reaction under the same conditions as in Example 2, but in this case using the branched poly(methyl glycidyl ether) with average structural formula (31) (produced in Reference Example 9) in place of the poly(methyl glycidyl ether) with average structural formula (26) (produced in Reference Example 2).

Average Structural Formula (49):

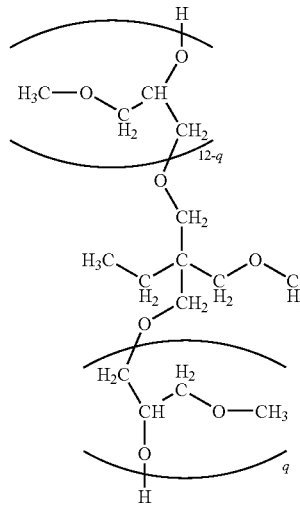

Example 14

A polyether-modified dimethylpolysiloxane with average structural formula (50), in which a poly(methyl glycidyl ether) is bonded through a branched linking group at both ends of a dimethylpolysiloxane, was obtained by carrying out a reaction under the same conditions as in Example 1, but in this case using the branched poly(methyl glycidyl ether) with average structural formula (32) (produced in Reference Example 10) in place of the poly(methyl glycidyl ether) with average structural formula (26) (produced in Reference Example 2).

Average Structural Formula (50):

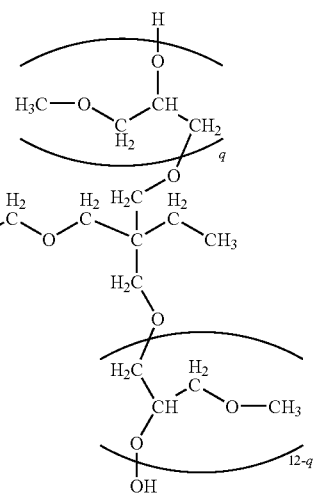

Example 15

A polyether-modified dimethylpolysiloxane with average structural formula (51), comprising a trimethylsiloxy-endblocked dimethylpolysiloxane in which a portion of the pendant methyl has been replaced by poly(methyl glycidyl ether) bonded through a branched linking group, was obtained by carrying out a reaction under the same conditions as in Example 2, but in this case using the branched poly(methyl glycidyl ether) with average structural formula (32) (produced in Reference Example 10) in place of the poly(methyl glycidyl ether) with average structural formula (26) (produced in Reference Example 2).

Average Structural Formula (51):

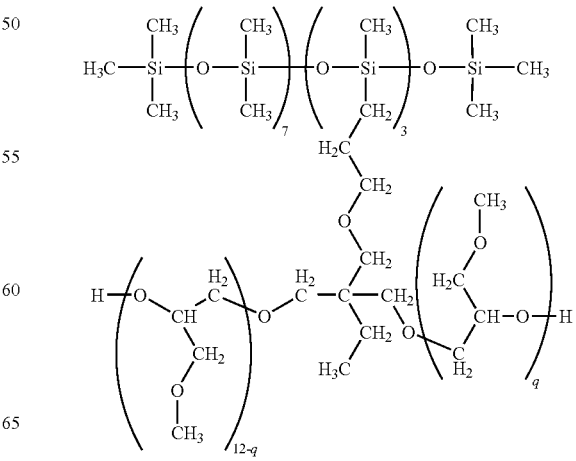

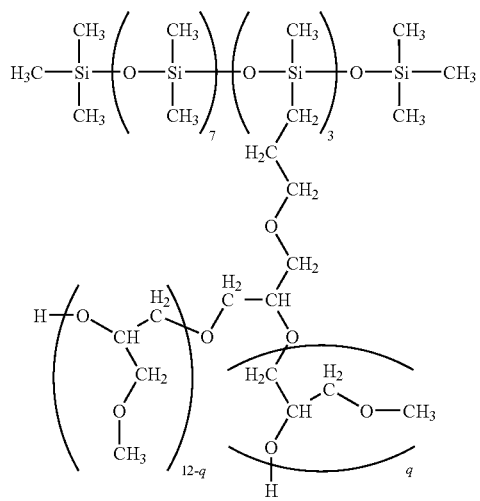

Example 16

A polyether-modified dimethylpolysiloxane with average structural formula (52), in which a poly(methyl glycidyl ether) is bonded through a butyleneoxy group at both ends of a dimethylpolysiloxane, was obtained by carrying out a reaction under the same conditions as in Example 1, but in this case using the poly(methyl glycidyl ether) with average structural formula (33) (produced in Reference Example 11) in place of the poly(methyl glycidyl ether) with average structural formula (26) (produced in Reference Example 2).

Average Structural Formula (52):

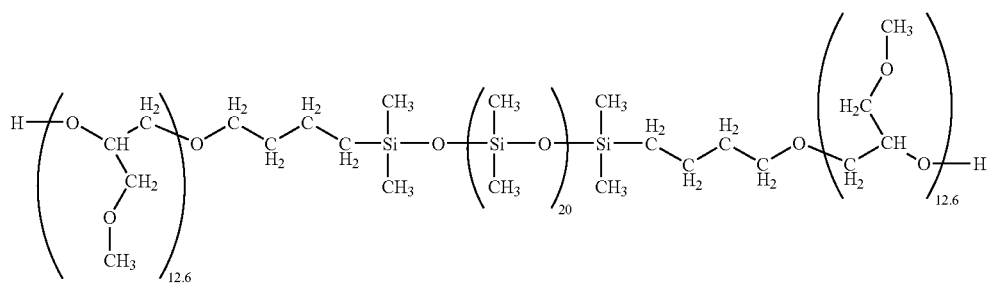

Example 17

A polyether-modified dimethylpolysiloxane with average structural formula (53), comprising a trimethylsiloxy-endblocked dimethylpolysiloxane in which a portion of the pendant methyl has been replaced by poly(methyl glycidyl ether) bonded through a butyleneoxy group, was obtained by carrying out a reaction under the same conditions as in Example 2, but in this case using the poly(methyl glycidyl ether) with average structural formula (33) (produced in Reference Example 11) in place of the poly(methyl glycidyl ether) with average structural formula (26) (produced in Reference Example 2).

Average Structural Formula (53):

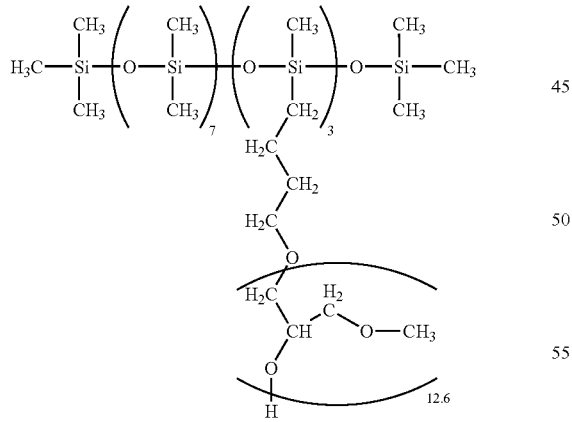

Example 18

A polyether-modified dimethylpolysiloxane with average structural formula (55), infra, comprising a trimethylsiloxy-endblocked dimethylpolysiloxane in which a portion of the pendant methyl has been replaced by poly(methyl glycidyl ether) bonded through a propyleneoxyethyleneoxy group, was obtained by carrying out a reaction under the same conditions as in Example 2, but in this case using a dimethylsiloxane methylhydrogensiloxane copolymer with the following average structural formula (54):

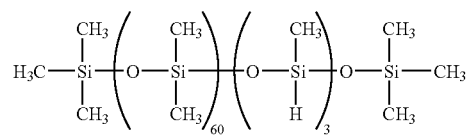

in place of the dimethylsiloxane.methylhydrogensiloxane copolymer with average structural formula (36).

Average Structural Formula (55):

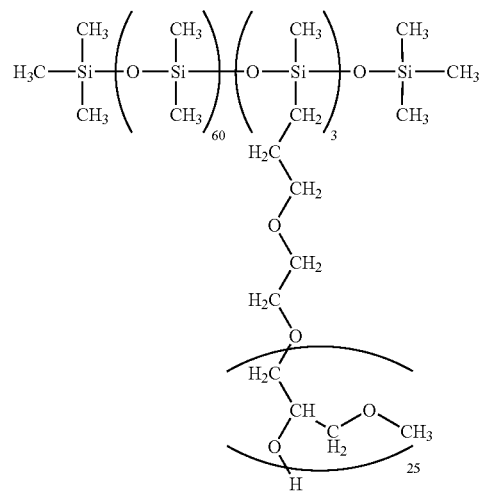

Example 19

A polyether-modified dimethylpolysiloxane with average structural formula (57), infra, comprising a trimethylsiloxy-endblocked dimethylpolysiloxane in which a portion of the pendant methyl has been replaced by poly(methyl glycidyl ether) bonded through a propyleneoxyethyleneoxy group and a portion of the pendant methyl has been replaced by —($C_3H_6O$)$_3C_{18}H_{37}$ bonded through a propyleneoxy group, was obtained by carrying out a reaction under the same conditions as in Example 1 with the following exceptions: the poly(methyl glycidyl ether) with average structural formula (26) (produced in Reference Example 2) and polyoxypropylene (3) allyl oleyl ether (RG-1252 from Nippon Nyukazai Co., Ltd.) were used in place of the poly(glycidyl methyl ether) with average structural formula (26) (produced in Reference Example 2), and a dimethylsiloxane.methylhydrogensiloxane copolymer with the following average structural formula (56):

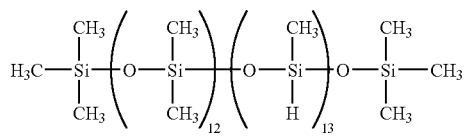

was used in place of the dimethylsiloxane.methylhydrogensiloxane copolymer with average structural formula (34).

Average Structural Formula (57):

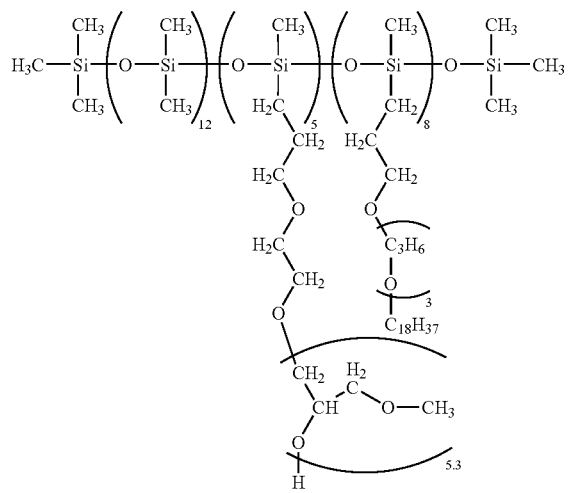

Example 20 and Comparative Example

For each of the samples described below, 5 g was introduced into a 30-cc glass bottle, which was then sealed in the air and held for 3 weeks in a 50° C. oven.

(1)
The poly(methyl glycidyl ether)-modified dimethylpolysiloxane with average structural formula (37) (prepared in Example 2)

(2)
A solution prepared by mixing, so as to obtain a concentration of 80 weight %, the poly(methyl glycidyl ether)-modified dimethylpolysiloxane with average structural formula (37) (prepared in Example 2) and a pH 6 buffer solution (aqueous mixed solution of potassium hydrogen phthalate, potassium dihydrogen phosphate, and disodium hydrogen phosphate (from Alfa Aesar))

(3)
A solution prepared by mixing, so as to obtain a concentration of 80 weight %, the poly(methyl glycidyl ether)-modified dimethylpolysiloxane with average structural formula (37) (prepared in Example 2) and a pH 7 buffer solution (aqueous mixed solution of potassium acid phthalate, potassium dihydrogen phosphate, and disodium hydrogen phosphate (from Alfa Aesar))

(4)
A solution prepared by mixing, so as to obtain a concentration of 80 weight %, the poly(methyl glycidyl ether)-modified dimethylpolysiloxane with average structural formula (37) (prepared in Example 2) and a pH 8 buffer solution (aqueous mixed solution of potassium acid phthalate, potassium dihydrogen phosphate, and disodium hydrogen phosphate (from Alfa Aesar))

(5)
The polyoxyethylene-modified dimethylpolysiloxane with the following average structural formula (58), which has almost the same polysiloxane content and molecular weight as the poly(methyl glycidyl ether)-modified dimethylpolysiloxane with average structural formula (37) (prepared in Example 2)

(6)
A solution prepared by mixing, so as to obtain a concentration of 80 weight %, the aforementioned polyoxyethylene-modified dimethylpolysiloxane and the aforementioned pH 6 buffer solution (7)
A solution prepared by mixing, so as to obtain a concentration of 80 weight %, the aforementioned polyoxyethylene-modified dimethylpolysiloxane and the aforementioned pH 7 buffer solution (8)
A solution prepared by mixing, so as to obtain a concentration of 80 weight %, the aforementioned polyoxyethylene-modified dimethylpolysiloxane and the aforementioned pH 8 buffer solution Average Structural Formula (58):

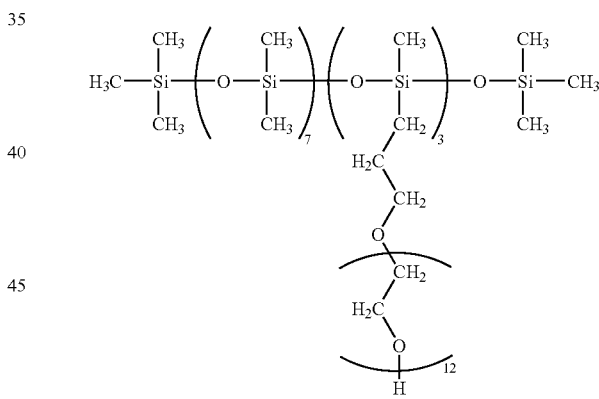

Each of the glass bottles was removed from the oven and returned to room temperature. A Formaldehyde Test Strip™ (product of Kanto Chemical Co., Inc.), which is a test paper that can selectively detect formaldehyde, was dipped into the sample. Yellowing occurred and formaldehyde was detected with the polyoxyethylene-modified dimethylpolysiloxane with average structural formula (58) itself (5) and with all of its solutions (6), (7), and (8). However, yellowing was not seen and formaldehyde was not detected with the poly(methyl glycidyl ether)-modified dimethylpolysiloxane with average structural formula (37) (prepared in Example 2) itself (1) or with any of its solutions (2), (3), and (4). IR analysis was also carried out on each of the samples after the three-week holding period at 50° C. In the case of the aforementioned polyoxyethylene-modified dimethylpolysiloxane provided as a comparative example, the polyoxyethylene-modified dimethylpolysiloxane itself (5) and all of its solutions (6), (7), and (8) produced the characteristic absorption at 1720 cm$^{-1}$, and the intensity of the absorption was stronger as the pH of the buffer solution declined. These results demonstrated that this polyoxyethylene-modified dimethylpolysiloxane was susceptible to oxidative degradation of the polyoxyethylene and was prone to generate formaldehyde, particularly under acidic conditions. In contrast, in the case of the poly(methyl glycidyl ether)-modified dimethylpolysiloxane with average structural formula (37) (prepared in Example 2), it was found that the characteristic absorption at 1720 cm$^{-1}$ and formaldehyde generation were almost entirely absent for the poly (methyl glycidyl ether)-modified dimethylpolysiloxane with average structural formula (37) itself (1) and for all of its solutions.

Example 21

An eyeliner with the following composition was prepared by the method described below.

TABLE 2

| | component | weight % |
|---|---|---|
| 1 | decamethylcyclopentasiloxane | balance |
| 2 | polyether-modified dimethylpolysiloxane prepared in Example 18 | 3 |
| 3 | silicone resin | 15 |
| 4 | dioctadecyldimethylammonium salt-modified montmorillonite | 3 |
| 5 | silicone-treated iron oxide black | 10 |
| 6 | 1,3-butylene glycol | 5 |
| 7 | preservative | suitable amount |
| 8 | fragrance | suitable amount |
| 9 | purified water | 10 |

Notes.
silicone resin: 50 weight % decamethylcyclopentasiloxane solution of a methylpolysiloxane resin with a [Me$_3$SiO$_{1/2}$]/[SiO$_2$] ratio of 0.8.
silicone-treated iron oxide black: prepared by mixing 2 weight % methylhydrogenpolysiloxane into iron oxide black powder and heating.

Production Method
A: components 1 to 4 were mixed and component 5 was added with mixing and dispersing to homogeneity.
B: components 6 to 8 were mixed.
C: B was gradually added to A with emulsification, and component 9 was thereafter added with mixing to obtain the eyeliner.

The eyeliner obtained in this manner was easy to spread and easy to draw with, did not blot or run, and had a use sensation free of stickiness; it was found to be free of changes due to temperature or elapsed time, to have a very good usability and stability, to exhibit both an excellent water resistance and an excellent perspiration resistance, and to be a very long-lasting cosmetic.

Example 22

Eye shadow with the following composition was prepared by the method described below.

TABLE 3

| | component | weight % |
|---|---|---|
| 1 | decamethylcyclopentasiloxane | 15 |
| 2 | dimethylpolysiloxane (6.0 mm$^2$/s) | 10 |
| 3 | polyether-modified dimethylpolysiloxane prepared in Example 18 | 2 |
| 4 | PEG (10) lauryl ether | 0.5 |
| 5 | silicone-treated chromium oxide* | 6.2 |
| 6 | silicone-treated ultramarine* | 4 |
| 7 | silicone-treated titanium-coated mica* | 6 |
| 8 | sodium chloride | 2 |
| 9 | propylene glycol | 8 |
| 10 | preservative | suitable amount |
| 11 | fragrance | suitable amount |
| 12 | purified water | balance |

Note.
The silicone-treated chromium oxide, silicone-treated ultramarine, and silicone-treated titanium-coated mica were each prepared by mixing 3 weight % methylhydrogenpolysiloxane into the particular powdered pigment and heating.

Production Method
A: components 1 to 4 were mixed and components 5 to 7 were added with dispersing to homogeneity.
B: components 8 to 10 and 12 were dissolved to homogeneity.
C: while stirring, B was gradually added to A with emulsification and component 11 was then added with mixing to produce the eye shadow.

The eye shadow obtained in this manner was easy to spread out and provided a use sensation that was free of greasiness and chalkiness; had a good water resistance, water repellency, and perspiration resistance; and was found to have a good wearing durability, to be resistant to disarrangement and exfoliation, and to be free of changes due to temperature and elapsed time and thus to also have an excellent stability.

Example 23

Suntan lotion with the following composition was prepared by the method described below.

TABLE 4

| | component | weight % |
|---|---|---|
| 1 | emulsifying agent composition* | 6 |
| 2 | dimethylpolysiloxane (20.0 mm$^2$/s) | 49 |
| 3 | 1,3-butylene glycol | 5 |
| 4 | sodium dehydroacetate | suitable amount |
| 5 | oxidation inhibitor | suitable amount |
| 6 | preservative | suitable amount |
| 7 | fragrance | suitable amount |
| 8 | purified water | balance |

Note.
The emulsifying agent composition comprised
a. 10 weight parts polyether-modified dimethylpolysiloxane obtained in Example 18,
b. 10 weight parts dioctadecyldimethylammonium salt-modified montmorillonite,
c. 40 weight parts ethanol, and
d. 40 weight parts purified water.

Production Method
A: component a. was dissolved in component c. and component b. was added.
B: A was stirred for 1 hour with a disperser; this was followed by removal of the ethanol with an evaporator.
C: B was dried for 24 hours at 50° C. to obtain the emulsifying agent composition of component 1.
D: Component 2 and the component 1 obtained in C were mixed.
E: Components 3 to 6 and 8 were mixed to homogeneity.
F: While stirring, E was gradually added to D with emulsification and component 7 was then added with mixing to obtain the suntan lotion.

The suntan lotion obtained in this manner had a fine texture and was easy to spread out, was not sticky or greasy, and provided a moisturizing, revitalizing, and refreshing use sensation, and was found to have good water resistance and wearing durability and to be free of changes due to temperature and elapsed time and thus to also have an excellent stability.

Example 24

A foundation with the following composition was prepared by the method described below.

TABLE 5

| | component | weight % |
|---|---|---|
| 1 | decamethylcyclopentasiloxane | 30 |
| 2 | dodecamethylcyclohexasiloxane | 10 |
| 3 | propyltrimethylsiloxyhexamethyltrisiloxane | 5 |
| 4 | dimethylpolysiloxane (6.0 mm²/s) | 5 |
| 5 | polyether-modified dimethylpolysiloxane obtained in Example 18 | 1.5 |
| 6 | polyether-modified dimethylpolysiloxane obtained in Example 19 | 0.5 |
| 7 | octadecyldimethylbenzylammonium salt-modified montmorillonite | 4 |
| 8 | hydrophobicized titanium oxide* | 10 |
| 9 | hydrophobicized talc oxide* | 6 |
| 10 | hydrophobicized mica oxide* | 6 |
| 11 | hydrophobicized red iron oxide* | 1.6 |
| 12 | hydrophobicized iron oxide yellow* | 0.7 |
| 13 | hydrophobicized iron oxide black* | 0.2 |
| 14 | dipropylene glycol | 5 |
| 15 | methyl para-oxybenzoate | 0.3 |
| 16 | 2-amino-2-methyl-1,3-propanediol | 0.2 |
| 17 | hydrochloric acid | 0.1 |
| 18 | fragrance | suitable amount |
| 19 | purified water | balance |

*Hydrophobicization was carried out by mixing 2 weight % decyltriethoxysilane into the particular pigment powder and heating.

Production Method

A: components 1 to 7 were mixed with heating; components 8 to 13 were added; and a uniform mixture was prepared.
B: Components 14 to 17 and 19 were dissolved with heating. (pH of the aqueous system=9.0)
C: While stirring, B was gradually added to A with emulsification; after cooling, component 18 was added with mixing to give the foundation.

The foundation obtained in this manner had a fine texture and was easy to spread out, was not sticky or greasy, and provided a moisturizing, revitalizing, and refreshing use sensation, and was found to have a good wearing durability and to be free of changes due to temperature and elapsed time and thus to also have an excellent stability.

Example 25

A hair cream with the following composition was prepared by the method described below.

TABLE 6

| | component | weight % |
|---|---|---|
| 1 | decamethylcyclopentasiloxane | 10 |
| 2 | methylphenylpolysiloxane (22.5 mm²/s) | 5 |
| 3 | squalane | 4 |
| 4 | silicone resin* | 1 |
| 5 | glyceryl dioleate | 2 |

TABLE 6-continued

| | component | weight % |
|---|---|---|
| 6 | polyether-modified dimethylpolysiloxane obtained in Example 18 | 4 |
| 7 | sodium sorbitol sulfate | 1 |
| 8 | sodium chondroitin sulfate | 1 |
| 9 | sodium hyaluronate | 0.5 |
| 10 | propylene glycol | 3 |
| 11 | preservative | 1.5 |
| 12 | vitamin E acetate | 0.1 |
| 13 | antioxidant | suitable amount |
| 14 | fragrance | suitable amount |
| 15 | purified water | balance |

*silicone resin: 50 weight % decamethylcyclopentasiloxane solution of a methylpolysiloxane resin with a [Me₃SiO₁/₂]/[SiO₂] ratio of 1.0.

Production Method

A: components 1 to 6 and components 11 to 13 were mixed with heating.
B: components 7 to 10 and component 15 were dissolved with heating.
C: While stirring, B was gradually added to A with emulsification; after cooling, component 14 was added with mixing to give the hair cream.

The hair cream obtained in this manner was easy to spread out, was not sticky or greasy, and provided a moisturizing use sensation, and was found to be water resistant, water repellent, and perspiration resistant, to have a good wearing durability, and to be free of changes due to temperature and elapsed time and thus to also have an excellent stability.

Example 26

A hand cream with the following composition was prepared by the method described below.

TABLE 7

| | component | weight % |
|---|---|---|
| 1 | decamethylcyclopentasiloxane | 30 |
| 2 | liquid paraffin | 10 |
| 3 | polypropylsilsesquioxane | 5 |
| 4 | dimethylpolysiloxane (6 mm²/s) | 10 |
| 5 | polyether-modified dimethylpolysiloxane obtained in Example 18 | 4 |
| 6 | distearyldimethylammonium chloride | 0.8 |
| 7 | vitamin E acetate | 0.1 |
| 8 | polyethylene glycol 4000 | 1 |
| 9 | glycerol | 10 |
| 10 | aluminum magnesium silicate | 1.2 |
| 11 | preservative | suitable amount |
| 12 | fragrance | suitable amount |
| 13 | purified water | balance |

Production Method

A: components 1 and 4 were dissolved with heating and mixing, and components 2, 3, 5 to 7, and 11 were added with heating.
B: components 8 to 10 and component 13 were mixed with heating.
C: B was gradually added to A with emulsification, followed by cooling and the addition of component 12 with mixing to give the hand cream.

The hand cream obtained in this manner was not sticky and was easy to spread out and had a refreshing use sensation, and was found to effectively protect the skin from wet work and to have an extremely good temperature stability.

Example 27

An antiperspirant with the following composition was prepared by the method described below.

TABLE 8

| | component | weight % |
|---|---|---|
| 1 | decamethylcyclopentasiloxane | 20 |
| 2 | 3-propylheptamethyltrisiloxane | 10 |
| 3 | polyether-modified dimethylpolysiloxane obtained in Example 18 | 1 |
| 4 | polyoxyethylene sorbitan monooleate | 0.5 |
| 5 | glycine salt of aluminum zirconium tetrachlorhydrate | 20 |
| 6 | purified water | balance |

Production Method

A: components 1 to 3 were mixed.

B: component 5 was dissolved in component 6 and component 4 was then added.

C: while stirring, B was gradually added to A with emulsification to give the antiperspirant.

The antiperspirant obtained in this manner was not sticky or greasy and had little whitening action and had a refreshing use sensation, and was found to be free of changes due to temperature and elapsed time and thus to also have an extremely good stability.

Example 28

A reconditioning lotion with the following composition was prepared by the method described below.

TABLE 9

| | component | weight % |
|---|---|---|
| 1 | decamethylcyclopentasiloxane | 12 |
| 2 | glyceryl triisoctanoate | 10 |
| 3 | polyether-modified dimethylpolysiloxane obtained in Example 18 | 2 |
| 4 | polyether-modified dimethylpolysiloxane obtained in Example 19 | 0.9 |
| 5 | glycerol | 0.8 |
| 6 | magnesium ascorbate phosphate | 3 |
| 7 | sodium chloride | 21 |
| 8 | preservative | suitable amount |
| 9 | fragrance | suitable amount |
| 10 | purified water | balance |

Production Method

A: components 1 to 4 were mixed with heating.

B: components 5 to 8 and component 10 were heated and dissolved to homogeneity.

C: while stirring, B was gradually added to A with emulsification, followed by cooling and the addition of component 9 to give the reconditioning lotion.

The reconditioning lotion obtained in this manner was easy to spread out, was not sticky, and was moisturizing and revitalizing, and was found to be free of changes due to temperature and elapsed time and thus to also have an extremely good stability.

Example 29

A cleansing cream with the following composition was prepared by the method described below.

TABLE 10

| | component | weight % |
|---|---|---|
| 1 | dimethylpolysiloxane (6.0 mm$^2$/s) | 5 |
| 2 | methylphenylpolysiloxane (22.5 mm$^2$/s) | 5 |
| 3 | liquid paraffin | 8 |
| 4 | jojoba oil | 2 |
| 5 | polyether-modified dimethylpolysiloxane obtained in Example 18 | 2.5 |
| 6 | polyether-modified dimethylpolysiloxane obtained in Example 19 | 0.5 |
| 7 | dextrin fatty acid ester | 0.8 |
| 8 | aluminum monostearate | 0.2 |
| 9 | aluminum chloride | 1 |
| 10 | glycerol | 10 |
| 11 | preservative | suitable amount |
| 12 | fragrance | suitable amount |
| 13 | purified water | balance |

Production Method

A: components 1 to 8 were mixed with heating.

B: components 9 to 11 and component 13 were heated and dissolved.

C: while stirring, B was gradually added to A with emulsification, followed by cooling and the addition of component 12 to give the cleansing cream.

The cleansing cream obtained in this manner had a fine texture, was easy to spread out, was not sticky or greasy, and provided a moisturizing, revitalizing, and refreshing use sensation, and was found to have a strong cleansing effect and to be free of changes due to temperature and elapsed time and thus to also have an excellent stability.

Example 30

A rinse-type pack cosmetic with the following composition was prepared by the method described below.

TABLE 11

| | component | weight % |
|---|---|---|
| 1 | dimethylpolysiloxane (6.0 mm$^2$/s) | 3 |
| 2 | polyether-modified dimethylpolysiloxane obtained in Example 18 | 2 |
| 3 | kaolin | 30 |
| 4 | carboxyvinyl polymer | 0.4 |
| 5 | 1,3-butylene glycol | 10 |
| 6 | glycerol | 20 |
| 7 | preservative | suitable amount |
| 8 | fragrance | suitable amount |
| 9 | purified water | balance |

Production Method

A: components 1, 2, and 8 were mixed.

B: components 4 to 7 and 9 were mixed to homogeneity, after which component 3 was admixed with stirring.

C: A was added to B and emulsification was carried out to give a rinse-type pack cosmetic in the form of paste.

The rinse-type pack cosmetic obtained in this manner was easy to spread out during application and had an excellent cleaning effect. After rinsing off, it was found that the skin had a smooth, moisturized feel without stickiness, the use sensation was quite good, and the stability was also excellent.

Example 31

A wipe-off cleanser with the following composition was prepared by the method described below.

TABLE 12

| | component | weight % |
|---|---|---|
| 1 | squalane | 10 |
| 2 | liquid paraffin | 28 |
| 3 | low-density polyethylene | 2 |
| 4 | polyether-modified dimethylpolysiloxane obtained in Example 18 | 2 |
| 5 | propylene glycol | 5 |
| 6 | antioxidant | suitable amount |
| 7 | preservative | suitable amount |
| 8 | fragrance | suitable amount |
| 9 | purified water | balance |

Production Method

A: components 1 to 4 and components 6 to 8 were mixed with heating.

B: components 5 and 9 were mixed with heating, after which they were added to A while stirring; emulsification then gave the wipe-off cleanser.

During application, the wipe-off cleanser obtained in this manner was not sticky and was also easy to spread out and had a moisturizing effect. After wiping off, the condition was very good, with a moisturizing effect without stickiness. Also, there were no changes due to temperature or elapsed time and the stability was thus also excellent.

Example 32

A deodorant with the following composition was prepared by the method described below.

TABLE 13

| | component | weight % |
|---|---|---|
| 1 | decamethylcyclopentasiloxane | 12 |
| 2 | dimethylpolysiloxane (6.0 mm$^2$/s) | 4 |
| 3 | polyether-modified dimethylpolysiloxane obtained in Example 18 | 1 |
| 4 | propylene glycol | 31 |
| 5 | triclosan | 10 |
| 6 | glycerol | 20 |
| 7 | preservative | suitable amount |
| 8 | fragrance | suitable amount |
| 9 | purified water | balance |

Production Method

A: components 1 to 3 were mixed.

B: component 5 was dissolved in component 4, followed by the admixture of components 6 to 9.

C: while vigorously stirring A, B was added and emulsification was carried out.

D: 65 parts C was added to an aerosol can; 35 parts propellant (mixture of n-butane, isobutane, and propane) was added; and the can was sealed to give the deodorant.

The deodorant obtained in this manner was found to have an extremely good usability in that, even when used at a high concentration, it did not drip and also was not sticky, while being light and having a very good persistence of effect.

Example 33

A makeup remover with the following composition was prepared by the method described below.

TABLE 14

| | component | weight % |
|---|---|---|
| 1 | polyether-modified dimethylpolysiloxane obtained in Example 18 | 20 |
| 2 | polyoxyethylene (20) sorbitan monostearate | 10 |
| 3 | sorbitol | 10 |
| 4 | carrageenan | 0.5 |
| 5 | preservative | suitable amount |
| 6 | fragrance | suitable amount |
| 7 | purified water | balance |

Production Method

A: components 1 to 5 and component 7 were combined with dissolution to homogeneity.

B: component 6 was added to A with mixing to give the makeup remover.

When the makeup remover obtained in this manner was used to remove a longlasting foundation, it had a good affinity with the foundation and sebum and had an extremely good dirt removal performance. It was easy to spread at the time of use, and after use was not sticky and left the skin refreshed; it was thus a makeup remover with both an extremely good usability and an extremely good use sensation. In addition, it was found to be free of changes due to temperature and elapsed time and thus also had an excellent stability.

Example 34

Sunscreen lotion with the following composition was prepared by the method described below.

TABLE 15

| | component | weight % |
|---|---|---|
| 1 | decamethylcyclopentasiloxane | 5 |
| 2 | silicone resin (50% decamethylpentasiloxane solution) | 5 |
| 3 | 2-ethylhexyl para-methoxycinnamate | 10 |
| 4 | polyether-modified dimethylpolysiloxane obtained in Example 18 | 2 |
| 5 | decamethylcyclopentasiloxane dispersion of 40% microgranular titanium oxide | 5 |
| 6 | decamethylcyclopentasiloxane dispersion of 40% microgranular zinc oxide | 5 |
| 7 | 1,3-butylene glycol | 3 |
| 8 | polysorbate 20 | 0.4 |
| 9 | sodium chloride | 2 |
| 10 | purified water | 56.9 |
| 11 | preservative | 0.5 |
| 12 | fragrance | 0.2 |

Production Method

A: components 1 to 6 are mixed to homogeneity.

B: components 7 to 11 are mixed to homogeneity.

C: while stirring, B is gradually added to A with emulsification and component 12 is subsequently added with mixing to give the sunscreen lotion.

The sunscreen lotion obtained in this manner had a fine texture and could be easily spread; it was not sticky or greasy and provided a refreshing sensation; it had a very durable water resistance; and it was free of changes due to temperature and elapsed time and thus also had an excellent stability.

INDUSTRIAL APPLICABILITY

The polyether-modified organopolysiloxane of the present invention and the diorganopolysiloxane-polyether block copolymer of the present invention, because they are modified with polyglycidyl ether or glycidyl ether.alkylene oxide copolymer, are useful, for example, as surfactants, emulsifying agents, dispersing agents, foam regulators, antifoams, fiber and textile treatment agents, cosmetic components, components for drugs for topical application to the skin, and so forth. In particular, the polyether-modified organopolysiloxane modified with only polyglycidyl ether and the diorganopolysiloxane-polyether block copolymer modified with only polyglycidyl ether are both more resistant to oxidation in air than the usual polyoxyalkylene-modified organopolysiloxanes and are thus more resistant to producing carbonyl-functional allergenically antigenic compounds (typified by formaldehyde) with elapsed time; as a consequence they are well-qualified as cosmetic components and components of drugs for topical application to the skin. The methods of the present invention for producing the polyether-modified organopolysiloxane and the diorganopolysiloxane-polyether block copolymer are useful for producing the aforementioned polyether-modified organopolysiloxane and diorganopolysiloxane-polyether block copolymer at good productivities. The cosmetic of the present invention is useful as a cosmetic that is in direct contact with human skin or human hair.

What is claimed:

1. A polyether-modified organopolysiloxane represented by the average unit formula (1)

{in the formula, $R^1$ is selected from the group consisting of a monovalent hydrocarbyl group that does not contain an aliphatically unsaturated bond, a monovalent fluorohydrocarbyl group that does not contain an aliphatically unsaturated bond, and an organic group represented by general formula (2)

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, Z is an alkyleneoxy group, m is 0-200, Y is hydrogen atom or is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and a glycidyl group, and p is an integer from 1 to 6]

wherein at least 80 mol % of $R^1$ in the molecule is a monovalent hydrocarbyl group that does not contain an aliphatically unsaturated bond;

$R^2$ is an organic group represented by general formula (3)

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, Z is an alkyleneoxy group, n is 1-200, m is 0-200, n and m satisfy $0.5<n/(n+m)\leq 1$, Y is a hydrogen atom or is a group selected from a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and a glycidyl group, p is an integer from 1 to 6, X is a divalent group represented by general formula (4) or general formula (5)

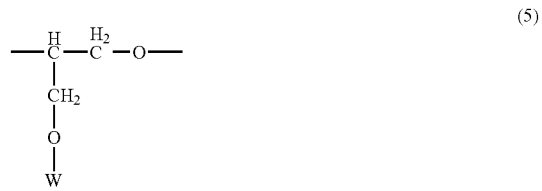

(in the preceding formulas, W is a monovalent hydrocarbyl group that does not contain an aliphatically unsaturated bond or is a monovalent fluorohydrocarbyl group that does not contain an aliphatically unsaturated bond), wherein the configuration of the X and Z groups may be random, block, alternating, or a combination of the preceding];

a has an average value of $1.0\leq a\leq 2.5$; b has an average value of $0.001\leq b\leq 1.5$; and a and b satisfy an average of $1.001\leq a+b\leq 3.0$}.

2. The polyether-modified organopolysiloxane according to claim 1, wherein in average unit formula (1), 100 mol % of the silicon-bonded $R^1$ is a monovalent hydrocarbyl group that does not contain an aliphatically unsaturated bond; $R^3$ is an alkylene group or alkyleneoxyalkylene group having 2 to 20 carbon atoms, Z is an alkyleneoxy group having 2 to 6 carbon atoms; Y is hydrogen atom, an alkyl group having no more than 20 carbon atoms, or a saturated aliphatic acyl group having no more than 20 carbon atoms; W in the group X is an alkyl group; and p is 1 or 2.

3. The polyether-modified organopolysiloxane according to claim 2, wherein the monovalent hydrocarbyl group that does not contain an aliphatically unsaturated bond constituting $R^1$ is methyl; the alkylene group constituting $R^3$ is propylene or butylene; the alkyleneoxyalkylene group constituting $R^3$ is propyleneoxyethylene, ethyleneoxyethylene, propyleneoxypropylene, a group represented by formula (20), or a group represented by formula (21);

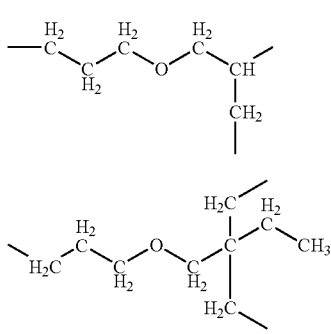

(20)

(21)

and the alkyl group constituting W in the group X is an alkyl group having 1 to 4 carbon atoms.

4. The polyether-modified organopolysiloxane according to claim 1, wherein n and m satisfy $0.9 \leq n/(n+m) \leq 1$.

5. The polyether-modified organopolysiloxane according to claim 4, wherein $m=0$ and $n/(n+m)=1$.

6. A method of producing the polyether-modified organopolysiloxane of claim 1, comprising
carrying out a hydrosilylation reaction between
(a) a silicon-bonded hydrogen atom-containing organopolysiloxane represented by average unit formula (6)

$$R^1{}_a H_b SiO_{(4-a-b)/2} \qquad (6)$$

($R^1$, a, and b in the formula are defined as in claim 1) and
(b) a double bond-terminated polyether represented by general formula (7)

$$R(\text{---}O\text{---}X_n\text{---}Z_m\text{---}Y)_p \qquad (7)$$

[in the formula, R is a double bond-terminated p-valent hydrocarbyl group having 2 to 20 carbon atoms or a group comprising said hydrocarbyl group having an ether linkage (C—O—C) therein, and X, n, Z, m, Y, p, and the configuration of X and Z groups are defined as in claim 1]
in the presence of
(c) a hydrosilylation reaction catalyst.

7. The polyether-modified organopolysiloxane according to claim 1, wherein the polyether-modified organopolysiloxane is represented by average structural formula (8)

$$A[(R^6)_2SiO]_x[(R^6)(R^2)SiO]_y Si(R^6)_2 A \qquad (8)$$

{in the formula, $R^6$ is a monovalent hydrocarbyl group that does not contain an aliphatically unsaturated bond; $R^2$ is an organic group represented by general formula (3)

$$\text{---}R^3(\text{---}O\text{---}X_n\text{---}Z_m\text{---}Y)_p \qquad (3)$$

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above (wherein W in the group X is an alkyl group), Z is an alkyleneoxy group having 2 to 6 carbon atoms, n is 1-200, m is 0-200, n and m satisfy $0.5<n/(n+m) \leq 1$, Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond, and p is an integer from 1 to 6, wherein the configuration of the X and Z groups may be random, block, alternating, or a combination of the preceding];
A is $R^6$ or $R^2$; x is 0-500; y is 0-100; x+y is 1-600; and when y is 0, at least one of A is $R^2$}.

8. The polyether-modified organopolysiloxane according to claim 7, wherein at least 50 mol % of the monovalent hydrocarbyl group that does not contain an aliphatically unsaturated bond constituting $R^6$ is methyl; $R^3$ is an alkylene group or alkyleneoxyalkylene group having 2 to 20 carbon atoms; Z is an alkyleneoxy group having 2 or 3 carbon atoms; Y is hydrogen atom; W in the group X is an alkyl group having 1 to 4 carbon atoms; and p is 1 or 2.

9. The polyether-modified organopolysiloxane according to claim 8, wherein the monovalent hydrocarbyl group that does not contain an aliphatically unsaturated bond constituting $R^6$ is methyl; the alkylene group constituting $R^3$ is propylene or butylene; the alkyleneoxyalkylene group constituting $R^3$ is propyleneoxyethylene, ethyleneoxyethylene, propyleneoxypropylene, or a group represented by formula (20) or (21) given above; the alkyleneoxy group constituting Z is ethyleneoxy; and the alkyl group constituting W in the group X is methyl, ethyl, propyl, or butyl.

10. The polyether-modified organopolysiloxane according to claim 7, wherein n and m satisfy $0.9 \leq n/(n+m) \leq 1$.

11. The polyether-modified organopolysiloxane according to claim 10, wherein $m=0$ and $n/(n+m)=1$.

12. A method of producing the polyether-modified organopolysiloxane represented by average structural formula (8)

$$A[(R^6)_2SiO]_x[(R^6)(R^2)SiO]_y Si(R^6)_2 A \qquad (8)$$

{A, $R^6$, $R^2$, x, and y in the formula are defined as in claim 7}, comprising
carrying out a hydrosilylation reaction between
(a) a silicon-bonded hydrogen atom-containing organopolysiloxane represented by average structural formula (9)

$$B[(R^6)_2SiO]_x[(R^6)HSiO]_y Si(R^6)_2 B \qquad (9)$$

(in the formula, $R^6$ is a monovalent hydrocarbyl group that does not contain an aliphatically unsaturated bond, x is 0-500, y is 0-100, x+y is 1-600, and B is $R^6$ or H, wherein when y is 0 at least one of B is H) and
(b) a double bond-terminated polyether represented by general formula (7)

$$R(\text{---}O\text{---}X_n\text{---}Z_m\text{---}Y)_p \qquad (7)$$

{in the formula, R is a double bond-terminated p-valent hydrocarbyl group having 2 to 20 carbon atoms or a group comprising said hydrocarbyl group having an ether linkage (C—O—C) therein, X is a divalent group represented by general formula (4) or general formula (5) given above (wherein W in the group X is an alkyl group), and n, Z, m, Y, p, and the X and Z group configuration are defined as in claim 7}
in the presence of
(c) a hydrosilylation reaction catalyst.

13. The polyether-modified organopolysiloxane according to claim 1, wherein the polyether-modified organopolysiloxane is represented by average structural formula (10)

$$A[(R^6)_2SiO]_x[(R^6)(R^2)SiO]_y[(R^6)(R^7)SiO]_z Si(R^6)_2 A \qquad (10)$$

(in the formula, $R^6$ is a monovalent hydrocarbyl group that does not contain an aliphatically unsaturated bond; $R^2$ is an organic group represented by general formula (3)

$$-R^3(-O-X_n-Z_m-Y)_p \quad (3)$$

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above (wherein W in the group X is an alkyl group), Z is an alkyleneoxy group having 2 to 6 carbon atoms, n is 1-200, m is 0-200, n and m satisfy $0.5 < n/(n+m) \leq 1$, Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond, and p is an integer from 1 to 6, wherein the configuration of the X and Z groups may be random, block, alternating, or a combination of the preceding];

$R^7$ is an organic group represented by general formula (2)

$$-R^3(-O-Z_m-Y)_p \quad (2)$$

{in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, Z is an alkyleneoxy group having 2 to 6 carbon atoms, m is 0-200, Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond, and p is an integer from 1 to 6};

A is $R^6$ or $R^2$; x is 0-500; y is 0-100; z is 1-100; x+y+z is 1-600; and when y is 0, at least one of A is $R^2$).

14. The polyether-modified organopolysiloxane according to claim 13, wherein at least 50 mol % of the monovalent hydrocarbyl group that does not contain an aliphatically unsaturated bond constituting $R^6$ is methyl; $R^3$ is an alkylene or alkyleneoxyalkylene group having 2 to 20 carbon atoms; Z is an alkyleneoxy group having 2 or 3 carbon atoms; Y is hydrogen atom; W in the group X is an alkyl group having 1 to 4 carbon atoms; and p is 1 or 2.

15. The polyether-modified organopolysiloxane according to claim 14, wherein the monovalent hydrocarbyl group that does not contain an aliphatically unsaturated bond constituting $R^6$ is methyl; the alkylene group constituting $R^3$ is propylene or butylene; the alkyleneoxyalkylene group constituting $R^3$ is propyleneoxyethylene, ethyleneoxyethylene, propyleneoxypropylene, or a group represented by formula (20) or (21) given above; the alkyleneoxy group constituting Z is ethyleneoxy group; and the alkyl constituting W in the group X is methyl, ethyl, propyl, or butyl.

16. The polyether-modified organopolysiloxane according to claim 13, wherein n and m satisfy $0.9 \leq n/(n+m) \leq 1$.

17. The polyether-modified organopolysiloxane according to claim 16, wherein m=0 and n/(n+m)=1.

18. A method of producing the polyether-modified organopolysiloxane represented by average structural formula (10)

$$A[(R^6)_2SiO]_x[(R^6)(R^2)SiO]_y[(R^6)(R^7)SiO]_zSi(R^6)_2A \quad (10)$$

{A, $R^6$, $R^2$, $R^7$, x, y, and z in the formula are defined as in claim 13}, comprising carrying out a hydrosilylation reaction between (a) a silicon-bonded hydrogen atom-containing organopolysiloxane represented by average structural formula (11)

$$B[(R^6)_2SiO]_x[(R^6)HSiO]_{(y+z)}Si(R^6)_2B \quad (11)$$

(in the formula, $R^6$, x, y, and z are defined as in claim 13 and B is $R^6$ or H, wherein when y+z is 0 at least one of B is H)

and (b) a double bond-terminated polyether represented by general formula (7)

$$R(-O-X_n-Z_m-Y)_p \quad (7)$$

(in the formula, R is defined as in claim 12 and X, n, Z, m, Y, p, and the configuration of X and Z groups are defined as in claim 13) and (b-1) a double bond-terminated polyether represented by general formula (12)

$$R(-O-Z_m-Y)_p \quad (12)$$

(in the formula, R is defined as in claim 12 and Z, m, Y, and p are defined as in claim 13)

in the presence of (c) a hydrosilylation reaction catalyst.

19. A diorganopolysiloxane-polyether block copolymer, characterized in that the main chain thereof is represented by general formula (13)

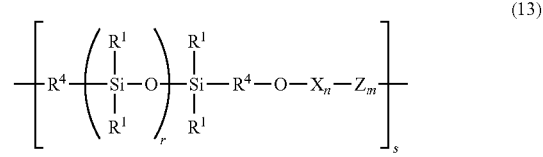

(in the formula, $R^1$ is a monovalent hydrocarbyl group that does not contain an aliphatically unsaturated bond or is a monovalent fluorohydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5)

-continued

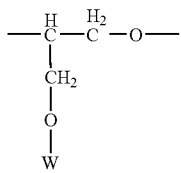
(5)

(in the preceding formulas, W is a monovalent hydrocarbly group that does not contain an aliphatically unsaturated bond or is a monovalent fluorohydrocarbly group that does not contain an aliphatically unsaturated bond), Z is an alkyleneoxy group, n is 1-200, m is 0-200, n and m satisfy $0.5<n/(n+m)\leq 1$, the configuration of the X and Z groups may be random, block, alternating, or a combination of the preceding, r is an integer from 1 to 1000, and s is an integer with a value of at least 2).

20. A diorganopolysiloxane-polyether block copolymer represented by average structural formula (14)

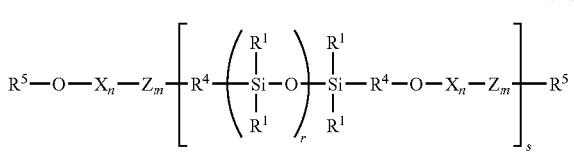
(14)

(in the formula, $R^1$ is a monovalent hydrocarbyl group that does not contain an aliphatically unsaturated bond or is a monovalent fluorohydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5)

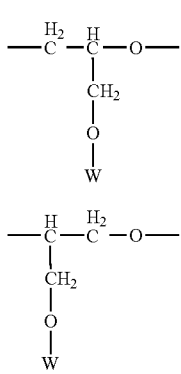
(4)

(5)

(in the preceding formulas, W is a monovalent hydrocarbly group that does not contain an aliphatically unsaturated bond or is a monovalent fluorohydrocarbly group that does not contain an aliphatically unsaturated bond), Z is an alkyleneoxy group, n is 1-200, m is 0-200, n and m satisfy $0.5<n/(n+m)\leq 1$, the configuration of the X and Z groups may be random, block, alternating, or a combination of the preceding, r is an integer from 1 to 1000, s is an integer with a value of at least 2, and $R^5$ is a double bond-terminated monovalent hydrocarbyl group or a group comprising said hydrocarbyl group having an ether linkage (C—O—C) therein).

21. The diorganopolysiloxane-polyether block copolymer according to claim 19 or 20, wherein $R^1$ is a monovalent hydrocarbyl group that does not contain an aliphatically unsaturated bond and at least 50 mol % thereof is methyl; the divalent hydrocarbyl group having 2 to 20 carbon atoms that does not contain an aliphatically unsaturated bond or a group comprising said hydrocarbyl group having an ether linkage (C—O—C) therein, i.e., $R^4$ is an alkylene or alkyleneoxyalkylene group having 2 to 20 carbon atoms; Z is an alkyleneoxy group having 2 to 6 carbon atoms; and W in the group X is an alkyl group.

22. The diorganopolysiloxane-polyether block copolymer according to claim 21, wherein the monovalent hydrocarbyl group that does not contain an aliphatically unsaturated bond constituting $R^1$ is methyl; the alkylene group constituting $R^3$ or $R^4$ is propylene or butylene; the alkyleneoxyalkylene group constituting $R^3$ or $R^4$ is propyleneoxyethylene, ethyleneoxyethylene, or propyleneoxypropylene; the alkyleneoxy group constituting Z is ethyleneoxy; and the alkyl group constituting W in the group X is methyl, ethyl, propyl, or butyl.

23. The diorganopolysiloxane-polyether block copolymer according to claim 19 or 20, wherein n for the group X and m for the group Z satisfy $0.9 \leq n/(n+m) \leq 1$.

24. The diorganopolysiloxane-polyether block copolymer according to claim 23, wherein m=0 and n/(n+m)=1.

25. A method of producing the diorganopolysiloxane-polyether block copolymer that has a main chain represented by general formula (13) that is defined in claim 19, comprising
carrying out a hydrosilylation reaction between
(d) a diorganopolysiloxane that has silicon-bonded hydrogen atoms at both terminals and that is represented by average structural formula (15)

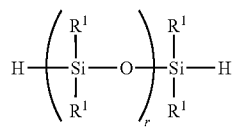
(15)

(in the formula, $R^1$ is a monovalent hydrocarbyl group that does not contain an aliphatically unsaturated bond or is a monovalent fluorohydrocarbyl group that does not contain an aliphatically unsaturated bond and r is an integer from 1 to 1000)
and
(e) a double bond-diterminated polyether that is represented by general formula (16)

(16)

(in the formula, $R^5$ is a double bond-terminated monovalent hydrocarbyl group having 2 to 20 carbon atoms or is a group comprising said hydrocarbyl group having an ether linkage (C—O—C) therein, X is a divalent group represented by general formula (4) or general formula (5) given above, Z is an alkyleneoxy group, n is 1-200, m is 0-200, and n and m satisfy $0.5 < n/(n+m) \leq 1$, wherein the configuration of the X and Z groups may be random, block, alternating, or a combination of the preceding) in the presence of (c) a hydrosilylation reaction catalyst.

26. The method of producing the diorganopolysiloxane-polyether block copolymer according to claim 25, wherein the diorganopolysiloxane-polyether block copolymer is represented by average structural formula (14)

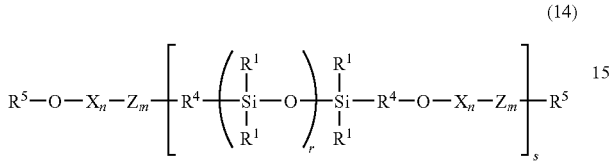

(14)

(in the formula, $R^1$ is a monovalent hydrocarbyl group that does not contain an aliphatically unsaturated bond or is a monovalent fluorohydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above, Z is an alkyleneoxy group, n is 1-200, m is 0-200, n and m satisfy $0.5 < n/(n+m) \leq 1$, the configuration of the X and Z groups may be random, block, alternating or a combination of the preceding r is an integer from 1 to 1000, s is an integer with a value of at least 2, and $R^5$ is a double bond-terminated monovalent hydrocarbyl group or a group comprising said hydrocarbyl group having an ether linkage (C—O—C) therein), and the method is characterized in that the hydrosilylation reaction is carried out at a ratio [(number of moles of polyether represented by general formula (16))/(number of moles of diorganopolysiloxane represented by average structural formula (15))] that is larger than 1.0 and no larger than 1.2.

27. A diorganopolysiloxane-polyether block copolymer represented by average structural formula (17)

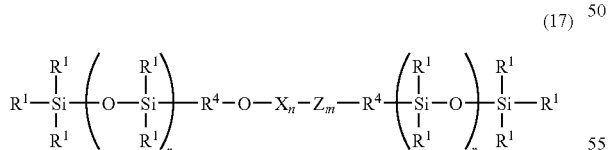

(17)

(in the formula, $R^1$ is a monovalent hydrocarbyl group that does not contain an aliphatically unsaturated bond or is a monovalent fluorohydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5)

(4)

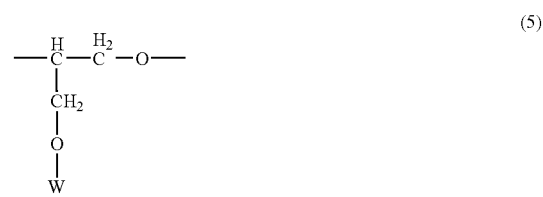

(5)

(in the preceding formulas, W is a monovalent hydrocarbyl group that does not contain an aliphatically unsaturated bond or is a monovalent fluorohydrocarbyl group that does not contain an aliphatically unsaturated bond), Z is an alkyleneoxy group, n is 1-200, m is 0-200, n and m satisfy $0.5 < n/(n+m) \leq 1$, r is an integer from 1 to 1000, and the configuration of the X and Z groups may be random, block, alternating, or a combination of the preceding).

28. A method of producing the diorganopolysiloxane-polyether block copolymer represented by average structural formula (17) that is defined in claim 27, comprising carrying out a hydrosilylation reaction between (f) a diorganopolysiloxane that has a silicon-bonded hydrogen atom at one terminal and that is represented by average structural formula (18)

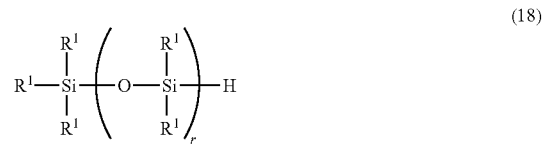

(18)

(in the formula, $R^1$ is a monovalent hydrocarbyl group that does not contain an aliphatically unsaturated bond or is a monovalent fluorohydrocarbyl group that does not contain an aliphatically unsaturated bond and r is an integer from 1 to 1000)

and (e) a double bond-terminated polyether that is represented by general formula (16)

$R^5$—O—$X_n$—$Z_m$—$R^5$ (16)

(in the formula, $R^5$, X, n, Z, m, and the configuration of X and Z groups are defined as in claim 25)

in the presence of (c) a hydrosilylation reaction catalyst at a ratio [(number of moles of polyether represented by general formula (16))/(number of moles of diorganopolysiloxane represented by average structural formula (18)×2)] that is larger than 1.0 and no larger than 1.2.

29. A diorganopolysiloxane-polyether block copolymer represented by average structural formula (19)

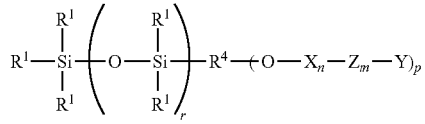
(19)

(in the formula, $R^1$ is a monovalent hydrocarbyl group that does not contain an aliphatically unsaturated bond or is a monovalent fluorohydrocarbyl group that does not contain an aliphatically unsaturated bond; $R^4$ is a (p+1)-valent hydrocarbyl group having 2 to 20 carbon atoms that does not contain an aliphatically unsaturated bond or is a group comprising said hydrocarbyl group having an ether linkage (C—O—C) therein; r is an integer from 1 to 1000; X is a divalent group represented by general formula (4) or general formula (5)

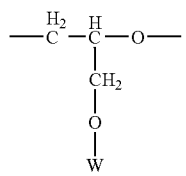
(4)

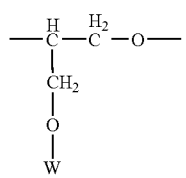
(5)

(in the preceding formulas, W is a monovalent hydrocarbyl group that does not contain an aliphatically unsaturated bond or is a monovalent fluorohydrocarbyl group that does not contain an aliphatically unsaturated bond), Z is an alkyleneoxy group; n is 1-200; m is 0-200; n and m satisfy $0.5 < n/(n+m) \leq 1$; Y is hydrogen atom or is a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and a glycidyl group; p is an integer from 1 to 6, and the configuration of the X and Z groups may be random, block, alternating, or a combination of the preceding).

30. A method of producing the diorganopolysiloxane-polyether block copolymer according to claim 29, comprising carrying out a hydrosilylation reaction between (f) a diorganopolysiloxane that has a silicon-bonded hydrogen atom at one terminal and that is represented by average structural formula (18)

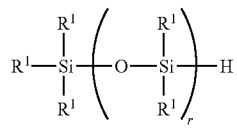
(18)

(in the formula, $R^1$ is a monovalent hydrocarbyl group that does not contain an aliphatically unsaturated bond or is a monovalent fluorohydrocarbyl group that does not contain an aliphatically unsaturated bond and r is an integer from 1 to 1000)

and (b) a double bond-terminated polyether represented by general formula (7)

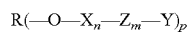
(7)

(in the formula, R is a double bond-terminated p-valent hydrocarbyl group having 2 to 20 carbon atoms or a group comprising said hydrocarbyl group having an ether linkage (C—O—C) therein, X is a divalent group represented by general formula (4) or general formula (5) given above, Z is an alkyleneoxy group, n is 1-200, m is 0-200, n and m satisfy $0.5 < n/(n+m) \leq 1$, Y is a hydrogen atom or a group selected from the group consisting of a monovalent hydrocarbyl group that contains no more than 20 carbon atoms and that does not contain an aliphatically unsaturated bond, an acyl group that contains no more than 20 carbon atoms and that does not contain an aliphatically unsaturated bond, and a glycidyl group, p is an integer from 1 to 6, and the configuration of the X and Z groups may be random, block, alternating, or a combination of the preceding)

in the presence of (c) a hydrosilylation reaction catalyst at a ratio [(number of moles of polyether represented by general formula (7))/(number of moles of diorganopolysiloxane represented by average structural formula (18))] that is larger than 1.0 and no larger than 1.2.

31. A diorganopolysiloxane-polyether block copolymer characterized in that its main chain is represented by general formula (59)

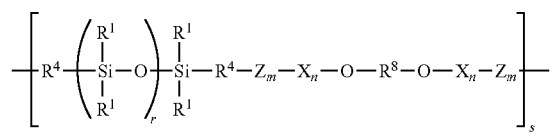
(59)

(in the formula, $R^1$ is a monovalent hydrocarbyl group that does not contain an aliphatically unsaturated bond or is a monovalent fluorohydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, $R^8$ is a divalent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5)

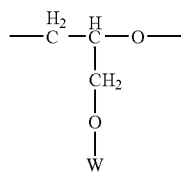 (4)

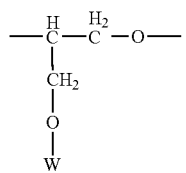 (5)

(in the preceding formulas, W is a monovalent hydrocarbyl group that does not contain an aliphatically unsaturated bond or is a monovalent fluorohydrocarbyl group that does not contain an aliphatically unsaturated bond), Z is an alkyleneoxy group, n is 1-200, m is 0-200, n and m satisfy $0.5 < n/(n+m) \leq 1$, the configuration of the X and Z groups may be random, block, alternating, or a combination of the preceding, r is an integer from 1 to 1000, and s is an integer with a value of at least 2).

32. A diorganopolysiloxane-polyether block copolymer represented by average structural formula (60)

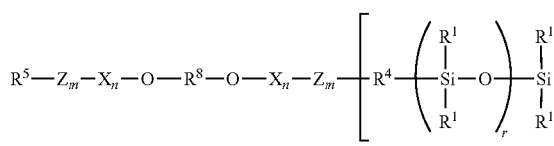 (60)

(in the formula, $R^1$ is a monovalent hydrocarbyl group that does not contain an aliphatically unsaturated bond or is a monovalent fluorohydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, $R^5$ is a double bond-terminated monovalent hydrocarbyl group having 2 to 20 carbon atoms or is a group comprising said hydrocarbyl group having an ether linkage (C—O—C) therein, $R^8$ is a divalent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5)

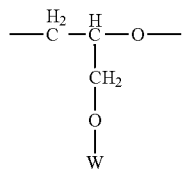 (4)

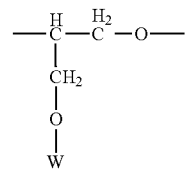 (5)

(in the preceding formulas, W is a monovalent hydrocarbyl group that does not contain an aliphatically unsaturated bond or is a monovalent fluorohydrocarbyl group that does not contain an aliphatically unsaturated bond), Z is an alkyleneoxy group, n is 1-200, m is 0-200, n and m satisfy $0.5 < n/(n+m) \leq 1$, the configuration of the X and Z groups may be random, block, alternating, or a combination of the preceding, r is an integer from 1 to 1000, and s is an integer with a value of at least 2).

33. A method of producing the diorganopolysiloxane-polyether block copolymer represented by general formula (59) that is defined in claim 31, comprising
carrying out a hydrosilylation reaction between (d) a diorganopolysiloxane that has silicon-bonded hydrogen atoms at both terminals and that is represented by average structural formula (15)

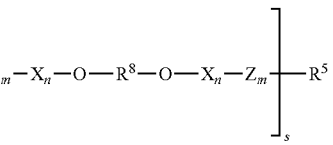 (15)

(in the formula, $R^1$ is a monovalent hydrocarbyl group that does not contain an aliphatically unsaturated bond or is a monovalent fluorohydrocarbyl group that does not contain an aliphatically unsaturated bond and r is an integer from 1 to 1000)
and
(g) a double bond-ditterminated polyether that is represented by general formula (61)

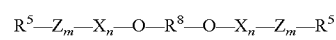 (61)

(in the formula, $R^5$ is a double bond-terminated monovalent hydrocarbyl group having 2 to 20 carbon atoms or is a group comprising said hydrocarbyl group having an ether linkage (C—O—C) therein, $R^8$ is a divalent hydrocarbyl group having 2 to 20 carbon atoms that does not contain an aliphatically unsaturated bond or is a divalent group comprising said hydrocarbyl group having an ether linkage (C—O—C) therein, X is a divalent group represented by general formula (4) or general formula (5) given above, Z is an alkyleneoxy group, n is 1-200, m is 0-200, and n and m satisfy $0.5<n/(n+m)\leq 1$, wherein the configuration of the X and Z groups may be random, block, alternating, or a combination of the preceding) in the presence of (c) a hydrosilylation reaction catalyst.

34. The method of producing the diorganopolysiloxane-polyether block copolymer according to claim 33, wherein the diorganopolysiloxane-polyether block copolymer is represented by average structural formula (60)

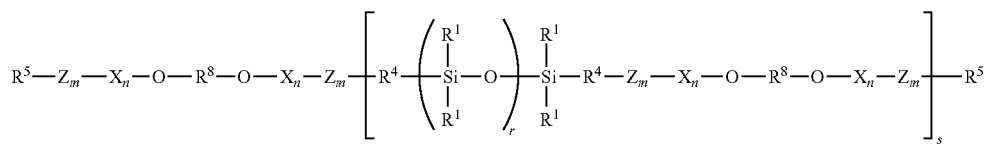

(in the formula, $R^1$ is a monovalent hydrocarbyl group that does not contain an aliphatically unsaturated bond or is a monovalent fluorohydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, $R^5$ is a double bond-terminated monovalent hydrocarbyl group having 2 to 20 carbon atoms or is a group comprising said hydrocarbyl group having an ether linkage (C—O—C) therein, $R^8$ is a divalent hydrocarbyl group having 2 to 20 carbon atoms that does not contain an aliphatically unsaturated bond or is a group comprising said hydrocarbyl group having an ether linkage (C—O—C) therein, X is a divalent group represented by general formula (4) or general formula (5) given above, Z is an alkyleneoxy group, n is 1-200, m is 0-200, n and m satisfy $0.5<n/(n+m)\leq 1$, the configuration of the X and Z groups may be random, block, alternating or a combination of the preceding, r is an integer from 1 to 1000, and s is an integer with a value of at least 2), and wherein the reaction is carried out at a ratio [(number of moles of double bond-diterminated polyether represented by general formula (61))/(number of moles of diorganopolyorganosiloxane that has silicon-bonded hydrogen atoms at both terminals and that is represented by average structural formula (15))] that is larger than 1.0 and no larger than 1.2.

35. The method of producing polyether-modified organopolysiloxane according to claim 6, wherein the hydrosilylation reaction catalyst (c) is a platinum compound catalyst.

36. The method of producing diorganopolysiloxane-polyether block copolymer according to claim 25, wherein the hydrosilylation reaction catalyst (c) is a platinum compound catalyst.

37. A cosmetic that contains at least one selection from the group consisting of the polyether-modified organopolysiloxanes and the diorganopolysiloxane-polyether block copolymers listed below:

a polyether-modified organopolysiloxane represented by average unit formula (1), $$R^1{}_a R^2{}_b SiO_{(4-a-b)/2} \quad (1)$$

wherein $R^1$ is a monovalent hydrocarbyl group that does not contain an aliphatically unsaturated bond;

$R^2$ is an organic group represented by formula (3)

$$-R^3(-O-X_n-Z_m-Y)_p \quad (3)$$

[in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, Z is an oxyalkylene group having 2 to 6 carbon atoms, n is 1-200, m is 0-200, n and m satisfy $0.9 \leq n/(n+m) \leq 1$, Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond, p is an integer from 1 to 6, X is a divalent group represented by general formula (4) or general formula (5)

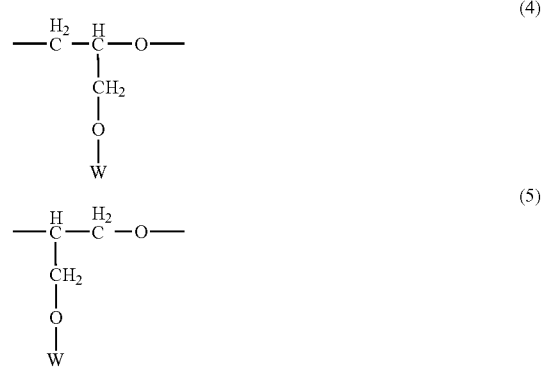

(in the preceding formula, W in the X in the organic group represented by general formula (3) is a monovalent hydrocarbyl group that does not contain an aliphatically unsaturated bond), wherein the configuration of the X and Z groups may be random, block, alternating, or a combination of the preceding];

a has an average value of $1.0 \leq a \leq 2.5$; b has an average value of $0.001 \leq b \leq 1.5$; and a and b satisfy an average of $1.001 \leq a+b \leq 3.0$};

a polyether-modified organopolysiloxane represented by average structural formula (8), $$A[(R^6)_2 SiO]_x [(R^6)(R^2)SiO]_y Si(R^6)_2 A \quad (8)$$

in the formula, $R^6$ is a monovalent hydrocarbyl group that does not contain an aliphatically unsaturated bond; $R^2$ is an organic group represented by general formula (3) above; A is $R^6$ or $R^2$; x is 0-500; y is 0-100; x +y is 1-600; and when y is 0, at least one of A is $R^2$;

a polyether-modified organopolysiloxane represented by average structural formula (10),

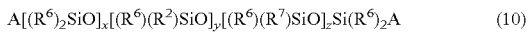 (10)

in the formula, $R^6$; A; x ;y; z are as defined above; $R^2$ is an organic group represented by general formula (3) above; $R^7$ is an organic group represented by general formula (2)

 (2)

{in the formula, $R^3$ is a (p+1)-valent hydrocarbyl group having 2 to 20 carbon atoms that does not contain an aliphatically unsaturated bond or is a group comprising said hydrocarbyl group having an ether linkage (C—O—C) therein, Z in the organic group represented by general formula (2) is an oxyalkylene group having 2 to 6 carbon atoms, m is 0-200, Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond, and p is an integer from 1 to 6};

a diorganopolysiloxane-polyether block copolymer having a main chain represented by general formula (13) or general formula (59),

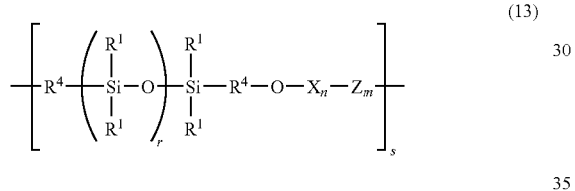 (13)

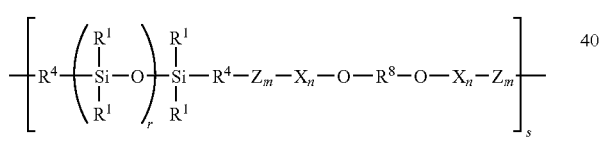 (59)

wherein $R^1$ therein is a monovalent hydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, $R^8$ is a divalent hydrocarbyl group having 2 to °carbon atoms that does not contain an aliphatically unsaturated bond or is a group comprising said hydrocarbyl group having an ether linkage (C—O—C) therein, n is 1-200, r is an integer from 1 to 1000, and s is an integer with a value of at least 2, and X is a divalent group represented by general formula (4) or general formula (5)

 (4)

 (5)

(in the preceding formulas, W in the group X is a monovalent hydrocarbyl group that does not contain an aliphatically unsaturated bond, and Z is not present (that is, m=0);

a diorganopolysiloxane-polyether block copolymer represented by average structural formula (14), average structural formula (17), or average structural formula (60),

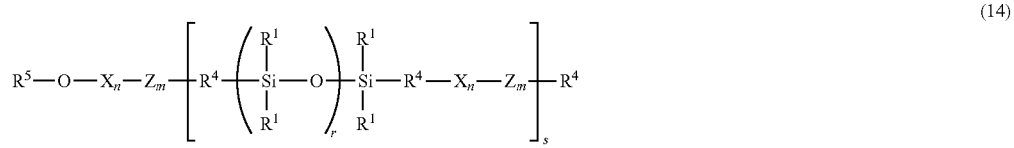 (14)

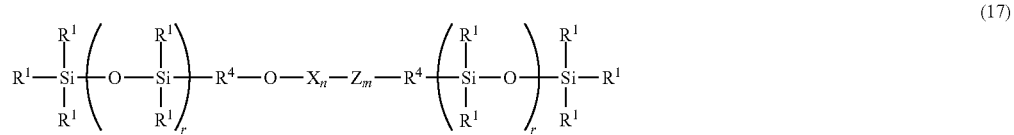 (17)

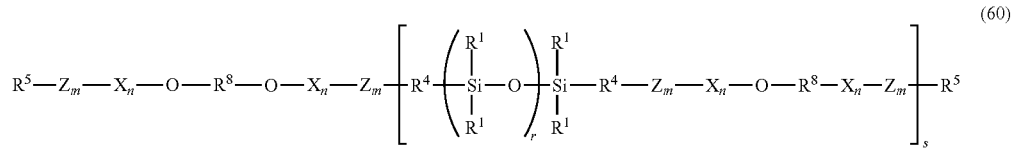 (60)

wherein $R^1$ therein is a monovalent hydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, $R^5$ is a double bond-terminated monovalent hydrocarbyl group or a group comprising said hydrocarbyl group having an ether linkage (C—O—C) therein), $R^8$ is a divalent hydrocarbyl group having 2 to 20 carbon atoms that does not contain an aliphatically unsaturated bond or is a group comprising said hydrocarbyl group having an ether linkage (C—O—C) therein, n is 1-200, r is an integer from 1 to 1000, and s is an integer with a value of at least 2, and X is a divalent group represented by general formula (4) or general formula (5)

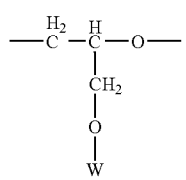
(4)

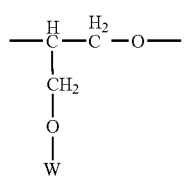
(5)

in the preceding formulas, W in the group X is a monovalent hydrocarbyl group that does not contain an aliphatically unsaturated bond, and Z is not present (that is, m=0); and a diorganopolysiloxane-polyether block copolymer represented by average structural formula (19),

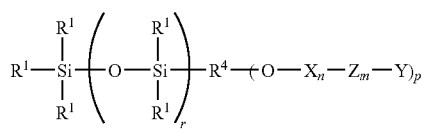
(19)

wherein $R^1$ therein is a monovalent hydrocarbyl group that does not contain an aliphatically unsaturated bond, $R^4$ is a divalent hydrocarbyl group having 2 to 20 carbon atoms that does not contain an aliphatically unsaturated bond or is a group comprising said hydrocarbyl group having an ether linkage (C—O—C) therein, W in the group X is a monovalent hydrocarbyl group that does not contain an aliphatically unsaturated bond, Z is not present (that is, m=0), n is 1-200, r is an integer from 1 to 1000, p is an integer from 1 to 6, and Y is hydrogen atom or a monovalent hydrocarbyl group that contains no more than 20 carbon atoms and that does not contain an aliphatically unsaturated bond or an acyl group that contains no more than 20 carbon atoms and that does not contain an aliphatically unsaturated bond.

38. The cosmetic according to claim 37, wherein the monovalent hydrocarbyl group that does not contain an aliphatically unsaturated bond constituting $R^1$ is an alkyl group; the divalent hydrocarbyl group having 2 to 20 carbon atoms that does not contain an aliphatically unsaturated bond constituting $R^4$ or $R^8$ is an alkylene group having 2 to 20 carbon atoms; the group comprising said divalent hydrocarbyl group having an ether linkage therein is an alkyleneoxyalkylene group having 2 to 20 carbon atoms; $R^3$ in the organic group represented by general formula (3) is an alkylene or alkyleneoxyalkylen group having 2 to 20 carbon atoms; Z is not present (that is, m=0); W in the group X is an alkyl group; Y is hydrogen atom or an alkyl group having no more than 20 carbon atoms or saturated aliphatic acyl group having no more than 20 carbon atoms; and p is 1 or 2.

39. The cosmetic according to claim 38, wherein the alkyl constituting $R^1$ is methyl; the alkylene constituting $R^3$ or $R^4$ is propylene or butylene; the alkyleneoxyalkylene constituting $R^3$, $R^4$, or $R^8$ is propyleneoxyethylene, ethyleneoxyethylene, propyleneoxypropylene, the group represented by formula (20) as given above, or the group represented by formula (21) as given above; and the alkyl constituting W in the group X is an alkyl having 1 to 4 carbon atoms.

* * * * *